(12) United States Patent
McFarland et al.

(10) Patent No.: US 8,663,956 B2
(45) Date of Patent: Mar. 4, 2014

(54) RECOMBINANT MICROORGANISMS FOR PRODUCTION C4-DICARBOXYLIC ACIDS

(75) Inventors: Sarah McFarland, Sacramento, CA (US); Stephen Brown, Davis, CA (US); Sheryl Luttringer, Loomis, CA (US)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 13/588,322

(22) Filed: Aug. 17, 2012

(65) Prior Publication Data

US 2013/0059353 A1 Mar. 7, 2013

Related U.S. Application Data

(60) Provisional application No. 61/525,345, filed on Aug. 19, 2011.

(51) Int. Cl.
*C12N 1/15* (2006.01)

(52) U.S. Cl.
USPC ..................................... 435/145; 435/254.11

(58) Field of Classification Search
USPC ........................................... 435/145, 254.11
See application file for complete search history.

(56) References Cited

U.S. PATENT DOCUMENTS

| | | | |
|---|---|---|---|
| 3,063,910 | A | 11/1962 | Abe et al. |
| 5,536,661 | A | 7/1996 | Boel et al. |
| 7,504,490 | B1 | 3/2009 | Weinstock et al. |
| 2011/0053233 | A1 | 3/2011 | Brown et al. |
| 2011/0111453 | A1 | 5/2011 | McBrayer et al. |

FOREIGN PATENT DOCUMENTS

| | | | |
|---|---|---|---|
| EP | 2471943 | A1 | 7/2010 |
| WO | 2007061590 | A1 | 5/2007 |
| WO | 2008144626 | A1 | 11/2008 |
| WO | 2009011974 | A1 | 1/2009 |
| WO | 2009065778 | A1 | 5/2009 |
| WO | 2009155382 | A1 | 12/2009 |
| WO | 2010003728 | A1 | 1/2010 |
| WO | 2010111344 | A2 | 9/2010 |
| WO | 2011024583 | A1 | 3/2011 |
| WO | 2011028643 | A1 | 3/2011 |
| WO | 2011066304 | A2 | 6/2011 |

OTHER PUBLICATIONS

Chica et al., Current Opinion Biotechnol. 2005, 16(4): 378-84.*
Sen et al., Appl. Biochem. Biotechnol. 2007, 143(3): 212-23.*
Burgess et al., Journal of Cell Biology, Nov. 1990, vol. 111, pp. 2129-2138.*
Lazar et al., Molecular and Cellular Biology, Mar. 1988, vol. 8, No. 3, pp. 1247-1252.*
Schwartz et al., Proc. Natl. Acad. Sci. USA, vol. 1987; 84:6408-6411.*
Acland et al., Nature, 1990, vol. 343, pp. 662-665.*
Lin et al., Biochemistry, 1975. 14: 1559-1563.*
Ludwig et al, 1998, Plant Physiol 117 (3), 1071-1081.
WO 2011-024583—Eng Equiv—EP 2 471 943.
Battat et al, 1991, Biotechnol Bioeng 37, 1108-1116.
Bauer et al, 1999, FEMS Microbiol Lett 179, 107-113.
Bercovitz et al, 1990, Appl Environ Microbiol 56(6), 1594-1597.
Birren et al, 2008—UniProt, Access No. B6JXU3.
Camarasa et al, 2001, Appl Environ Microbiol 67(9), 4144-4151.
Elleuche et al, 2009, Curr Genet 55, 211-222.
Fedorova et al, 2008, PLoS Genetics 4(4), 1-13.
Goldberg et al, 2006, J Chem Technol Biotechnol 81(10), 1601-1611.
Grobler et al, 1995, Yeast 11, 1485-1491.
Lubertozzi et al, 2008, Biotechnol Advances 27, 53-75.
Machida et al, 2005, Nature 438—1157-1161—UniProt, Access No. Q2UGL1.
Machida et al, 2005, Nature 438—157-1161—UniProt, Access No. Q2USG3.
Nevoigt, 2008, Microbiol Mol Biol Revs 72(3), 379-412.
Nielsen et al, 2008, FEMS Yeast Res 8, 122-131.
Nierman et al, 2005, Nature 438(22), 1151-1156.
Nierman et al, 2005, Nature 438(22), 1151-1156—UniProt, Access No. Q4WCF3.
Nierman et al, 2008—Genbank, Access No. XM_001276571.
Peleg et al, 1988, Appl Microbiol Biotechnol 28, 69-75.
Pines et al, 1997, Appl Microbiol Biotechnol 48, 248-255.
Sauer et al, 2008, Trends Biotechnol 26, 100-108.
Whisstock et al 2003 QTR Rev Biophys 36(3) 307-340.
Zelle et al, 2008, Appl Environ Microbiol 74, 2766-2777.
Zelle, 2011, PhD Thesis, Delft University of Technology, Delft.
Winkler et al, 2009—Geneseq, Access No. ATT44026.
Fedorova et al, 2007—UniProt, Access No. A1C406.
Bush et al, 2010, Geneseq Access No. AWP70496.

* cited by examiner

*Primary Examiner* — Tekchand Saidha
*Assistant Examiner* — Rama P Ramanujam
(74) *Attorney, Agent, or Firm* — Eric J. Fechter

(57) ABSTRACT

Provided herein are host cells comprising carbonic anhydrase activity, wherein the cells are capable of producing C4-dicarboxylic acid. Also provided are methods of producing C4-dicarboxylic acid comprising (a) cultivating the host cells having carbonic anhydrase activity in a medium under suitable conditions to produce C4-dicarboxylic acid; and (b) recovering the C4-dicarboxylic acid.

28 Claims, 20 Drawing Sheets

```
              M   E   S       S   A   V   Q       E   P   T       Q   Q   R       S   L   R   D       R   I   F
   1 ATGGAATCCA GCGCTGTACA GGAGCCGACT CAACAGCGCT CTTTGCGGGA TCGCATTTTT
          N  L  F       R   T   S   S       S   N   D       A   P   G       L   P   A   R       L   V   T
  61 AACCTCTTTC GTACCTCTTC CTCAAATGAT GCCCCGGGTC TTCCGGCAAG ACTCGTAACC
          A  E  S       A   A   Q   N       E   G   S       A   L   I       Y   P   P   R       E   P   D
 121 GCTGAGAGCG CAGCGCAAAA CGAAGGGTCG GCGTTAATCT ATCCGCCACG GGAGCCTGAT
          A  R  T       R   L   L   E       S   Y   D       R   G   E       R   G   L   R       N   S   G
 181 GCAAGGACTC GTCTTCTCGA ATCGTACGAT CGCGGGAAC GTGGTCTGAG GAACTCCGGC
          V  H  G       T   F   S   S       R   P   E       Q   E   E       I   Q   K   W       D   A   S
 241 GTTCATGGGA CTTTTTCTTC ACGACCTGAA CAGGAAGAAA TCCAAAAATG GGATGCAAGC
          S  L  Q       N   A   G   N       E   E   R       S   Q   S       P   G   G   A       D   G   H
 301 TCTTTGCAGA ATGCTGGTAA CGAAGAAAGA TCTCAGTCCC CAGGAGGAGC AGACGGCCAT
          I  G  S       P   G   D   V       S   G   Y       P   Q   G       P   E   N   I       P   S   L
 361 ATTGGGTCTC CCGGCGACGT CTCAGGATAC CCACAGGGAC CAGAGAATAT ACCATCGCTA
          D  S  S       F   T   A   L       H   M   K       N   H   K       S   L
 421 GACTCCTCTT TCACAGCATT GCACATGAAG AATCATAAAT CTCT*GTAGGT TTATAATCAC*
 481 *GTTCGCCCTG CTTTCTAACA CAATTGTTAT CTCCATCGTG GAGACAACTA ACGTTCATCA*
          Y  I  S       Y   Y   I       P   F   F       N   W   I       T   Q   Y   R       W   S   Y
 541 A*C*GTATATAT CTTACTACAT CCCATTTTTC AATTGGATTA CTCAATACCG GTGGTCGTAC
          I  R  G       D   L   V   A       A   T   T       I   A   S       I   Y   I   P       M   A   L
 601 ATTCGAGGTG ATTTGGTTGC TGCGACAACC ATTGCGTCCA TCTATATCCC TATGGCTTTG
          S  L  S       S   N   L   A       H   A   P       P   I   N       G   L   Y   S       F   V   I
 661 TCCTTATCCT CAAATCTCGC CCACGCACCT CCTATCAATG GCCTCTACTC TTTTGTGATC
          N  P  F       I   Y   A   I       F   G   S       S   P   L       L   I   V   G       P   E   A
 721 AACCCTTTCA TCTATGCGAT CTTCGGGAGC AGCCCGCTGT TAATAGTGGG CCCAGAAGCA
          A  G  S       L   L   T   G       T   I   V       K   T   S       V   R   P   G       P   S   G
 781 GCAGGCTCCT TGCTTACTGG CACGATTGTC AAAACTAGTG TCAGACCAGG CCCATCTGGT
          E  D  D       E   V   A   N       A   I   V       G   I   A       T   A   M   A       G   A
 841 GAGGACGACG AAGTAGCGAA TGCCATCGTG GTCGGCATAG CCACTGCAAT GGCGGGCGCC
          M  I  L       I   A   G   L       T   R   L       G   F   L       D   N   V   L       S   R   P
 901 ATGATACTGA TCGCTGGGCT TACACGGCTG GGATTTCTGG ACAATGTGCT GAGCCGGCCC
          F  L  R       G   F   I   T       A   I   G       F   V   I       F   V   D   Q       L   I   P
 961 TTTCTTAGGG GTTTCATTAC AGCGATCGGT TTTGTGATTT TTGTGGATCA ACTCATCCCC
          E  V  G       L   T   E   L       A   K   E       A   G   V       T   H   G   T       T   V   D
1021 GAAGTCGGAT TGACCGAGCT AGCAAAGGAA GCTGGTGTTA CCCATGGGAC TACAGTTGAC
          K  L  M       F   L   I   R       N   I   G       G   C   H       A   L   T   T       A   V   A
1081 AAGCTCATGT TCCTTATAAG AAACATAGGA GGTTGCCATG CGCTTACAAC CGCGGTGGCT
          F  G  S       F   A   I   I       M   V   F       R
1141 TTTGGGAGCT TTGCTATTAT AATGGTATTT CG*GTTAGTGT TGGTGACTCG GAAGCCTGGT*
                                                        T   L       K   K   M       L   Q   P   R       Y   P   Q
1201 *GCTTAGACTG ATTACCATTA CAG*GACTCTC AAGAAAATGC TCCAACGCCG GTATCCTCAG
          V  I  Y       L   P   D   R       I   L   V       V   I   L       S   A   V   L       T   W   H
1261 GTGATTTATC TTCCGGACCG AATTCTCGTA GTTATTCTTT CAGCCGTCCT GACATGGCAT
          L  G  W       D   D   K   G       L   E   I       L   G   P       L   K   Q   N       A   N   G
1321 CTTGGTTGGG ATGACAAAGG GTTGGAGATT CTTGGGCCCT TGAAACAAAA TGCCAATGGC
          L  F  A       F   K   W   P       F   Q   F       S   Q   M       K   H   V   R       A   A   M
1381 CTTTTTGCGT TCAAATGGCC TTTCCAGTTT AGCCAGATGA AGCATGTACG CGCTGCAATG
          S  T  S       F   V   I   A       L   L   G       F   F   E       S   S   V   A       K   G
1441 AGTACTTCTT TCGTCATCGC GTTACTTGGC TTTTTCGAGT CTTCTGTTGC CGCCAAGGGA
          L  S  G       E   A   R   Q       E   G   V       Q   G   M       P   V   S   A       N   R   E
1501 CTTAGTGGCG AGGCCAGACA AGAAGGTGTC CAGGGAATGC CTGTCAGTGC TAACAGAGAG
          M  V  A       L   G   L   A       N   T   V       G   G   C       F   M   A   L       P   A   F
1561 ATGGTGGCGC TGGGTCTTGC TAATACTGTG GGGGCTGTT TCATGGCGCT TCCTGCGTTT
```

Fig. 3A

```
           G  G  Y     A  R  S  K     V  N  A     S  T  G     A  R  S     P  M  S  S
1621 GGTGGCTATG CAAGAAGCAA AGTCAACGCT TCAACTGGAG CTCGGTCTCC GATGAGCAGC
     I  F  L     S  I  I  T     F  V  C     I  M  V     L  L  P  Y     L  Y  Y
1681 ATTTTCCTGA GCATTATTAC CTTTGTTTGT ATCATGGTGC TTTTGCCGTA CTTATACTAT
     L  P
1741 CTTCCGGTGA GTCTCGACCC CAAATACTTC CGAGCGAAGG CTGAGAAAAT ATGTTGCAAT
            K  A  V  L     S  S  M  I     S  V  V     A  F  S     L  I  E  E
1801 AATTCAGAAA GCCGTTCTTT CTTCTATGAT ATCTGTCGTC GCATTCAGTC TCATTGAAGA
        C  P  H  D  V  A     F  F  I  R     L  R  G     W  T  E     L  A  L  M
1861 ATGTCCTCAC GACGTGGCTT TCTTTATCCG ACTGCGCGGA TGGACGGAGC TAGCCCTAAT
     L  L  I     F  V  S     T  I  F  Y     S  L  E     L  G  I     A  L  G  I
1921 GCTTCTCATC TTTGTCTCGA CTATTTTCTA TTCTCTAGAG CTGGGAATTG CCCTTGGTAT
     G  L  S     I  L  I     L  I  R  H     S  T  Q     P  R  I     Q  I  L  G
1981 TGGCCTTTCT ATCTTGATCC TTATTCGCCA TTCTACGCAG CCTCGGATCC AAATTCTGGG
     K  I  A     G  T  T     D  R  F  D     N  A  E     L  H  P     E  S  V  E
2041 TAAGATAGCA GGCACTACCG ACCGTTTCGA TAACGCTGAA CTCCACCCCG AGAGCGTTGA
     L  I  E     G  A  L     I  V  K  I     P  E  P     L  T  F     A  N  T  G
2101 GTTAATCGAA GGCGCGCTTA TTGTTAAGAT CCCGGAACCG CTCACCTTTG CCAATACTGG
     E  L  K     N  R  L     R  R  L  E     L  Y  G     S  S  R     A  H  P  S
2161 TGAGCTCAAG AATCGTCTTC GGCGGTTGGA ATTATATGGC AGTAGCCGAG CGCACCCTTC
     L  P  P     T  R  T     P  E  H  N     K  N  I     I  F  D     V  H  G  V
2221 TCTTCCCCCC ACGCGCACCC CCGAACATAA CAAGAATATT ATATTTGATG TTCATGGTGT
     T  S  I     D  G  S     G  T  Q  V     L  Y  E     I  V  D     G  Y  A  D
2281 TACTAGCATC GATGGTTCCG GTACGCAAGT CTTATATGAG ATTGTGGACG GATATGCAGA
     Q  G  V     S  V  F     F  C  R  V     A  T  R     N  V  F     R  M  F  E
2341 CCAGGGGGTC AGCGTCTTCT TCTGCCGCGT CGCAACTCGC AATGTTTTCC GCATGTTTGA
     R  S  G     I  V  E     R  C  G  G     I  T  H     F  V  H     G  V  D  E
2401 ACGAAGTGGA ATTGTGGAAC GATGCGGTGG GATAACGCAC TTCGTTCATG GTGTCGACGA
     A  L  R     L  A  E     S  E  D  E     I  E  I     *
2461 AGCCCTCCGC CTTGCCGAAT CGGAAGACGA GATTGAAATC TGA
```

Fig. 3B

```
              M   P   G   D   L   K   T   K   I   G   H   G   A   A   K   A   L   G   I   K
   1 ATGCCGGGCG ATCTCAAAAC CAAAATTGGT CACGGCGCGG CCAAGGCCTT GGGGATCAAG
     I   P   Y   R   D   P   L   G   V   H   A   D   P   V   T   R   G   E   S   M
  61 ATCCCCTACC GTGATCCTCT CGGAGTTCAT GCTGACCCAG TCACACGAGG CGAGTCGATG
     F   S   V   G   T   I   D   T   Y   S   Y   L   E   P   E   P   T   P   A   E
 121 TTCTCCGTCG GAACGATCGA CACATACTCC TATCTCGAGC CCGAACCCAC TCCCGCTGAA
     W   L   K   E   V   C   P   S   W   H   Q   V   G   R   Y   F   Y   N   L   F
 181 TGGCTGAAGG AAGTCTGCCC TAGCTGGCAT CAGGTGGGCC GTTATTTTA CAACCTTTTC
     P   F   L   S   W   I   T   R   Y   N   L   Q   W   L   L   G   D   M   I   A
 241 CCTTTCCTCT CGTGGATTAC GAGGTACAAC TTGCAATGGT TGCTGGGAGA TATGATTGCC

301 GGTAAGAGCC TTTCCACTGT GTTTGATTTG ATCGACAAGT AGACAACATA CTCATTGGAA
                G   V   T   V   G   A   V   V   V   P   Q   G   M   A   Y   A   K   L   A
 361 TGCAGGCGTC ACGGTCGGTG CTGTGGTCGT TCCGCAGGGA ATGGCCTACG CTAAACTGGC
     N   L   P   V   E   Y   G   L   Y   S   F   M   G   V   L   I   Y   W   F
 421 AAACCTACCT GTAGAGTATG GTCTCTATTC CTCGTTCATG GGTGTTCTCA TTTATTGGTT
     F   A   T   S   K   D   I   T   I   G
 481 TTTTGCCACC TCAAAGGATA TCACCATTGG TGTAAGTCAT TCTGCACCCA TGTCAGCATG
                                                  P   V   A   V   M   S   T   L   T
 541 TATCTTGCTA ATATAGTATC TTCCCTGTTC AGCCGGTGGC TGTCATGTCT ACCCTTACAG
     G   K   I   V   A   E   A   Q   T   K   L   P   D   V   E   G   H   V   I   A
 601 GTAAGATAGT TGCCGAGGCG CAAACGAAGC TCCCAGATGT CGAAGGGCAT GTAATCGCCT
     S   C   L   A   I   I   C   G   A   V   C   A   M   G   L   L   R   L   G
 661 CCTGTTTGGC TATCATTTGT GGAGCCGTGG TTTGCGCTAT GGGCCTGCTT CGGCTGGGAT
     F   I   V   D   F   I   P   L   P   A   I   S   A   F   M   T   G   S   A   I
 721 TTATCGTGGA TTTCATTCCT CTGCCGGCAA TTTCAGCTTT CATGACGGGT TCCGCCATCA
     N   I   C   S   G   Q   V   K   D   M   L   G   E   T   A   D   F   S   T   K
 781 ATATCTGCTC CGGACAGGTC AAAGACATGC TGGGAGAGAC GGCCGACTTC TCGACGAAAG
     D   S   T   Y   L   V   I   I   N   T   L   K   H   L   P   S   A   K   I   D
 841 ATTCTACCTA TCTGGTTATC ATCAACACCC TCAAGCATCT TCCCTCCGCA AAAATCGATG
     A   A   M   G   V   S   A   L   A   M   L   Y   I   I   R   S   G   C   N   Y
 901 CCGCCATGGG TGTCAGTGCT TTAGCTATGC TGTACATTAT CCGTTCGGGT TGCAATTATG
     G   A   K   K   F   P   R   H   A   K   V   W   F   F   V   S   T   L   R   T
 961 GCGCGAAGAA GTTCCCCCGT CATGCCAAGG TTTGGTTCTT CGTTTCGACT TTGCGCACAG
     V   F   V   I   L   F   Y   T   M   I   S   A   A   V   N   L   H   R   R   S
1021 TGTTCGTGAT CTTGTTCTAT ACGATGATCA GTGCCGCTGT GAACTTGCAC CGGCGGTCTA
     N   P   R   F   K   L   L   G   K   V   P   R   G   F   Q   H   A   A   V   P
1081 ACCCGCGGTT CAAGCTCCTG GGTAAAGTTC CTCGTGGTTT CCAACATGCG GCTGTCCCTC
     Q   V   N   S   R   I   I   S   A   F   A   S   E   L   P   A   S   I   I   V
1141 AGGTAAATTC GAGGATCATC AGCGCATTTG CTAGCGAACT TCCTGCTTCG ATTATTGTCC
     L   L   I   E   H   I   A   I   S   K   S   F   G   R   V   N   N   Y   T   I
1201 TGCTTATCGA ACACATCGCT ATCTCGAAAT CCTTTGGCCG TGTCAACAAC TACACAATTG
     D   P   S   Q   E   L   V   A   I   G   V   S   N   L   L   G   P   F   L   G
1261 ATCCCTCTCA GGAGCTGGTT GCTATTGGTG TGTCGAACTT GCTTGGACCG TTCCTTGGTG
     G   Y   P   A   T   G   S   F   S   R   T   A   I   K   S   K   A   G   V   R
1321 GTTACCCAGC GACTGGATCG TTCTCCCGAA CTGCAATCAA ATCGAAAGCG GGTGTCCGCA
     T   P   L   A   G   V   I   T   A   V   V   L   L   A   I   Y   A   L   P
1381 CCCCACTTGC CGGTGTTATT ACTGCGGTTG TTGTCCTCCT CGCCATTTAC GCTCTGCCCG
     A   V   F   F   Y   I   P   K   A   S   L   A   G   V   I   I   H   A   V   G
1441 CTGTCTTCTT TTACATCCCG AAAGCTTCCC TTGCTGGTGT CATCATTCAT GCAGTCGGTG
     D   L   I   T   P   P   N   T   V   Y   Q   F   W   R   V   S   P   L   D   A
1501 ACCTCATTAC CCCACCAAAC ACCGTTTACC AGTTCTGGCG CGTGTCCCCT CTGGATGCGA
     I   I   F   F   I   G   V   I   V   T   V   F   T   T   I   E   I   G   I   Y
1561 TCATTTTCTT TATCGGTGTT ATCGTGACTG TCTTCACCAC GATTGAGATC GGCATTTACT
     C   T   V   C   V   S   V   A   I   L   L   F   R   V   A   K   A   R   G   Q
1621 GTACCGTTTG TGTGTCTGTT GCCATTCTGC TGTTCCGCGT CGCCAAGGCC CGCGGTCAAT
```

Fig. 4A

```
        F   L   G   R     V   T   I     H   S   V     I   G   D   H     L   V   Q     D   D   G
1741 TCTTAGGAAG AGTCACTATC CACTCGGTGA TCGGTGACCA TCTGGTACAG GATGATGGGA
        K   Y   G   S     A   N   S     P   N   A     A   S   D   D     K   D   E     L   S   R
1801 AATATGGGTC TGCCAACTCC CCTAATGCTG CCAGCGATGA CAAAGATGAA TTGAGCCGGT
        S   I   F   L     P   I   N     H   T   D     G   S   N   P     D   V   E     V   Q   Q
1861 CTATCTTCTT GCCTATCAAC CACACGGACG GATCGAATCC CGATGTCGAG GTGCAGCAAC
        P   Y   P   G     I   F   I     Y   R   F     S   E   G   F     N   Y   P     N   A   N
1921 CTTATCCTGG TATCTTCATC TACCGATTCT CGGAAGGATT CAACTACCCC AATGCCAATC
        H   Y   T   D     Y   L   V     Q   T   I     F   K   H   T     R   R   T     N   P   F
1981 ACTACACCGA TTATTTGGTC CAGACTATCT TCAAGCATAC ACGTCGCACA AATCCGTTCT
        S   Y   G   K     P   G   D     R   P   W     N   N   P   G     P   R   R     G   K   S
2041 CCTACGGTAA ACCGGGTGAT CGGCCATGGA ATAATCCTGG CCCTCGCAGG GGCAAGTCTG
        E   D   D   E     S   H   L     P   L   L     Q   A   V   I     L   D   F     S   S   V
2101 AAGATGACGA GTCGCATTTG CCCTTACTGC AGGCTGTCAT TCTTGACTTC TCATCCGTCA
        N   N   V   D     V   T   S     V   Q   N     L   I   D   V     R   N   Q     L   D   L
2161 ACAATGTTGA TGTGACCTCG GTCCAGAACC TCATCGATGT CCGCAATCAA CTCGACCTCT
        Y   A   S   P     K   T   V     Q   W   H     F   A   H   I     N   N   R     W   T   K
2221 ACGCTTCGCC TAAGACTGTG CAGTGGCACT TTGCTCATAT TAACAACCGC TGGACGAAAC
        R   A   L   A     A   G   F     G   F     P   S   P   D     S   D   E     G   F   Q
2281 GAGCCCTTGC AGCAGCAGGT TTCGGCTTCC CATCTCCGGA CTCGGATGAA GGATTCCAGA
        R   W   K   P     I   F   S     V   A   E     I   E   G   S     A   S   A     A   A   H
2341 GATGGAAGCC AATTTTCAGC GTGGCTGAGA TCGAAGGCAG TGCCTCTGCC GCAGCTCATG
        A   E   M   V     N   N   R     H   T   Q     H   N   I   K     S   E   D     L   E   H
2401 CAGAGATGGT GAACAACAGA CACACCCAGC ATAACATCAA GAGCGAAGAC CTCGAGCATG
        G   L   K   H     D   S   E     T   T   E     R   E   T   H     G   I   E     E   S   S
2461 GCCTCAAGCA CGATTCAGAG ACCACCGAGC GTGAGACACA CGGCATCGAA GAATCCTCCG
        D   A   S   S     T   R   E     D   K   L     Q   R   D   L     K   D   S     K   A   Y
2521 ATGCCAGCAG CACCCGGGAG GACAAGTTGC AACGGGACCT GAAGGATAGC AAGGCTTACC
        R   S   R   R     R   V   A     M   V   Q     G   L   N   R     P   F   F     H   I   D
2581 GCAGTCGCCG AAGGGTCGCT ATGGTGCAGG GCCTCAACCG GCCATTCTTC CACATCGACC
        L   T   S   A     L   Q   S     A   L   A     N   A   G   E     Q   P   D     P   K   M
2641 TGACTAGTGC ACTGCAGAGT GCCTTGGCCA ACGCGGGCGA GCAGCCGGAC CCTAAAATGA
        N   V   L   D     A   *
2701 ATGTCCTTGA TGCATAG
```

Fig. 4B

```
        M   H   D     H   S   T   G     S   S   P     Y   I   S     D   V   E   T     L   N   H
   1 ATGCACGACC ACAGCACTGG ATCTAGTCCA TACATCTCGG ACGTGGAAAC CTTGAACCAC
        A   C   E     K   S   V   N     P   E   T     K   V   S     Q   P   Q   E     S   P   I
  61 GCCTGCGAGA AGTCCGTCAA CCCCGAGACC AAAGTCTCCC AGCCTCAGGA ATCTCCCATT
        I   S   N     N   E   H   Q     E   F   V     K   L   G     I   R   Q   R     L   R   H
 121 ATCAGCAATA ATGAACATCA GGAGTTTGTT AAGCTGGGCA TCCGCCAACG GCTGCGTCAT
        F   T   W     A   W   Y   T     L   T   M     S   A   G     G   L   A   L     L   L   R
 181 TTCACCTGGG CCTGGTATAC CCTAACCATG AGCGCAGGTG GACTGGCCCT TCTTCTCCGC
        N   Q   P     Y   Q   F   K     G   L   K     E   I   G     L   V   V   Y     I   A   N
 241 AACCAGCCGT ATCAATTCAA GGGGTTGAAG GAGATAGGCC TGGTGGTATA CATAGCCAAT
        L   V   F     F   T   I   I     G   S   L     M   I   T     R   F   V   L     Y   N   N
 301 CTCGTCTTCT TTACTATCAT CGGCTCTCTT ATGATCACCA GGTTTGTTCT TTACAACAAC
        L   M   D     S   L   R   H     D   R   E     G   F   F     F   P   T   F     W   L   S
 361 CTGATGGACT CTCTCCGCCA CGACCGAGAA GGTTTCTTCT TTCCAACCTT CTGGCTCTCC
        I   A   T     M   I   S   G     L   S   A     Y   F   S     T   E   D   T     H   R   L
 421 ATCGCCACCA TGATTAGTGG TCTATCTGCC TACTTCTCTA CTGAAGACAC GCACCGCCTC
        N   Y   A     L   E   G   L     F   W   A     Y   C   I     F   T   F   A     S   A   V
 481 AATTATGCTC TCGAGGGTCT CTTCTGGGCG TACTGTATCT TCACGTTTGC CTCAGCAGTG
        I   Q   Y     S   F   V   F     S   Y   H     T   F   P     L   Q   T   M     M   P   S
 541 ATCCAGTACT CCTTTGTCTT CTCCTATCAC ACGTTCCCTC TGCAAACTAT GATGCCATCA
        W   I   L     P   A   F   P     I   M   L     S   G   T     I   A   S   A     A   S   S
 601 TGGATCTTAC CGGCATTCCC TATCATGCTG AGCGGAACCA TTGCCTCTGC CGCTTCCAGC
        Y   Q   P     A   V   S   A     T   P   M     I   V   A     G   I   T   F     Q   G   L
 661 TACCAGCCTG CGGTGTCTGC CACGCCTATG ATTGTTGCCG GCATCACGTT CCAGGGACTC
        G   F   C     I   S   F   M     M   Y   A     H   Y   I     G   R   L   M     E   T   G
 721 GGATTCTGCA TCAGCTTCAT GATGTACGCC CACTACATCG GGCGTCTGAT GGAGACGGGC
        I   P   S     S   E   H   R     P   G   M     F   I   C     V   G   P   P     A   F   T
 781 ATCCCTTCGA GCGAGCACCG TCCTGGTATG TTCATCTGTG TCGGCCCCCC TGCCTTCACG
        L   L   A     I   I   G   M     A   N   G     L   P   E     G   F   S   I     L   G   D
 841 CTGCTGGCTA TCATCGGCAT GGCCAACGGC CTTCCCGAGG GCTTCAGTAT CCTGGGCGAT
        G   G   M     D   D   R   H     I   M   R     V   L   A     V   C   A   G     M   F   L
 901 GGTGGCATGG ACGACCGTCA CATCATGCGA GTACTGGCCG TCTGCGCGGG CATGTTCCTC
        W   A   L     S   I   W   F     F   C   V     A   L   G     S   V   V   R     A   P   P
 961 TGGGCTCTGA GCATTTGGTT CTTCTGTGTC GCTCTGGGCT CAGTTGTGCG GGCGCCTCCC
        H   D   F     H   L   N   W     W   A   M     V   F   P     N   T   G   L     T   L   A
1021 CATGATTTCC ACCTCAACTG GTGGGCTATG GTCTTCCCTA ACACCGGACT CACTCTCGCC
        T   I   T     L   A   K   S     L   D   S     A   A   L     K   W   V   G     V   G   M
1081 ACCATCACCC TGGCCAAGTC ACTGGACAGT GCCGCGTTGA AATGGGTGGG CGTGGGCATG
        S   L   C     V   I   C   M     F   I   F     V   F   V     S   T   I   R     A   V   L
1141 TCCCTCTGCG TGATCTGCAT GTTCATCTTC GTCTTCGTGA GCACCATTAG GGCTGTTCTC
        L   K   R     I   M   W     P   G   R   D     E   D   V     S   E   L   F     E   *
1201 TTGAAGAGGA TCATGTGGCC AGGTCGGGAT GAGGATGTGT CCGAGTTGTT CGAATGA
```

Fig. 6

```
          M   V   K   A
   1  ATGGTCAAAG CTGGTGAGTT AGCAATCCTT AACAGATGAC ACTCTCATAG GTACTAACTC
                  A   V   L   G   A   S   G   G   I   G   Q
  61  GAAACGTTAG CGGTACTTGG AGCTTCTGGT GGCATTGGCC AGGTATGGAT ATCCCCACGC
                                                              P   L   S
 121  CTTACAACCC TGGTCACAAT ATGACCTTGT TCGATACTGA CTATCTCCCA AGCCACTGTC
       L   L   L   K   T   C   P   L   V   E   E   L   A   L   Y   D   V   V   N   T
 181  TCTCCTGTTG AAGACCTGTC CCTTAGTTGA AGAGCTTGCT CTCTACGATG TTGTGAACAC
       P   G   V   A   A   D   L   S   H   I   S   S   I   A
 241  CCCTGGTGTT GCTGCTGATC TATCCCACAT CTCGTCTATC GCTGTACGTT ACTGCCACAA
                                                                          K
       I   S   G   F   L   P   K   D   D   G   L   K   Q   A   L   T   G   A   N   I
 301  TGCGAATTGC CCGATGGAAG AGGCGAAAAA TGGTATCTTG CTTACCTGGG CGATTAGAAA
 361  ATCTCTGGTT TTCTGCCCAA AGATGATGGG CTGAAGCAGG CCCTTACTGG TGCTAATATT
       V   V   I   P   A   G   I   P
 421  GTTGTCATCC CGGCTGGTAT TCCCCGTAAG TCCCTACCCT TTCGCATTGC TCCTCGTATG
                                           R   K   P   G   M   T   R   D   D
 481  TTCGCTGGTG GCCAGTTTTC TGATAGTTGA TAGGCAAGCC TGGTATGACC CGTGACGACC
       L   F   K   I   N   A   G   I   V   R   D   L   V   K   G   I   A   E   F   C
 541  TCTTCAAGAT CAACGCCGGC ATAGTGCGAG ACTTGGTCAA GGGTATCGCC GAGTTCTGCC
       P   K   A   F   V   L   V   I   S   N   P   V   N   S   T   V   P   I   A   A
 601  CCAAGGCCTT TGTTCTGGTT ATCTCAAACC CCGTTAATTC TACTGTTCCT ATTGCTGCAG
       E   V   L   K   A   A   G   V   F   D   P   K   R   L   F   G   V   T   T   L
 661  AGGTGCTCAA AGCCGCTGGC GTCTTTGACC CGAAGCGCCT CTTTGGTGTC ACCACACTGG
       D   V   V   R   A   E   T   F   T   Q   E   F   S   G   Q   K   D   P   S   A
 721  ACGTCGTTCG TGCAGAGACT TTCACCCAAG AGTTCTCGGG CCAGAAGGAT CCTTCTGCTG
       V   Q   I   P   V   V   G   H   S   G   E   T   I   V   P   L   F   S   K
 781  TTCAAATCCC AGTTGTTGGT GGCCACTCTG GAGAGACCAT TGTCCCCCTC TTCAGCAAGA
       T   T   P   A   I   Q   I   P   E   E   K   Y   D   A   L   I   H
 841  CTACCCCCGC AATTCAGATA CCCGAGGAGA AGTATGACGC ACTGATCCAC CGTAGGTTGT
                                                                      R   V   Q   F
 901  CCCAAAGAAT CTCATGAATA TCTTGCTGTA AGCACTAACT ATGCTTCAGG CGTCCAATTT
       G   G   D   E   V   V   Q   A   K   D   G   A   G   S   A   T   L   S   M   A
 961  GGTGGAGATG AGGTGGTCCA AGCTAAGGAC GGTGCTGGTT CCGCCACCTT GTCTATGGCC
       Y   A   G   Y   R
1021  TATGCCGGTT ACAGGTAGGG ATGCTGCGTA CCGTGAGAGC ACTCGCGGCT AACATGCCAT
           F   A   E   S   V   I   K   A   S   K   G   Q   T   G   I   V   E   P   T
1081  AGGTTCGCTG AGAGTGTAAT CAAAGCTTCA AAGGGTCAAA CGGGTATTGT CGAGCCTACC
       F   V   Y   L   P   G   I   P   G   G   D   E   I   V   K   A   T   G   V   E
1141  TTCGTCTACC TGCCTGGAAT TCCCGGCGGT GATGAGATCG TTAAGGCAAC TGGCGTGGAA
       F   F   S   T   L   V   T   L   G
1201  TTCTTCTCTA CTCTTGTAAC CTTAGGAGTA AGATTCATCT CCTCACAGAA TCTTCGTTCA
                                              T   N   G   A   E   K   A   S   N   V
1261  TATCACGCCA GGCTAACGCT ATTAAACAGA CTAATGGCGC AGAGAAGGCT AGCAACGTTC
       L   E   G   V   T   E   K   E   K   K   L   E   A   C   T   K   G   L   K
1321  TTGAGGGCGT GACCGAGAAG GAAAAGAAGC TTCTCGAGGC TTGCACGAAA GGCCTTAAGG
       G   N   I   E   K   G   I   D   F   V   K   N   P   P   P   K   *
1381  GTAATATCGA GAAAGGCATC GACTTCGTTA AGAACCCACC ACCAAAGTAA
```

Fig. 7

```
      M   A   A       P   F   R   Q       P   E   E       A   V   D       D   T   E   F       I   D   D
   1  ATGGCGGCTC  CGTTTCGTCA  GCCTGAGGAG  GCGGTCGATG  ACACCGAGTT  CATCGATGAC
      H   H   E       H   L   R   D       T   V   H       H   R   L       R   A   N   S       S   I   M
  61  CACCATGAAC  ACCTCCGTGA  TACCGTGCAC  CATCGGTTGC  GCGCCAATTC  CTCCATTATG
      H   F   Q       K   I   L   V       A   N   R       G   E   I       P   I   R   I       F   R   T
 121  CACTTCCAGA  AGATCCTCGT  CGCCAACCGT  GGTGAGATCC  CCATTCGTAT  CTTCAGAACG
      A   H   E       L   S   L   Q       T   V   A       I   Y   S       H   E   D   R       L   S   M
 181  GCCCACGAGC  TGTCCTTGCA  GACGGTTGCT  ATCTACTCTC  ATGAGGATCG  ACTGTCAATG
      H   R   Q       K   A   D   E       A   Y   M       I   G   H       R   G   Q   Y       T   P   V
 241  CACCGTCAAA  AGGCCGATGA  GGCCTACATG  ATTGGCCACC  GCGGTCAGTA  CACCCCTGTC
      G   A   Y       L   A   G   D       E   I   I       K   I   A       L   E   H   G       V   Q   L
 301  GGTGCGTACC  TGGCGGGCGA  TGAGATCATC  AAGATCGCCC  TGGAGCACGG  TGTCCAGCTG
      I   H   P       G   Y   G   F       L   S   E       N   A   D       F   A   R   K       V   E   N
 361  ATCCACCCGG  GCTACGGTTT  CTTGTCCGAG  AACGCCGACT  TCGCCCGCAA  GGTTGAGAAC
      A   G   I       V   F   V   G       P   T   P       D   T   I       D   S   L   G       D   K   V
 421  GCCGGCATTG  TCTTTGTGGG  ACCCACTCCC  GATACCATTG  ACAGCTTGGG  TGACAAGGTG
      S   A   R       R   L   A   I       K   C   E       V   P   V       V   P   G   T       E   G   P
 481  TCGGCCCGTC  GGCTGGCCAT  TAAGTGCGAG  GTCCCTGTCG  TTCCGGGTAC  GGAGGGCCCC
      V   E   R       Y   E   E   V       K   A   F       T   D   T       Y   G   F   P       I   I   I
 541  GTCGAGCGCT  ATGAGGAGGT  CAAGGCGTTC  ACAGACACCT  ATGGCTTCCC  CATCATCATC
      K   A   A       F   G   G   G       R   G   M       R   V   V       R   D   Q   A       E   L
 601  AAGGCTGCCT  TTGGCGGTGG  TGGCCGTGGT  ATGCGTGTGG  TCCGTGACCA  GGCCGAGCTG
      R   D   S       F   E   R   A       T   S   E       A   R   S       A   F   G   N       G   T   V
 661  CGTGACTCGT  TCGAGCGAGC  CACCTCTGAA  GCCCGCTCCG  CCTTCGGCAA  TGGTACCGTC
      F   V   E       R   F   L   D       K   P   K       H   I   E       V   Q   L   L       G   D   S
 721  TTCGTCGAGC  GCTTCCTCGA  CAAACCCAAG  CACATTGAAG  TCCAGCTTCT  GGGTGACAGC
      H   G   N       V   V   H   L       F   E   R       D   C   S       V   Q   R   R       H   Q   K
 781  CACGGCAACG  TTGTCCATCT  GTTTGAGCGT  GACTGCTCCG  TGCAGCGTCG  TCACCAGAAG
      V   V   E       V   A   P   A       K   D   L       P   A   D       V   R   D   R       I   L   A
 841  GTCGTTGAGG  TTGCTCCGGC  TAAGGACCTG  CCAGCCGATG  TCCGGGACCG  CATCCTGGCC
      D   A   V       K   L   A   K       S   V   N       Y   R   N       A   G   T   A       E   F   L
 901  GATGCTGTGA  AGCTGGCCAA  GTCCGTCAAC  TACCGTAACG  CCGGTACAGC  TGAGTTCCTG
      V   D   Q       Q   N   R   H       Y   F   I       E   I   N       P   R   I   Q       V   E   H
 961  GTGGACCAGC  AGAACCGCCA  CTACTTCATT  GAAATCAATC  CTCGTATCCA  AGTCGAGCAC
      T   I   T       E   E   I   T       G   I   D       I   V   A       A   Q   I   Q       I   A   A
1021  ACCATCACCG  AAGAGATTAC  TGGTATCGAT  ATCGTGGCTG  CACAGATCCA  GATTGCTGCT
      G   A   S       L   E   Q   L       G   L   T       Q   D   R       I   S   A   R       G   F   A
1081  GGTGCAAGCC  TCGAGCAACT  GGGCCTGACT  CAGGACCGCA  TCTCCGCCCG  CGGATTTGCC
      I   Q   C       R   I   T   T       E   D   P       A   K   G       F   S   P   D       T   G   K
1141  ATTCAATGTC  GTATCACCAC  GGAAGATCCC  GCCAAGGGGT  TCTCTCCGGA  TACTGGTAAG
      I   E   V       Y   R   S   A       G   G   N       G   V   R       L   D   G   G       N   G   F
1201  ATTGAGGTTT  ATCGTTCCGC  TGGTGGTAAC  GGTGTCCGTC  TGGATGGTGG  TAACGGTTTC
      A   G   A       I   I   T   P       H   Y   D       S   M   L       V   K   C   T       C   R   G
1261  GCTGGTGCTA  TCATCACCCC  TCACTACGAC  TCCATGCTGG  TCAAGTGCAC  CTGCCGTGGT
      S   T   Y       E   I   A   R       R   K   V       V   R   A       L   V   E   F       R   I   R
1321  TCGACCTATG  AAATCGCTCG  TCGCAAGGTT  GTGCGTGCCT  TGGTCGAGTT  CCGTATTCGT
      G   V   K       T   N   I   P       F   L   T       S   L   L       S   H   P   T       F   V   D
1381  GGTGTGAAGA  CCAACATTCC  CTTCCTGACT  TCGCTTCTGA  GCCACCCGAC  CTTCGTCGAT
      G   N   C       W   T   T   F       I   D   D       T   P   E       L   F   S   L       V   G   S
1441  GGAAACTGCT  GGACCACTTT  CATCGACGAC  ACCCCTGAAT  TGTTCTCTCT  TGTCGGCAGT
      Q   N   R       A   Q   K   L       L   A   Y       L   G   D       V   A   V   N       G   S   S
1501  CAGAACCGTG  CCCAGAAGCT  GCTCGCATAC  CTCGGCGATG  TAGCTGTCAA  CGGTAGTAGC
      I   K   G       Q   I   G   E       P   K   L       K   G   D       V   I   K   P       K   L   F
1561  ATCAAGGGCC  AAATTGGCGA  GCCCAAGCTC  AAGGGTGATG  TCATCAAGCC  GAAGCTTTTC
      D   A   E       G   K   P   L       D   V   S       A   P   C       T   K   G   W       K   Q   I
1621  GATGCCGAGG  GCAAGCCGCT  TGACGTTTCC  GCCCCCTGCA  CCAAGGGTTG  GAAGCAGATT
      L   D   R       E   G   P   A       A   F   K       A   V   R       A   N   K   G       C   L
1681  CTGGACCGGG  AGGGTCCGGC  TGCCTTTGCG  AAGGCCGTGC  GTGCCAACAA  GGGTTGCTTG
      I   M   D       T   T   W   R       D   A   H       Q   S   L       L   A   T   R       V   R   T
1741  ATCATGGATA  CTACCTGGCG  TGACGCCCAC  CAGTCTTTGC  TGGCCACCCG  TGTGCGTACC
      I   D   L       L   N   I   A       H   E   T       S   Y   A       Y   S   N   A       Y   S   L
1801  ATCGACTTGT  TGAACATCGC  CCATGAGACC  AGCTACGCCT  ACTCCAATGC  GTACAGTTTG
```

Fig. 9A

```
           E  C  W     G  G  A  T     F  D  V     A  M  R     F  L  Y  E     D  P  W
1861  GAATGCTGGG GTGGTGCTAC CTTCGATGTG GCCATGCTT TCCTCTATGA GGACCCCTGG
        D  R  L     R  K  M  R     K  A  V     P  N  I     P  F  Q  M     L  L  R
1921  GACCGCCTGC GCAAGATGCG TAAGGCTGTT CCTAACATCC CATTCCAGAT GTTGCTCCGT
        G  A  N     G  V  A  Y     S  S  L     P  D  N     A  I  Y  H     F  C  K
1981  GGTGCCAACG GTGTCGCCTA CTCTTCCCTC CCAGACAACG CCATCTACCA CTTCTGTAAG
        Q  A  K     K  C  G  V     D  I  F     R  V  F     D  A  L  N     D  V  D
2041  CAGGCTAAGA AGTGCGGTGT CGACATTTTC CGTGTTTTCG ACGCCCTCAA CGATGTCGAT
        Q  L  E     V  G  I  K     A  V  H     A  A  E     G  V  V  E     A  T  M
2101  CAGCTCGAGG TCGGTATCAA GGCTGTTCAT GCTGCCGAGG GTGTTGTCGA GGCCACCATG
        C  Y  S     G  D  M  L     N  P  H     K  K  Y     N  L  E  Y     Y  M  A
2161  TGCTACAGCG GTGACATGCT GAACCCCCAC AAGAAGTACA ACCTGGAGTA CTACATGGCC
        L  V  D     K  I  V  A     M  K  P     H  I  L     G  I  K  D     M  A  G
2221  TTGGTGGATA AGATTGTAGC CATGAAGCCT CACATCCTTG GTATCAAGGA TATGGCCGGT
        V  L  K     P  Q  A  A     R  L  L     V  G  S     I  R  Q  R     Y  P  D
2281  GTGCTGAAGC CCCAGGCCGC TCGCCTGTTG GTGGGCTCCA TCCGTCAGCG CTACCCTGAC
        L  P  I     H  V  H  T     H  D  S     A  G  T     G  V  A  S     M  I  A
2341  CTTCCCATCC ACGTCCACAC CCACGACTCC GCTGGTACTG GTGTAGCTTC CATGATTGCC
        C  A  Q     A  G  A  D     A  V  D     A  A  T     D  S  M  S     G  M  T
2401  TGTGCCCAGG CGGGTGCCGA CGCCGTGGAC GCCGCGACCG ACAGCATGTC CGGTATGACC
        S  Q  P     S  I  G  A     I  L  A     S  L  E     G  T  E  Q     D  P  G
2461  TCCCAGCCTA GCATTGGTGC CATTCTGGCC TCTCTTGAGG GCACTGAGCA AGACCCCGGT
        L  N  L     A  H  V  R     A  I  D     S  Y  W     A  Q  L  R     L  L  Y
2521  CTCAACCTCG CCCACGTGCG CGCTATTGAT AGCTACTGGG CACAGTTGCG CTTGCTCTAC
        S  P  F     E  A  G  L     T  G  P     D  P  E     V  Y  E  H     E  I  P
2581  TCTCCTTTCG AGGCGGGTCT CACTGGCCCC GACCCTGAGG TCTACGAGCA CGAGATCCCT
        G  G  Q     L  T  N  L     I  F  Q     A  S  Q     L  G  L  G     Q  Q  W
2641  GGTGGTCAGT TGACCAACCT TATCTTCCAG GCCAGTCAGC TCGGCTTGGG CCAGCAGTGG
        A  E  T     K  K  A  Y     E  A  A     N  D  L     L  G  D  I     V  K  V
2701  GCCGAAACCA AGAAGGCCTA TGAGGCGGCT AATGATTTAC TCGGCGACAT TGTAAAGGTC
        T  P  T     S  K  V  V     G  D  L     A  Q  F     M  V  S  N     K  L  T
2761  ACTCCCACCT CCAAGGTGGT CGGTGACTTG GCTCAGTTCA TGGTCTCGAA CAAACTGACT
        P  E  D     V  V  E  R     A  G  E     L  D  F     P  G  S  V     L  E  F
2821  CCAGAGGATG TTGTTGAGCG TGCTGGTGAG CTGGACTTCC CTGGTTCTGT GCTCGAATTC
        L  E  G     L  M  G  Q     P  F  G     G  F  P     E  P  L  R     S  R  A
2881  CTCGAAGGTC TCATGGGACA GCCCTTCGGT GGATTCCCCG AGCCATTGCG CTCCCGCGCC
        L  R  D     R  R  K  L     E  K  R     P  G  L     Y  L  E  P     L  D  L
2941  CTGCGCGATC GCCGCAAGCT CGAGAAGCGT CCAGGTCTCT ACCTCGAGCC TTTGGATTTG
        A  K  I     K  S  Q  I     R  E  K     F  G  A     A  T  E  Y     D  V  A
3001  GCTAAGATCA AGAGCCAGAT CCGTGAGAAG TTCGGTGCTG CTACTGAGTA TGACGTGGCC
        S  Y  A     M  Y  P  K     V  F  E     D  Y  K     K  F  V  Q     K  F  G
3061  AGCTATGCCA TGTATCCCAA GGTCTTCGAG GACTACAAGA AGTTCGTCCA GAAGTTCGGT
        D  L  S     V  L  P  T     R  Y  F     L  A  K     P  E  I  G     E  E  F
3121  GATCTCTCCG TCTTGCCCAC ACGGTACTTC TTGGCCAAGC CTGAGATTGG CGAGGAGTTC
        H  V  E     L  E  K  G     K  V  L     I  L  K     L  L  A  I     G  P  L
3181  CACGTTGAGC TGGAGAAGGG TAAGGTGCTC ATCCTGAAGT TGTTGGCCAT CGGCCCTCTT
        S  E  Q     T  G  Q  R     E  V  F     Y  E  V     N  G  E  V     R  Q  V
3241  TCAGAGCAGA CTGGTCAGCG TGAGGTCTTC TACGAAGTCA ACGGTGAGGT GCGCCAGGTC
        A  V  D     D  N  K  A     S  V  D     N  T  S     R  P  K  A     D  V  G
3301  GCTGTTGATG ACAACAAGGC TTCCGTGGAC AACACTTCAC GCCCTAAGGC CGATGTGGGT
        D  S  S     Q  V  G  A     P  M  S     G  V  V     V  E  I  R     V  H  D
3361  GACAGCAGCC AGGTCGGTGC TCCTATGAGC GGTGTGGTTG TTGAAATCCG TGTCCACGAT
        G  L  E     V  K  K  G     D  P  L     A  V  L     S  A  M  K     M
3421  GGTCTGGAGG TTAAGAAGGG TGACCCACTT GCCGTCCTGA GTGCCATGAA GATG*GTAAGT*
                                                                         E  M
3481  *TCATTCCGAA TCATTTTTCT CACTGGTCAA CTACAGATGC TAACAGCTTA TCCAG*GAAAT
        V  I  S     A  P  H     S  G  K  V     S  S  L     L  V  K     E  G  D  S
3541  GGTTATCTCT GCTCCTCACA GTGGAAAGGT CTCCAGCTTG CTGGTCAAGG AGGGCGATTC
        V  D  G     Q  D  L     V  C  K  I     V  K  A     *
3601  TGTGGATGGC CAGGATCTCG TCTGCAAGAT CGTCAAAGCG TAA
```

Fig. 9B

```
      M   S   D    K   A   R   E    A   V   S    Q   Y   L    K   Q   S    H   E   R   I
  1 ATGTCCGACA AGGCTCGCGA GGCGGTCTCG CAATATCTGA AGCAGTCTCA CGAGCGCATC
      F   E   N    N   R   A   W    V   A   A    K   K   E    D   P   A    F   F   E
 61 TTCGAGAACA ACCGCGCCTG GGTCGCGGCC AAGAAGGAAG AGGACCCCGC GTTTTTCGAG
      K   L   G    A   G   Q   T    P   Q   Y    L
121 AAACTGGGCG CCGGACAGAC GCCGCAATAT CTGTAAAGAC CAGCATCAGC GATTTGTCAT
                                                      Y    I   G   C   S
181 TGGAGTTGTC GGATGACTTT GCCATACTGA CCGTGGCTGT GCAGGTACAT CGGATGCAGT
      D   S   R    V   P   A   N    D   I   M    G   L   T    A   G   E    V   F   H
241 GACAGTCGCG TGCCCGCCAA TGACATTATG GGTCTCACGG CCGGCGAGGT CTTTGTGCAC
      R   N   I    A   N   L   V    P   N   T    D   L   N    V   M   S    V   I   N   Y
301 CGCAACATCG CCAATCTGGT GCCCAACACC GACCTCAATG TCATGTCGGT CATCAACTAC
      A   V   R    H   L   K   V    K   H   I    V   V   C    G   H   Y    N   C   G   G
361 GCCGTCCGGC ATCTGAAGGT CAAGCACATC GTTGTCTGCG GCCACTACAA CTGTGGCGGT
      V   K   A    L   T   P    S   D   L    G   L   L    N   P   W    R   N   V
421 GTCAAGGCTG CGCTGACGCC CTCCGACCTG GGCTGCTGA ACCCCTGGCT GCGCAATGTC
      R   D   V    Y   R   L    H   E   R   E    L   D   A    I   E   D    E   A   K
481 CGGGATGTGT ATCGGTTGCA CGAGCGCGAG CTGGACGCCA TCGAAGACGA AGAGGCGAAG
      Y   N   R    L   V   E   L    N   V   V    E   S   C    R   N   V    I   K   T   A
541 TATAATCGCC TGGTGGAGCT GAATGTTGTT GAGTCCTGCC GCAACGTCAT CAAGACGGCG
      A   V   Q    Q   S   Y    H   D   N   Q    F   P   V    H   G   W    I   F   D
601 GCGGTGCAGC AGAGCTACCA CGACAACCAG TTCCCCGTGG TCCACGGATG GATCTTTGAT
      V   R   T    G   L   L   R    D   L   N    I   D   F    E   E   T    L   R   D   I
661 GTGCGGACGG GTCTGCTTCG GGATCTCAAC ATTGATTTCG AGGAGACGCT GCGGGATATC
      K   K   I    Y   N   I   T    K   S   *
721 AAGAAGATCT ACAATATCAC CAAGAGCTGA
```

RECOMBINANT MICROORGANISMS FOR PRODUCTION C4-DICARBOXYLIC ACIDS

CROSS REFERENCE TO RELATED APPLICATIONS

This application claims priority benefit of U.S. Provisional Application No. 61/525,345, filed Aug. 19, 2011, the entire content of which is incorporated herein by reference.

REFERENCE TO A SEQUENCE LISTING

This application contains a Sequence Listing in computer readable form, which is incorporated herein by reference.

BACKGROUND

Organic acids have a long history of commercial use in a variety of industries. For example, organic acids are used in the food and feed industries (citric acid, ascorbic acid, lactic acid, acetic acid, and gluconic acid) as monomers for the production of various polymers (adipic acid, lactic acid, acrylic acid, and itaconic acid), as metal chelators (gluconic acid), and as "green" solvents (acetic acid) (Sauer et al., 2008, *Trends in Biotechnology* 26: 100-108). Organic acids may themselves be commercial products or they may be chemical building blocks used in the manufacture of other chemicals. In addition to specialty applications, it has long been recognized that C4-dicarboxylic acids can also serve as building block compounds for the production of large volume industrial chemicals, such as 1,4-butanediol, tetrahydrofuran, and gamma-butyrolactone.

Organic acids may be produced commercially either by chemical synthesis from petroleum derived feedstocks (e.g., fumaric acid, malic acid, acrylic acid, and adipic acid) or by microbial fermentation (e.g., citric acid, lactic acid, gluconic acid, and itaconic acid). Some organic acids—such as fumaric acid and malic acid—can also be produced by microbial fermentation, but are currently produced commercially by chemical synthesis from petrochemical feedstocks due to lower production costs. However, the rising cost of petroleum derived building block chemicals, the geopolitical instability affecting crude oil prices, and the desire to implement manufacturing processes that utilize feedstocks derived from renewable resources have stimulated a renewed interest in producing organic acids and other chemicals by microbial fermentation.

While C4-dicarboxylic acids such as malic acid are produced commercially today by chemical synthesis from petrochemical sources, it can also be produced by microbial fermentation. Malic acid has been produced at high levels in genetically engineered yeast (*Saccharomyces cerevisiae*) (Zelle et al., 2008, *Appl. Environ. Microbiol.* 74: 2766-2777) and naturally occurring filamentous fungi such as *Aspergillus* spp. (U.S. Pat. No. 3,063,910; Bercovitz et al., 1990, *Appl. Environ. Microbiol.* 56: 1594-1597). Abe et al. (U.S. Pat. No. 3,063,910) and Bercovitz et al. (1990, *Appl. Environ. Microbiol.* 56: 1594-1597) reported high levels of malic acid production in several species of *Aspergillus*. Moreover, Battat et al. (1991, *Biotechnol. Bioengineering,* 37: 1108-1116) reported malic acid production as high as 113 g/L by *Aspergillus flavus* in a stirred fermentor under optimized conditions. Dicarboxylic acid production by microbial fermentation in yeast is described in WO 2010/003728. Malic acid production by microbial fermentation is also described in WO 2009/011974, WO 2009/155382 and WO2010/111344. Improvement of the production of C4-dicarboxylic acids such as malic acid by genetic engineering may enable economical commercial malic acid production by fermentation.

Malic acid overproduction in a host such as *Aspergillus* spp. occurs under specific culture conditions (aerobic conditions and high C:N ratio; calcium carbonate may also added as a neutralizing agent and as source of $CO_2$ for malic acid biosynthesis). Under these conditions, overflow metabolism via the cytosolic, reductive tricarboxylic acid (TCA) cycle results in increased malic acid biosynthesis and secretion into the culture medium. Increased malic acid production has been reported in *Saccharomyces cerevisiae* by increasing the level of pyruvate carboxylase (Bauer et al., 1999, *FEMS Microbiol Lett.* 179: 107-113) or malate dehydrogenase (Pines et al., 1997, *Appl. Microbiol. Biotechnol.* 48: 248-255) using genetic engineering and increasing expression of a malic acid transporter (Zelle et al., 2008, supra). It has been suggested, based on biochemical evidence, that malate dehydrogenase activity is limiting malic acid production in *Aspergillus flavus* strain ATCC 13697 (Peleg et al., 1988, *Appl. Microbiol. Biotechnol.* 28: 69-75). WO 2011/028643, PCT/US11/38881, PCT/US11/38881, U.S. application Ser. Nos. 13/165,696 and 13/165,719, and U.S. Provisional Application No. 61/447,286—the contents of which are hereby incorporated by reference in their entireties—describe C4-dicarboxylic acid production.

It would be advantageous in the art to improve C4-dicarboxylic acid production, such as malic acid production, as a result of genetic engineering using recombinant DNA techniques. The present invention provides, inter alia, methods for improving C4-dicarboxylic acid production (e.g., malic acid production).

SUMMARY

Described herein are recombinant host cells comprising carbonic anhydrase activity, wherein the host cell produces (or is capable of producing) an increased amount of a C4-dicarboxylic acid (e.g., malic acid). In one aspect, the recombinant host cells comprises a heterologous polynucleotide encoding a carbonic anhydrase, wherein the host cell produces (or is capable of producing) and/or secretes (or is capable of secreting) a greater amount of C4-dicarboxylic acid compared to the host cell without the heterologous polynucleotide when cultivated under the same conditions. In some aspects, the carbonic anhydrase is a cytosolic carbonic anhydrase. In some aspects, the host cell further comprises a heterologous polynucleotide encoding a bicarbonate transporter, a heterologous polynucleotide encoding a C4-dicarboxylic acid transporter, a heterologous polynucleotide encoding a malate dehydrogenase, and/or a heterologous polynucleotide encoding a pyruvate carboxylase. In some aspects, the host cell is an *Aspergillus* host cell, such as an *Aspergillus oryzae* host cell.

Also described are methods of using recombinant host cells for the production of C4-dicarboxylic acids. In one aspect, a method of producing a C4-dicarboxylic acid (e.g., malic acid), comprises: (a) cultivating a recombinant host cell (e.g., an *Aspergillus* host cell) having carbonic anhydrase activity in a medium under suitable conditions to produce the C4-dicarboxylic acid; and (b) recovering the C4-dicarboxylic acid. In some aspects, the recombinant host cell comprises a heterologous polynucleotide encoding a carbonic anhydrase. In another aspect, a method of producing a C4-dicarboxylic acid (e.g., malic acid) comprises (a) transforming into a host cell (e.g., an *Aspergillus* host cell) a heterologous polynucleotides encoding a carbonic anhydrase described herein; (b) cultivating the transformed organism in a medium under suitable conditions to produce the C4-dicarboxylic acid; and (c) recovering the C4-dicarboxylic acid. In some aspects of the methods, the carbonic anhydrase is a cytosolic carbonic anhydrase. In some aspects of the methods, the recombinant host cell further comprises a heterologous polynucleotide encoding a bicarbonate transporter, a heterologous polynucleotide encoding a C4-dicarboxylic acid transporter, a heterologous polynucleotide encoding a malate dehydrogenase, and/or a heterologous polynucleotide encoding a pyruvate carboxylase. In some aspects of the methods, the host cell is an *Aspergillus* host cell, such as an *Aspergillus oryzae* host cell.

BRIEF DESCRIPTION OF THE FIGURES

FIGS. 3A and 3B show the genomic nucleotide construct sequence and the deduced amino acid sequence of an *Aspergillus oryzae* NRRL 3488 bicarbonate transporter gene (bt1) (SEQ ID NOs: 1 and 2, respectively).

FIGS. 4A and 4B show the genomic nucleotide construct sequence and the deduced amino acid sequence of an *Aspergillus oryzae* NRRL 3488 bicarbonate transporter gene (SEQ ID NOs: 3 and 4, respectively).

FIG. 6 shows the genomic DNA sequence and the deduced amino acid sequence of an *Aspergillus aculeatus* C4-dicarboxylic acid transporter gene (c4t521) (SEQ ID NOs: 5 and 6, respectively).

FIG. 7 shows the genomic DNA sequence and the deduced amino acid sequence of an *Aspergillus oryzae* NRRL 3488 malate dehydrogenase gene (mdh3) (SEQ ID NOs: 7 and 8, respectively).

FIGS. 9A and 9B together show the genomic DNA sequence and the deduced amino acid sequence of an *Aspergillus oryzae* NRRL 3488 pyruvate carboxylase gene (pyc) (SEQ ID NOs: 9 and 10, respectively).

FIG. 14 shows the genomic DNA sequence and the deduced amino acid sequence of an *Aspergillus aculeatus* carbonic anhydrase gene (ACLA_007930) (SEQ ID NOs: 54 and 55, respectively).

DEFINITIONS

Figure 1:
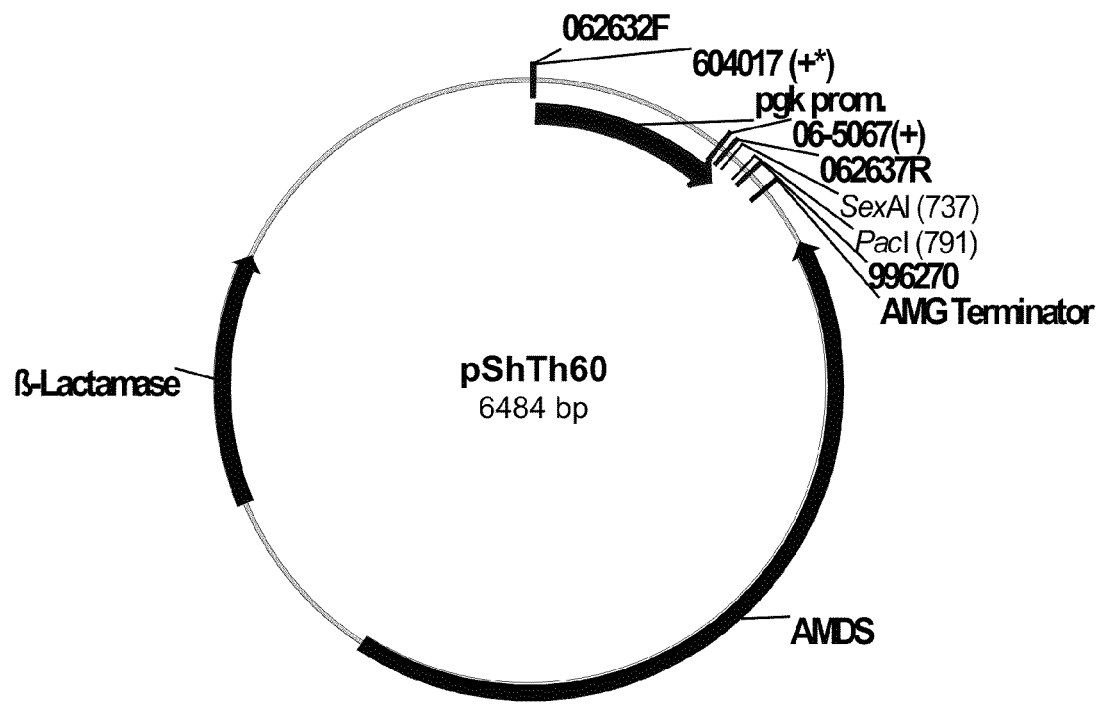
FIG. 1 shows a restriction map of pShTh60.

Carbonic anhydrase: The term "carbonic anhydrase" is defined herein as a zinc metalloenzyme that catalyzes the reaction of carbon dioxide ($CO_2$) and water ($H_2O$) to bicarbonate ($HCO_3^-$) (EC 4.2.1.1). Non-limiting classes of carbonic anhydrase proteins include the $\alpha$, $\beta$, $\gamma$, $\delta$ and $\epsilon$ families. Carbonic anhydrase activity can be determined from cell-free extracts as described in the art, e.g., as described in the art, e.g., in Khalifah, 1970, *J. Biol. Chem.*, 246: 2561-2573.

Cytosolic Carbonic anhydrase: The term "cytosolic carbonic anhydrase" means a carbonic anhydrase that does not contain a functional N-terminal mitochondrial target sequence (MTS). Non-limiting examples include a carbonic anhydrase that lacks an MTS, or a carbonic anhydrase that contains a modified but non-functional MTS (such as by truncation and/or sequence alteration). N-terminal MTS sequences their corresponding cleavage sites can be predicted using the programs MitoProtII-v1.101 and TargetP 1.1 as described in Elleuche, 2009, *Curr Genet*, 55, 211-222.

Bicarbonate transporter: The term "bicarbonate transporter" is defined herein as a protein—such as a membrane integrated protein—capable of facilitating the transfer of $HCO_3^-$ across a biological membrane, such as a cell membrane and/or the membrane of a cell organelle. Non-limiting classes of biocarbonate transporter proteins include the anion exchanger (AE) family of $Cl^-/HCO_3^-$ exchangers, the NBC family of $Na^+/HCO_3^-$ cotransporters, and the $Na^+$-dependent $Cl^-/HCO_3^-$ exchangers. In some aspects described herein, the bicarbonate transporter is a sulfate-bicarbonate transporter, wherein the transporter is capable of facilitating the transfer of both $HCO_3^-$ and $SO_4^{2-}$ anions across a biological membrane. Biocarbonate exchange activity can be determined from cell-free extracts as described in the art, e.g., as described in Sterling et al., 2002, *Am J Physiol Cell Physiol* 283: C1522-1529.

C4-dicarboxylic acid transporter: The term "C4-dicarboxylic acid transporter" is defined herein as a dicarboxylic acid permease that can transport malic acid, succinic acid, oxaloacetic acid, malonic acid, and/or fumaric acid outside a cell (Grobler et al., 1995, *Yeast* 11: 1485-1491; Camarasa et al., 2001, *Applied and Environmental Microbiology* 67: 4144-4151). A computational method to predict mitochondrially imported proteins and their targeting sequences is described by Claros and Vincens, 1996, *Eur. J. Biochem.* 241: 779-786.

Malate dehydrogenase: The term "malate dehydrogenase" is defined herein as a malate:$NAD^+$ oxidoreductase (EC 1.1.1.37) that catalyzes the reduction of oxaloacetate in the presence of $NADH+H^+$ to malate and $NAD^+$. For purposes of the present invention, malate dehydrogenase activity may be determined from cell-free extracts according to the following procedure. The assay solution consists of 1 mM oxaloacetic acid, 100 mM Tris pH 8.0, 10 mM $NaHCO_3$, 5 mM $MgCl_2$, and 0.1 mM NADH (Sigma Chemical Co., St. Louis, Mo., USA). The assay solution without oxaloacetic acid as substrate is run as a control to measure background NADH degradation rates. Dilutions of 1/100, 1/500, 1/2500, and 1/12500 of each supernatant are prepared with double-distilled water. Aliquots of 270 µl of the assay solution are dispensed into 96 well polystyrene flat bottom plates. A 30 µl sample of each diluted supernatant is added to initiate the assay. The reactions are monitored using a SPECTRAMAX® 340PC plate reader (Molecular Devices, Sunnyvale, Calif., USA) with the following settings: 340 nm, kinetic reading. A concentration series of NADH is used to construct a standard curve and a dilution series of purified malic dehydrogenase (Sigma Chemical Co., St. Louis, Mo., USA) is used as a positive control. One unit of malate dehydrogenase activity equals the amount of enzyme capable of converting 1 µmole of oxaloacetate and $NADH+H^+$ to malate and $NAD^+$ per minute at pH 8.0, 25° C.

Pyruvate carboxylase: The term "pyruvate carboxylase" is defined herein as a pyruvate:carbon-dioxide ligase (ADP-forming) (EC 6.4.1.1) that catalyzes the carboxylation of pyruvate in the presence of ATP and $HCO_3^-$ to oxaloacetate, ADP, and phosphate. For purposes of the present invention, pyruvate carboxylase activity may be determined from cell-free extracts according to the procedure of the SIGMA® Quality Control Test procedure for pyruvate carboxylase (Sigma Chemical Co., St. Louis, Mo., USA) substituting Tris buffer at pH 8.0. One unit of pyruvate carboxylase activity equals the amount of enzyme capable of converting 1 µmole of pyruvate and $CO_2$ to oxaloacetate per minute at pH 7.8, 30° C.

Heterologous polynucleotide: The term "heterologous polynucleotide" is defined herein as a polynucleotide that is not native to the host cell; a native polynucleotide in which one or more (e.g., two, several) structural modifications have been made to the coding region; a native polynucleotide whose expression is quantitatively altered as a result of manipulation of the DNA by recombinant DNA techniques, e.g., a different (foreign) promoter linked to the polynucleotide; or a native polynucleotide whose expression is quantitatively altered by the introduction of one or more extra copies of the polynucleotide into the host cell.

Coding sequence: The term "coding sequence" means a polynucleotide sequence, which specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a sequence of genomic DNA, cDNA, a synthetic polynucleotide, and/or a recombinant polynucleotide.

cDNA sequence: The term "cDNA sequence" means a sequence of DNA following reverse transcription from a mature, spliced, mRNA molecule obtained from a eukaryotic cell. The initial, primary RNA transcript from genomic DNA is a precursor to mRNA that is processed through a series of steps, including splicing, before appearing as mature spliced mRNA. A cDNA sequence lacks intervening intron sequences that may be present in the corresponding genomic DNA sequence. Accordingly, the phrase "the cDNA sequence of SEQ ID NO: X" intends the resulting sequence after the intervening intron sequences of SEQ ID NO: X, if present, are removed. In some instances—when a referenced genomic DNA sequence lacks intervening intron sequences—a cDNA sequence may be identical to its corresponding genomic DNA sequence.

Genomic DNA sequence: The term "genomic DNA sequence" means a DNA sequence found in the genome of a source organism (e.g., a eukaryotic or prokaryotic genome). In some instances, a genomic DNA sequence from a eukaryotic genome contains one or more intervening intron sequences that are removed from the primary RNA transcript as a result of RNA splicing. Accordingly, the phrase "the genomic DNA sequence of SEQ ID NO: Y" intends the corresponding DNA sequence from the source organism which includes intervening intron sequences, if any, that are present before RNA splicing.

Mature polypeptide sequence: The term "mature polypeptide sequence" means the portion of the referenced polypeptide sequence after any post-translational sequence modifications (such as N-terminal processing and/or C-terminal truncation). The mature polypeptide sequence may be predicted, e.g., based on the SignalP program (Nielsen et al., 1997, *Protein Engineering* 10:1-6) or the InterProScan program (The European Bioinformatics Institute). In some instances, the mature polypeptide sequence may be identical to the entire referenced polypeptide sequence. It is known in the art that a host cell may produce a mixture of two of more different mature polypeptide sequences (i.e., with a different C-terminal and/or N-terminal amino acid) expressed by the same polynucleotide.

Fragment: The term "fragment" means a polypeptide having one or more (e.g., two, several) amino acids deleted from the amino and/or carboxyl terminus of a referenced polypeptide sequence. In one aspect, the fragment has carbonic anhydrase, bicarbonate transporter, C4-dicarboxylic acid transporter, malate dehydrogenase, or pyruvate carboxylase activity. In another aspect, the number of amino acid residues in the fragment is at least 75%, e.g., at least 80%, 85%, 90%, or 95% of any carbonic anhydrase, bicarbonate transporter, C4-dicarboxylic acid transporter, malate dehydrogenase, or pyruvate carboxylase described herein, e.g., at least 75%, e.g., at least 80%, 85%, 90%, or 95% of the number of amino acid residues in SEQ ID NOs: 2, 4, 6, 8, 10, 27, 29, 32, 34, 36, 39, 41, 43, 45, or 55.

Subsequence: The term "subsequence" means a polynucleotide having one or more (e.g., two, several) nucleotides deleted from the 5' and/or 3' end of the referenced nucleotide sequence. In one aspect, the subsequence encodes a fragment having carbonic anhydrase, bicarbonate transporter, C4-dicarboxylic acid transporter, malate dehydrogenase, or pyruvate carboxylase activity. In another aspect, the number of nucleotides residues in the subsequence is at least 75%, e.g., at least 80%, 85%, 90%, or 95% of the number of nucleotide residues in any sequence encoding a carbonic anhydrase, bicarbonate transporter, C4-dicarboxylic acid transporter, malate dehydrogenase, or pyruvate carboxylase described herein, e.g., at least 75%, e.g., at least 80%, 85%, 90%, or 95% of the number of nucleotide residues in SEQ ID NOs: 1, 3, 5, 7, 9, 26, 28, 30, 31, 33, 35, 37, 38, 40, 42, 44, or 54.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Sequence Identity: The relatedness between two amino acid sequences or between two nucleotide sequences is described by the parameter "sequence identity".

For purposes described herein, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

$$(\text{Identical Residues} \times 100)/(\text{Length of Alignment} - \text{Total Number of Gaps in Alignment})$$

For purposes described herein, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

$$(\text{Identical Deoxyribonucleotides} \times 100)/(\text{Length of Alignment} - \text{Total Number of Gaps in Alignment})$$

Expression: The term "expression" includes any step involved in the production of the polypeptide including, but not limited to, transcription, post-transcriptional modification, translation, post-translational modification, and secretion. Expression can be measured—for example, to detect increased expression—by techniques known in the art, such as measuring levels of mRNA and/or translated polypeptide.

Nucleic acid construct: The term "nucleic acid construct" means a polynucleotide comprises one or more (e.g., two, several) control sequences. The polynucleotide may be single-stranded or double-stranded, and may be isolated from a naturally occurring gene, modified to contain segments of nucleic acids in a manner that would not otherwise exist in nature, or synthetic.

Control sequence: The term "control sequence" means a nucleic acid sequence necessary for polypeptide expression. Control sequences may be native or foreign to the polynucleotide encoding the polypeptide, and native or foreign to each other. Such control sequences include, but are not limited to, a leader sequence, polyadenylation sequence, propeptide sequence, promoter sequence, signal peptide sequence, and transcription terminator sequence. The control sequences may be provided with linkers for the purpose of introducing specific restriction sites facilitating ligation of the control sequences with the coding region of the polynucleotide encoding a polypeptide.

Operably linked: The term "operably linked" means a configuration in which a control sequence is placed at an appropriate position relative to the coding sequence of a polynucleotide such that the control sequence directs the expression of the coding sequence.

Expression vector: The term "expression vector" means a linear or circular DNA molecule that comprises a polynucleotide encoding a polypeptide and is operably linked to control sequences, wherein the control sequences provide for expression of the polynucleotide encoding the polypeptide. At a minimum, the expression vector comprises a promoter sequence, and transcriptional and translational stop signal sequences.

Host cell: The term "host cell" means any cell type that is susceptible to transformation, transfection, transduction, and the like with a nucleic acid construct or expression vector comprising one or more (e.g., two, several) polynucleotides described herein (e.g., a polynucleotide encoding a carbonic anhydrase). The term "host cell" encompasses any progeny of a parent cell that is not identical to the parent cell due to mutations that occur during replication.

Disruption: The term "disruption" means that a promoter, coding region, and/or terminator of a polynucleotide encoding a polypeptide having enzyme activity within a host cell is partially or entirely modified (such as by modification, deletion, insertion, and/or substitution of one or more nucleotides) resulting in the absence or decrease of said enzyme activity of the host cell. The absence or decrease of enzyme activity can be measured directly by techniques known in the art (such as cell-free extract measurements referenced herein); or by the absence or decrease of corresponding mRNA (e.g., at least 50% decrease, at least 60% decrease, at least 70% decrease, at least 80% decrease, or at least 90% decrease); the absence or decrease in the amount of corresponding polypeptide having enzyme activity (e.g., at least 50% decrease, at least 60% decrease, at least 70% decrease, at least 80% decrease, or at least 90% decrease); or the absence or decrease of the specific activity of the corresponding polypeptide having enzyme activity (e.g., at least 50% decrease, at least 60% decrease, at least 70% decrease, at least 80% decrease, or at least 90% decrease) if present. Disruptions of a particular gene of interest can be generated by methods known in the art, e.g., by directed homologous recombination (see *Methods in Yeast Genetics* (1997 edition), Adams, Gottschling, Kaiser, and Stems, Cold Spring Harbor Press (1998)); or by RNAi or antisense technology.

Volumetric productivity: The term "volumetric productivity" refers to the amount of referenced product produced (e.g., the amount of C4-dicarboxylic acid produced) per volume of the system used (e.g., the total volume of media and contents therein) per unit of time.

Fermentable medium: The term "fermentable medium" refers to a medium comprising one or more (e.g., two, several) sugars, such as glucose, fructose, sucrose, cellobiose, xylose, xylulose, arabinose, mannose, galactose, and/or soluble oligosaccharides, wherein the medium is capable, in part, of being converted (fermented) by a host cell into a desired product, such as C4-dicarboxylic acid. In some instances, the fermentation medium is derived from a natural source, such as sugar cane, starch, or cellulose, and may be the result of pretreating the source by enzymatic hydrolysis (saccharification).

Reference to "about" a value or parameter herein includes aspects that are directed to that value or parameter per se. For example, description referring to "about X" includes the aspect "X". When used in combination with measured values, "about" includes a range that encompasses at least the uncertainty associated with the method of measuring the particular value, and can include a range of plus or minus two standard deviations around the stated value.

As used herein and in the appended claims, the singular forms "a," "or," and "the" include plural referents unless the context clearly dictates otherwise. It is understood that the aspects described herein include "consisting" and/or "consisting essentially of" aspects.

Unless defined otherwise or clearly indicated by context, all technical and scientific terms used herein have the same meaning as commonly understood by one of ordinary skill in the art.

DETAILED DESCRIPTION

Described herein, inter alia, is the increased expression of specific genes in a recombinant host cell, such as a filamentous fungus (e.g., *Aspergillus*) to enhance the production of C4-dicarboxylic acids (e.g., malic acid). In some aspects, the host cell comprises a heterologous polynucleotide for the expression of a carbonic anhydrase. In one aspect, the carbonic anhydrase is overexpressed under culture conditions to produce C4-dicarboxylic acid in high titers. The recombinant host cell may further comprise a heterologous polynucleotide encoding a bicarbonate transporter, a heterologous polynucleotide encoding a C4-dicarboxylic acid transporter, a heterologous polynucleotide encoding a malate dehydrogenase, and/or a heterologous polynucleotide encoding a pyruvate carboxylase.

Carbonic Anhydrases and Polynucleotides Encoding Carbonic Anhydrases

In some aspects of the recombinant host cells and methods described herein, the host cells have carbonic anhydrase activity. The carbonic anhydrase can be any carbonic anhydrase that is suitable for the host cells and their methods of use described herein, such as a naturally occurring carbonic anhydrase or a variant thereof that retains carbonic anhydrase activity. In one aspect, the carbonic anhydrase is present in the cytosol of the host cells. In some aspects, the carbonic anhydrase is a cytosolic carbonic anhydrase, as defined herein. In some aspects, the host cells comprise one or more (e.g., two, several) heterologous polynucleotides that encode a carbonic anhydrase.

In some aspects, the host cells comprising the one or more (e.g., two, several) heterologous polynucleotides that encode a carbonic anhydrase have an increased level of carbonic anhydrase activity compared to the host cells without the one or more polynucleotides that encode a carbonic anhydrase, when cultivated under the same conditions. In some aspects, the host cells comprising the one or more heterologous polynucleotides that encode a carbonic anhydrase have an increased level of carbonic anhydrase activity of at least 5%, e.g., at least 10%, at least 15%, at least 20%, at least 25%, at least 50%, at least 100%, at least 150%, at least 200%, at least 300%, or at 500% compared to the host cells without the one or more polynucleotides that encode a carbonic anhydrase, when cultivated under the same conditions.

In some aspects, the host cell comprises a heterologous polynucleotide that encodes a carbonic anhydrase. In one aspect, the heterologous polynucleotide that encodes a carbonic anhydrase is selected from: (a) a polynucleotide that encodes a carbonic anhydrase having at least 65% sequence identity to SEQ ID NO: 55; (b) a polynucleotide that hybridizes under low stringency conditions with (i) SEQ ID NO: 54, (ii) the cDNA sequence of SEQ ID NO: 54, or (iii) the full-length complementary strand of (i) or (ii); and (c) a polynucleotide that has at least 65% sequence identity to SEQ ID NO: 54, or the cDNA sequence of SEQ ID NO: 54. As can be appreciated by one of skill in the art, in some instances the heterologous polynucleotide that encodes a carbonic anhydrase may qualify under more than one of the selections (a), (b) and (c) noted above.

In one aspect, the heterologous polynucleotide encodes a carbonic anhydrase having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 55. In one aspect, the carbonic anhydrase sequence differs by no more than ten amino acids, e.g., by no more than five amino acids, by no more than four amino acids, by no more than three amino acids, by no more than two amino acids, or by one amino acid from SEQ ID NO: 55.

In one aspect, the carbonic anhydrase comprises or consists of the amino acid sequence of SEQ ID NO: 55, an allelic variant thereof, or a fragment of the foregoing having carbonic anhydrase activity. In another aspect, the carbonic anhydrase comprises or consists of the amino acid sequence of SEQ ID NO: 55. In another aspect, the carbonic anhydrase comprises or consists of amino acids 1 to 225 of SEQ ID NO: 55.

In one aspect, the heterologous polynucleotide encodes a carbonic anhydrase having an amino acid substitution, deletion, and/or insertion of one or more (e.g., two, several) amino acids of SEQ ID NO: 55. An amino acid substitution means that an amino acid corresponding to a position of the referenced sequence is different; an amino acid deletion means that an amino acid corresponding to a position of the referenced sequence is not present; and an amino acid insertion means that an amino acid is present that is not present at a corresponding position of the referenced sequence. In some of these aspects, the total number of amino acid substitutions, deletions and/or insertions of SEQ ID NO: 55 is not more than 10, e.g., not more than 9, 8, 7, 6, 5, 4, 3, 2, or 1.

The amino acid changes are generally of a minor nature, that is conservative amino acid substitutions or insertions that do not significantly affect the folding and/or activity of the protein; small deletions, typically of one to about 30 amino acids; small amino-terminal or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the carbonic anhydrase, alter the substrate specificity, change the pH optimum, and the like.

Essential amino acids in a carbonic anhydrase can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for carbonic anhydrase activity to identify amino acid residues that are critical to the activity of the molecule. See also, Hilton et al., 1996, J. Biol. Chem. 271: 4699-4708. The active site of the carbonic anhydrase or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identities of essential amino acids can also be inferred from analysis of identities with other carbonic anhydrase that are related to the referenced carbonic anhydrase.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active carbonic anhydrases can be recovered from the host cells and rapidly sequenced using standard methods in the art. These methods allow the rapid determination of the importance of individual amino acid residues in a polypeptide.

In one aspect, the heterologous polynucleotide that encodes a carbonic anhydrase hybridizes under at least low stringency conditions, e.g., medium stringency conditions, medium-high stringency conditions, high stringency conditions, or very high stringency conditions with (i) SEQ ID NO: 54, (ii) the cDNA sequence of SEQ ID NO: 54, or (iii) the full-length complementary strand of (i) or (ii) (see, e.g., J. Sambrook, E. F. Fritsch, and T. Maniatus, 1989, *Molecular Cloning, A Laboratory Manual*, 2d edition, Cold Spring Harbor, N.Y.). In one aspect, the heterologous polynucleotide that encodes a carbonic anhydrase hybridizes under at least low stringency conditions, e.g., medium stringency conditions, medium-high stringency conditions, high stringency conditions, or very high stringency conditions with SEQ ID NO: 54, or the full-length complementary strand thereof. In another aspect, the heterologous polynucleotide that encodes a carbonic anhydrase hybridizes under at least low stringency conditions, e.g., medium stringency conditions, medium-high stringency conditions, high stringency conditions, or very high stringency conditions with the cDNA sequence of SEQ ID NO: 54, or the full-length complementary strand thereof.

In one aspect, the heterologous polynucleotide that encodes a carbonic anhydrase has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 54 or the cDNA sequence of SEQ ID NO: 54. In one aspect, the heterologous polynucleotide that encodes a carbonic anhydrase has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 54. In another aspect, the heterologous polynucleotide that encodes a carbonic anhydrase has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to the cDNA sequence of SEQ ID NO: 54.

In one aspect, the heterologous polynucleotide that encodes a carbonic anhydrase comprises SEQ ID NO: 54. In one aspect, the heterologous polynucleotide comprises nucleotides 1 to 750 of SEQ ID NO: 54. In one aspect, the heterologous polynucleotide comprises a subsequence of SEQ ID NO: 54, wherein the subsequence encodes a polypeptide having carbonic anhydrase activity. In one aspect, the number of nucleotides residues in the subsequence is at least 75%, e.g., at least 80%, 85%, 90%, or 95% of the number of nucleotide residues in SEQ ID NO: 54. In one aspect, the heterologous polynucleotide encodes a fragment of SEQ ID NO: 55, wherein the fragment has carbonic anhydrase activity. In one aspect, the number of amino acid residues in the fragment is at least 75%, e.g., at least 80%, 85%, 90%, or 95% of the number of amino acid residues in SEQ ID NO: 55.

The carbonic anhydrase may be a fused polypeptide or cleavable fusion polypeptide in which another polypeptide is fused at the N-terminus or the C-terminus of the carbonic anhydrase. A fused polypeptide may be produced by fusing a polynucleotide encoding another polypeptide to a polynucleotide encoding the carbonic anhydrase. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Techniques used to isolate or clone a polynucleotide—such as a polynucleotide encoding a carbonic anhydrase—as well as any other polypeptide used in any of the aspects mentioned herein, are known in the art and include isolation from genomic DNA, preparation from cDNA, or a combination thereof. The cloning of the polynucleotides from such genomic DNA can be effected, e.g., by using the well known polymerase chain reaction (PCR) or antibody screening of expression libraries to detect cloned DNA fragments with shares structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Aspergillus*, or another or related organism, and thus, for example, may be an allelic or species variant of the polypeptide encoding region of the nucleotide sequence.

The polynucleotide of SEQ ID NO: 54, or a subsequence thereof; as well as the amino acid sequence of SEQ ID NO: 55; or a fragment thereof; may be used to design nucleic acid probes to identify and clone a carbonic anhydrase from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, e.g., at least 14 nucleotides, at least 25 nucleotides, at least 35 nucleotides, at least 70 nucleotides in lengths. The probes may be longer, e.g., at least 100 nucleotides, at least 200 nucleotides, at least 300 nucleotides, at least 400 nucleotides, at least 500 nucleotides in lengths. Even longer probes may be used, e.g., at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin).

A genomic DNA or cDNA library prepared from such other strains may be screened for DNA that hybridizes with the probes described above and encodes a polypeptide having carbonic anhydrase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 54, or a subsequence thereof, the carrier material may be used in a Southern blot.

For purposes of the probes described above, hybridization indicates that the polynucleotide hybridizes to a labeled nucleic acid probe corresponding to SEQ ID NO: 54, the full-length complementary strand thereof, or a subsequence of the foregoing; under very low to very high stringency conditions. Molecules to which the nucleic acid probe hybridizes under these conditions can be detected using, for example, X-ray film.

In one aspect, the nucleic acid probe is SEQ ID NO: 54. In another aspect, the nucleic acid probe is a polynucleotide that encodes the polypeptide of SEQ ID NO: 55, or a fragment thereof.

For long probes of at least 100 nucleotides in length, very low to very high stringency conditions are defined as prehybridization and hybridization at 42° C. in 5×SSPE, 0.3% SDS, 200 micrograms/mL sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° C. (very low stringency), at 50° C. (low stringency), at 55° C. (medium stringency), at 60° C. (medium-high stringency), at 65° C. (high stringency), and at 70° C. (very high stringency).

For short probes of about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Acad. Sci. USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per mL following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

Polynucleotides encoding the carbonic anhydrase described herein may be obtained from a microorganism of any genus. As used herein, the term "obtained from" in connection with a given source shall mean that the polypeptide encoded by a polynucleotide is produced by the source or by a cell in which the polynucleotide from the source has been inserted.

The carbonic anhydrase may be a bacterial carbonic anhydrase. For example, the carbonic anhydrase may be a Gram-positive bacterial carbonic anhydrase such as a *Bacillus, Streptococcus, Streptomyces, Staphylococcus, Enterococcus, Lactobacillus, Lactococcus, Clostridium, Geobacillus,* or *Oceanobacillus* carbonic anhydrase, or a Gram-negative bacterial carbonic anhydrase such as an *E. coli, Pseudomonas, Salmonella, Campylobacter, Helicobacter, Flavobacterium, Fusobacterium, Ilyobacter, Neisseria,* or *Ureaplasma* carbonic anhydrase.

In one aspect, the carbonic anhydrase is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* carbonic anhydrase.

In another aspect, the carbonic anhydrase is a *Streptococcus equisimilis, Streptococcus pyogenes, Streptococcus uberis,* or *Streptococcus equi* subsp. *Zooepidemicus* carbonic anhydrase. In another aspect, the carbonic anhydrase is a *Streptomyces achromogenes, Streptomyces avermitilis, Streptomyces coelicolor, Streptomyces griseus,* or *Streptomyces lividans* carbonic anhydrase.

The carbonic anhydrase may be a fungal carbonic anhydrase. In one aspect, the fungal carbonic anhydrase is a yeast carbonic anhydrase such as a *Candida, Kluyveromyces, Pichia, Saccharomyces, Schizosaccharomyces,* or *Yarrowia* carbonic anhydrase.

In another aspect, the fungal carbonic anhydrase is a filamentous fungal carbonic anhydrase such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* carbonic anhydrase.

In another aspect, the carbonic anhydrase is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* carbonic anhydrase.

In another aspect, the carbonic anhydrase is an *Acremonium cellulolyticus, Aspergillus aculeatus, Aspergillus awamori, Aspergillus flavus, Aspergillus fumigatus, Aspergillus foetidus, Aspergillus japonicus, Aspergillus nidulans, Aspergillus niger, Aspergillus oryzae, Aspergillus sojae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei,* or *Trichoderma viride* carbonic anhydrase.

In another aspect, the carbonic anhydrase is an *Aspergillus* carbonic anhydrase, such as the *Aspergillus clavatus* carbonic anhydrase of SEQ ID NO: 55.

It will be understood that for the aforementioned species, both the perfect and imperfect states, and other taxonomic equivalents, e.g., anamorphs, are encompassed regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

In some aspects, the carbonic anhydrase has at least 20%, e.g., at least 40%, at least 50%, at least 60%, at least 70%, at least 80%, at least 90%, at least 95%, at least 96%, at least 97%, at least 98%, at least 99%, or 100% of the carbonic anhydrase activity of the mature polypeptide of SEQ ID NO: 55 under the same conditions.

The carbonic anhydrase may also be identified and obtained from other sources including microorganisms isolated from nature (e.g., soil, composts, water, silage, etc.) or DNA samples obtained directly from natural materials (e.g., soil, composts, water, silage, etc.) using the above-mentioned probes. Techniques for isolating microorganisms and DNA directly from natural habitats are well known in the art. The polynucleotide encoding a carbonic anhydrase may then be derived by similarly screening a genomic or cDNA library of another microorganism or mixed DNA sample. Once a polynucleotide encoding a carbonic anhydrase has been detected with suitable probe(s) as described herein, the sequence may be isolated or cloned by utilizing techniques that are known to those of ordinary skill in the art (see, e.g., J. Sambrook, E. F. Fritsch, and T. Maniatus, 1989, *Molecular Cloning, A Laboratory Manual,* 2d edition, Cold Spring Harbor, N.Y.).

Bicarbonate Transporters and Polynucleotides Encoding Bicarbonate Transporters

In some aspects of the recombinant host cells and methods described herein, the host cells have bicarbonate transporter activity. The bicarbonate transporter can be any bicarbonate transporter that is suitable for the host cells and their methods of use described herein, such as a naturally occurring bicarbonate transporter or a variant thereof that retains bicarbonate transporter activity. In one aspect, the bicarbonate transporter is present in the cytosol of the host cells. In some aspects, the host cells comprise one or more (e.g., two, several) heterologous polynucleotides that encode a bicarbonate transporter.

In some aspects, the host cells comprising the one or more (e.g., two, several) heterologous polynucleotides that encode a bicarbonate transporter have an increased level of bicarbonate transporter activity compared to the host cells without the one or more polynucleotides that encode a bicarbonate transporter, when cultivated under the same conditions. In some aspects, the host cells comprising the one or more heterologous polynucleotides that encode a bicarbonate transporter have an increased level of bicarbonate transporter activity of at least 5%, e.g., at least 10%, at least 15%, at least 20%, at least 25%, at least 50%, at least 100%, at least 150%, at least 200%, at least 300%, or at 500% compared to the host cells without the one or more polynucleotides that encode a bicarbonate transporter, when cultivated under the same conditions.

In some aspects, the host cell comprises a heterologous polynucleotide that encodes a bicarbonate transporter. In one aspect, the heterologous polynucleotide that encodes a bicarbonate transporter is selected from: (a) a polynucleotide that encodes a bicarbonate transporter having at least 65% sequence identity to SEQ ID NO: 2 or 4; (b) a polynucleotide that hybridizes under low stringency conditions with (i) SEQ ID NO: 1 or 3, (ii) the cDNA sequence of SEQ ID NO: 1 or 3, or (iii) the full-length complementary strand of (i) or (ii); and (c) a polynucleotide that has at least 65% sequence identity to SEQ ID NO: 1 or 3, or the cDNA sequence of SEQ ID NO: 1 or 3. As can be appreciated by one of skill in the art, in some instances the heterologous polynucleotide that encodes a bicarbonate transporter may qualify under more than one of the selections (a), (b) and (c) noted above.

In one aspect, the heterologous polynucleotide encodes a bicarbonate transporter having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 2 or 4. In one aspect, the bicarbonate transporter sequence differs by no more than ten amino acids, e.g., by no more than five amino acids, by no more than four amino acids, by no more than three amino acids, by no more than two amino acids, or by one amino acid from SEQ ID NO: 2 or 4.

In one aspect, the bicarbonate transporter comprises or consists of the amino acid sequence of SEQ ID NO: 2 or 4, an allelic variant thereof, or a fragment of the foregoing having bicarbonate transporter activity. In another aspect, the bicarbonate transporter comprises or consists of the amino acid sequence of SEQ ID NO: 2 or 4. In another aspect, the bicarbonate transporter comprises or consists of amino acids 1 to 770 of SEQ ID NO: 2 or amino acids 1 to 843 of SEQ ID NO:4.

In one aspect, the heterologous polynucleotide encodes a bicarbonate transporter having an amino acid substitution, deletion, and/or insertion of one or more (e.g., two, several) amino acids of SEQ ID NO: 2 or 4, as described supra. In some aspects, the total number of amino acid substitutions, deletions and/or insertions of SEQ ID NO: 2 or 4, is not more than 10, e.g., not more than 9, 8, 7, 6, 5, 4, 3, 2, or 1.

In one aspect, the heterologous polynucleotide that encodes a bicarbonate transporter hybridizes under at least low stringency conditions, e.g., medium stringency conditions, medium-high stringency conditions, high stringency conditions, or very high stringency conditions with (i) SEQ ID NO: 1 or 3, (ii) the cDNA sequence of SEQ ID NO: 1 or 3, or (iii) the full-length complementary strand of (i) or (ii) (see, e.g., J. Sambrook, E. F. Fritsch, and T. Maniatus, 1989, supra). In one aspect, the heterologous polynucleotide that encodes a bicarbonate transporter hybridizes under at least low stringency conditions, e.g., medium stringency conditions, medium-high stringency conditions, high stringency conditions, or very high stringency conditions with SEQ ID NO: 1 or 3, or the full-length complementary strand thereof. In one aspect, the heterologous polynucleotide that encodes a bicarbonate transporter hybridizes under at least low stringency conditions, e.g., medium stringency conditions, medium-high stringency conditions, high stringency conditions, or very high stringency conditions with the cDNA sequence of SEQ ID NO: 1 or 3, or the full-length complementary strand thereof.

In one aspect, the heterologous polynucleotide that encodes a bicarbonate transporter has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 1 or 3, or the cDNA sequence of SEQ ID NO: 1 or 3. In one aspect, the heterologous polynucleotide that encodes a bicarbonate transporter has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 1 or 3. In one aspect, the heterologous polynucleotide that encodes a bicarbonate transporter has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to the cDNA sequence of SEQ ID NO: 1 or 3.

In one aspect, the heterologous polynucleotide that encodes a bicarbonate transporter comprises SEQ ID NO: 1 or 3. In one aspect, the heterologous polynucleotide comprises nucleotides 1 to 2503 of SEQ ID NO: 1, or nucleotides 1 to 2657 of SEQ ID NO: 3. In one aspect, the heterologous polynucleotide comprises a subsequence of SEQ ID NO: 1 or 3, wherein the subsequence encodes a polypeptide having bicarbonate transporter activity. In one aspect, the number of nucleotides residues in the subsequence is at least 75%, e.g., at least 80%, 85%, 90%, or 95% of the number of nucleotide residues in SEQ ID NO: 1 or 3.

In one aspect, the heterologous polynucleotide encodes a fragment of SEQ ID NO: 2 or 4, wherein the fragment has bicarbonate transporter activity. In one aspect, the number of amino acid residues in the fragment is at least 75%, e.g., at least 80%, 85%, 90%, or 95% of the number of amino acid residues in SEQ ID NO: 2 or 4. In one aspect, the fragment contains a bicarbonate transporter domain, e.g., the putative bicarbonate transporter domain of amino acids 280 to 556 of SEQ ID NO: 2 or 192 to 480 of SEQ ID NO: 4.

The bicarbonate transporter may also be an allelic variant or artificial variant of a bicarbonate transporter.

The bicarbonate transporter can also include fused polypeptides or cleavable fusion polypeptides, as described supra.

Techniques used to isolate or clone a polynucleotide encoding a bicarbonate transporter are described supra.

The polynucleotide sequence of SEQ ID NO: 1, 3, or a subsequence thereof; as well as the amino acid sequence of SEQ ID NO: 2, 4, or a fragment thereof; may be used to design nucleic acid probes to identify and clone DNA encoding a bicarbonate transporter from strains of different genera or species, as described supra. A genomic DNA or cDNA library prepared from such other organisms may be screened for DNA that hybridizes with the probes described above and encodes a bicarbonate transporter, as described supra.

In one aspect, the nucleic acid probe is SEQ ID NO: 1 or 3. In another aspect, the nucleic acid probe is a polynucleotide sequence that encodes SEQ ID NO: 2 or 4, or a fragment thereof.

For long probes of at least 100 nucleotides in length, very low to very high stringency and washing conditions are defined as described supra. For short probes of about 15 nucleotides to about 70 nucleotides in length, stringency and washing conditions are defined as described supra.

Polynucleotides encoding the bicarbonate transporter may be obtained from microorganisms of any genus. In one aspect, the bicarbonate transporter may be a bacterial, a yeast, or a filamentous fungal bicarbonate transporter obtained from the microorganisms described herein. In another aspect, the bicarbonate transporter is an *Aspergillus* bicarbonate transporter, such as the *Aspergillus oryzae* bicarbonate transporter of SEQ ID NO: 2 or 4.

Other bicarbonate transporters that can be used with the host cells and methods of use described herein include, but are not limited to, a *H. sapiens* SLC4A1 bicarbonate transporter (SEQ ID NO: 53 of WO2010/111344, wherein said sequence is incorporated by reference), an *O. cuniculus* SLC4A8 bicarbonate transporter (SEQ ID NO: 54 of WO2010/111344, wherein said sequence is incorporated by reference), and an *S. cerevisiae* YNL275w bicarbonate transporter (SEQ ID NO: 55 of WO2010/111344, wherein said sequence is incorporated by reference). Any aspect described herein related to sequence identity, hybridization, amino acid modifications (e.g., substitutions, deletions, and/or insertions), fragments or subsequences thereof is embraced for the bicarbonate transporters above.

In some aspects, the bicarbonate transporter has at least 20%, e.g., at least 40%, at least 50%, at least 60%, at least 70%, at least 80%, at least 90%, at least 95%, at least 96%, at least 97%, at least 98%, at least 99%, or 100% of the bicarbonate transporter activity of the mature polypeptide of SEQ ID NO: 2 or 4 under the same conditions.

The bicarbonate transporter may also be identified and obtained from other sources including microorganisms isolated from nature (e.g., soil, composts, water, silage, etc.) or DNA samples obtained directly from natural materials (e.g., soil, composts, water, silage, etc.) as described supra.

C4-Dicarboxylic Acid Transporters and Polynucleotides Encoding C4-Dicarboxylic Acid Transporters In some aspects of the recombinant host cells and methods described herein, the host cells have C4-dicarboxylic acid transporter activity. The C4-dicarboxylic acid transporter can be any C4-dicarboxylic acid transporter that is suitable for the host cells and their methods of use described herein, such as a naturally occurring C4-dicarboxylic acid transporter or a variant thereof that retains C4-dicarboxylic acid transporter activity. In one aspect, the C4-dicarboxylic acid transporter is present in the cytosol of the host cells. In some aspects, the host cells comprise one or more (e.g., two, several) heterologous polynucleotides that encode a C4-dicarboxylic acid transporter.

In some aspects, the host cells comprising the one or more (e.g., two, several) heterologous polynucleotides that encode a C4-dicarboxylic acid transporter have an increased level of C4-dicarboxylic acid transporter activity compared to the host cells without the one or more polynucleotides that encode a C4-dicarboxylic acid transporter, when cultivated under the same conditions. In some aspects, the host cells comprising the one or more heterologous polynucleotides that encode a C4-dicarboxylic acid transporter have an increased level of C4-dicarboxylic acid transporter activity of at least 5%, e.g., at least 10%, at least 15%, at least 20%, at least 25%, at least 50%, at least 100%, at least 150%, at least 200%, at least 300%, or at 500% compared to the host cells without the one or more polynucleotides that encode a C4-dicarboxylic acid transporter, when cultivated under the same conditions.

In some aspects, the host cell comprises a heterologous polynucleotide that encodes a C4-dicarboxylic acid transporter. In one aspect, the heterologous polynucleotide that encodes a C4-dicarboxylic acid transporter is selected from: (a) a polynucleotide that encodes a C4-dicarboxylic acid transporter having at least 65% sequence identity to SEQ ID NO: 6; (b) a polynucleotide that hybridizes under low stringency conditions with SEQ ID NO: 5, or the full-length complementary strand thereof; and (c) a polynucleotide that has at least 65% sequence identity to SEQ ID NO: 5. As can be appreciated by one of skill in the art, in some instances the heterologous polynucleotide that encodes a C4-dicarboxylic acid transporter may qualify under more than one of the selections (a), (b) and (c) noted above.

In one aspect, the heterologous polynucleotide encodes a C4-dicarboxylic acid transporter having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 6. In one aspect, the C4-dicarboxylic acid transporter sequence differs by no more than ten amino acids, e.g., by no more than five amino acids, by no more than four amino acids, by no more than three amino acids, by no more than two amino acids, or by one amino acid from SEQ ID NO: 6.

In one aspect, the C4-dicarboxylic acid transporter comprises or consists of the amino acid sequence of SEQ ID NO: 6, an allelic variant thereof, or a fragment of the foregoing, having C4-dicarboxylic acid transporter activity. In another aspect, the C4-dicarboxylic acid transporter comprises or consists of the amino acid sequence of SEQ ID NO: 6. In another aspect, the C4-dicarboxylic acid transporter comprises or consists of amino acids 1 to 418 of SEQ ID NO: 6. In another aspect, the C4-dicarboxylic acid transporter comprises or consists of amino acids 18 to 418 of SEQ ID NO: 6.

In one aspect, the heterologous polynucleotide encodes a C4-dicarboxylic acid transporter having an amino acid substitution, deletion, and/or insertion of one or more (e.g., two, several) amino acids of SEQ ID NO: 6, as described supra. In some aspects, the total number of amino acid substitutions, deletions and/or insertions of SEQ ID NO: 6, is not more than 10, e.g., not more than 9, 8, 7, 6, 5, 4, 3, 2, or 1.

In one aspect, the heterologous polynucleotide that encodes a C4-dicarboxylic acid transporter hybridizes under at least low stringency conditions, e.g., medium stringency conditions, medium-high stringency conditions, high stringency conditions, or very high stringency conditions with SEQ ID NO: 5, or the full-length complementary strand of the foregoing (see, e.g., J. Sambrook, E. F. Fritsch, and T. Maniatus, 1989, supra).

In one aspect, the heterologous polynucleotide that encodes a C4-dicarboxylic acid transporter has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 5.

In one aspect, the heterologous polynucleotide that encodes a C4-dicarboxylic acid transporter comprises SEQ ID NO: 5. In one aspect, the heterologous polynucleotide comprises nucleotides 1 to 1257 of SEQ ID NO: 5. In one aspect, the heterologous polynucleotide comprises nucleotides 52 to 1257 of SEQ ID NO: 5. In one aspect, the heterologous polynucleotide comprises a subsequence of SEQ ID NO: 5, wherein the subsequence encodes a polypeptide having C4-dicarboxylic acid transporter activity. In one aspect, the number of nucleotides residues in the subsequence is at least 75%, e.g., at least 80%, 85%, 90%, or 95% of the number of nucleotide residues in SEQ ID NO: 5.

In one aspect, the heterologous polynucleotide encodes a fragment of SEQ ID NO: 6, wherein the fragment has C4-dicarboxylic acid transporter activity. In one aspect, the number of amino acid residues in the fragment is at least 75%, e.g., at least 80%, 85%, 90%, or 95% of the number of amino acid residues in SEQ ID NO: 6.

The C4-dicarboxylic acid transporter may also be an allelic variant or artificial variant of a C4-dicarboxylic acid transporter.

The C4-dicarboxylic acid transporter can also include fused polypeptides or cleavable fusion polypeptides, as described supra.

Techniques used to isolate or clone a polynucleotide encoding a C4-dicarboxylic acid transporter are described supra.

The polynucleotide sequence of SEQ ID NO: 5, or a subsequence thereof; as well as the amino acid sequence of SEQ ID NO: 6, or a fragment thereof; may be used to design nucleic acid probes to identify and clone DNA encoding a C4-dicarboxylic acid transporter from strains of different genera or species, as described supra. A genomic DNA or cDNA library prepared from such other organisms may be screened for DNA that hybridizes with the probes described above and encodes a C4-dicarboxylic acid transporter, as described supra.

In one aspect, the nucleic acid probe is SEQ ID NO: 5. In another aspect, the nucleic acid probe is a polynucleotide sequence that encodes SEQ ID NO: 6, or a fragment thereof.

For long probes of at least 100 nucleotides in length, very low to very high stringency and washing conditions are defined as described supra. For short probes of about 15 nucleotides to about 70 nucleotides in length, stringency and washing conditions are defined as described supra.

Polynucleotides encoding the C4-dicarboxylic acid transporter may be obtained from microorganisms of any genus. In one aspect, the C4-dicarboxylic acid transporter may be a bacterial, a yeast, or a filamentous fungal C4-dicarboxylic acid transporter obtained from the microorganisms described herein. In another aspect, the C4-dicarboxylic acid transporter is an *Aspergillus* C4-dicarboxylic acid transporter, such as the *Aspergillus aculeatus* C4-dicarboxylic acid transporter of SEQ ID NO: 6.

Other C4-dicarboxylic acid transporter that can be used with the host cells and methods of use described herein include, but are not limited to, the *Aspergillus flavus* C4 dicarboxylic acid transporter (AFLA_107340), the *Aspergillus oryzae* C4-dicarboxylic acid transporter of SEQ ID NO: 27 (encoded by the polynucleotide sequence of SEQ ID NO: 26; see US 2011/0053233), the *Aspergillus terreus* C4-dicarboxylic acid transporter of SEQ ID NO: 29 (encoded by the polynucleotide sequence of SEQ ID NO: 28; see US 2011/0053233), the *Schizosaccharomyces pombe* C4-dicarboxylic acid transporter of SEQ ID NO: 32 (encoded by the polynucleotide sequence of SEQ ID NO: 30 or 31; see US 2011/0053233), the *Aspergillus aculeatus* C4-dicarboxylic acid transporter of SEQ ID NO: 34 (encoded by the polynucleotide sequence of SEQ ID NO: 33; see U.S. application Ser. No. 13/165,696, entitled "Polypeptides Having C4-dicarboxylic acid Transporter Activity and Polynucleotides Encoding Same" filed Jun. 21, 2011), the *Aspergillus aculeatus* C4-dicarboxylic acid transporter of SEQ ID NO: 36 (encoded by the polynucleotide sequence of SEQ ID NO: 35; see U.S. application Ser. No. 13/165,696, supra), the *Schizosaccharomyces japonicus* C4-dicarboxylic acid transporter of SEQ ID NO: 39 (encoded by the polynucleotide sequence of SEQ ID NO: 37 or 38; see PCT/US11/38881, entitled "C4-dicarboxylic acid Production in Filamentous Fungi" filed Jun. 2, 2011), the *Aspergillus clavatus* C4-dicarboxylic acid transporter of SEQ ID NO: 41 (encoded by the polynucleotide sequence of SEQ ID NO: 40; see U.S. application Ser. No. 13/165,719, entitled "Methods for Improving C4-dicarboxylic acid Production in Filamentous Fungi" filed Jun. 21, 2011), the *Aspergillus fumigatus* C4-dicarboxylic acid transporter of SEQ ID NO: 43 (encoded by the polynucleotide sequence of SEQ ID NO: 42; see U.S. application Ser. No. 13/165,719, supra), or any aspect of the C4-dicarboxylic acid transporter described in the respective reference therein. Any aspect described herein related to sequence identity, hybridization, amino acid modifications (e.g., substitutions, deletions, and/or insertions), fragments or subsequences thereof is embraced for the C4-dicarboxylic acid transporters above.

In some aspects, the C4-dicarboxylic acid transporter has at least 20%, e.g., at least 40%, at least 50%, at least 60%, at least 70%, at least 80%, at least 90%, at least 95%, at least 96%, at least 97%, at least 98%, at least 99%, or 100% of the C4-dicarboxylic acid transporter activity of the mature polypeptide of SEQ ID NO: 6 under the same conditions.

The C4-dicarboxylic acid transporter may also be identified and obtained from other sources including microorganisms isolated from nature (e.g., soil, composts, water, silage, etc.) or DNA samples obtained directly from natural materials (e.g., soil, composts, water, silage, etc.) as described supra.

Malate Dehydrogenases and Polynucleotides Encoding Malate Dehydrogenases

In some aspects of the recombinant host cells and methods described herein, the host cells have malate dehydrogenase activity. The malate dehydrogenase can be any malate dehydrogenase that is suitable for the host cells and their methods of use described herein, such as a naturally occurring malate dehydrogenase or a variant thereof that retains malate dehydrogenase activity. In one aspect, the malate dehydrogenase is present in the cytosol of the host cells. In some aspects, the host cells comprise one or more (e.g., two, several) heterologous polynucleotides that encode a malate dehydrogenase.

In some aspects, the host cells comprising the one or more (e.g., two, several) heterologous polynucleotides that encode a malate dehydrogenase have an increased level of malate dehydrogenase activity compared to the host cells without the one or more polynucleotides that encode a malate dehydrogenase, when cultivated under the same conditions. In some aspects, the host cells comprising the one or more heterologous polynucleotides that encode a malate dehydrogenase have an increased level of malate dehydrogenase activity of at least 5%, e.g., at least 10%, at least 15%, at least 20%, at least 25%, at least 50%, at least 100%, at least 150%, at least 200%, at least 300%, or at 500% compared to the host cells without the one or more polynucleotides that encode a malate dehydrogenase, when cultivated under the same conditions.

In some aspects, the host cell comprises a heterologous polynucleotide that encodes a malate dehydrogenase. In one aspect, the heterologous polynucleotide that encodes a malate dehydrogenase is selected from: (a) a polynucleotide that encodes a malate dehydrogenase having at least 65% sequence identity to SEQ ID NO: 8; (b) a polynucleotide that hybridizes under low stringency conditions with (i) SEQ ID NO: 7, (ii) the cDNA sequence of SEQ ID NO: 7; or (iii) the full-length complementary strand of (i) or (ii); and (c) a polynucleotide that has at least 65% sequence identity to SEQ ID NO: 7 or the cDNA sequence of SEQ ID NO: 7. As can be appreciated by one of skill in the art, in some instances the heterologous polynucleotide that encodes a malate dehydrogenase may qualify under more than one of the selections (a), (b) and (c) noted above.

In one aspect, the heterologous polynucleotide encodes a malate dehydrogenase having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 8. In one aspect, the malate dehydrogenase sequence differs by no more than ten amino acids, e.g., by no more than five amino acids, by no more than four amino acids, by no more than three amino acids, by no more than two amino acids, or by one amino acid from SEQ ID NO: 8.

In one aspect, the malate dehydrogenase comprises or consists of the amino acid sequence of SEQ ID NO: 8, an allelic variant thereof, or a fragment of the foregoing, having malate dehydrogenase activity. In another aspect, the malate dehydrogenase comprises or consists of the amino acid sequence of SEQ ID NO: 8. In another aspect, the malate dehydrogenase comprises or consists of amino acids 1 to 330 of SEQ ID NO: 8.

In one aspect, the heterologous polynucleotide encodes a malate dehydrogenase having an amino acid substitution, deletion, and/or insertion of one or more (e.g., two, several) amino acids of SEQ ID NO: 8, as described supra. In some aspects, the total number of amino acid substitutions, deletions and/or insertions of SEQ ID NO: 8, is not more than 10, e.g., not more than 9, 8, 7, 6, 5, 4, 3, 2, or 1.

In one aspect, the heterologous polynucleotide that encodes a malate dehydrogenase hybridizes under at least low stringency conditions, e.g., medium stringency conditions, medium-high stringency conditions, high stringency conditions, or very high stringency conditions with (i) SEQ ID NO: 7, (ii) the cDNA sequence of SEQ ID NO: 7, or (iii) the full-length complementary strand of (i) or (ii) (see, e.g., J. Sambrook, E. F. Fritsch, and T. Maniatus, 1989, supra). In one aspect, the heterologous polynucleotide that encodes a malate dehydrogenase hybridizes under at least low stringency conditions, e.g., medium stringency conditions, medium-high stringency conditions, high stringency conditions, or very high stringency conditions with SEQ ID NO: 7, or the full-length complementary strand thereof. In another aspect, the heterologous polynucleotide that encodes a malate dehydrogenase hybridizes under at least low stringency conditions, e.g., medium stringency conditions, medium-high stringency conditions, high stringency conditions, or very high stringency conditions with the cDNA sequence of SEQ ID NO: 7, or the full-length complementary strand thereof.

In one aspect, the heterologous polynucleotide that encodes a malate dehydrogenase has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 7 or the cDNA sequence of SEQ ID NO: 7. In one aspect, the heterologous polynucleotide that encodes a malate dehydrogenase has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 7. In one aspect, the heterologous polynucleotide that encodes a malate dehydrogenase has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to the cDNA sequence of SEQ ID NO: 7.

In one aspect, the heterologous polynucleotide that encodes a malate dehydrogenase comprises SEQ ID NO: 7. In one aspect, the heterologous polynucleotide comprises nucleotides 1 to 1430 of SEQ ID NO: 7. In one aspect, the heterologous polynucleotide comprises a subsequence of SEQ ID NO: 7, wherein the subsequence encodes a polypeptide having malate dehydrogenase activity. In one aspect, the number of nucleotides residues in the subsequence is at least 75%, e.g., at least 80%, 85%, 90%, or 95% of the number of nucleotide residues in SEQ ID NO: 7.

In one aspect, the heterologous polynucleotide encodes a fragment of SEQ ID NO: 8, wherein the fragment has malate dehydrogenase activity. In one aspect, the number of amino acid residues in the fragment is at least 75%, e.g., at least 80%, 85%, 90%, or 95% of the number of amino acid residues in SEQ ID NO: 8.

The malate dehydrogenase may also be an allelic variant or artificial variant of a malate dehydrogenase.

The malate dehydrogenase can also include fused polypeptides or cleavable fusion polypeptides, as described supra.

Techniques used to isolate or clone a polynucleotide encoding a malate dehydrogenase are described supra.

The polynucleotide sequence of SEQ ID NO: 7, or a subsequence thereof; as well as the amino acid sequence of SEQ ID NO: 8, or a fragment thereof; may be used to design nucleic acid probes to identify and clone DNA encoding a malate dehydrogenase from strains of different genera or species, as described supra. A genomic DNA or cDNA library prepared from such other organisms may be screened for DNA that hybridizes with the probes described above and encodes a malate dehydrogenase, as described supra.

In one aspect, the nucleic acid probe is SEQ ID NO: 7. In another aspect, the nucleic acid probe is a polynucleotide sequence that encodes SEQ ID NO: 8, or a fragment thereof.

For long probes of at least 100 nucleotides in length, very low to very high stringency and washing conditions are defined as described supra. For short probes of about 15 nucleotides to about 70 nucleotides in length, stringency and washing conditions are defined as described supra.

Polynucleotides encoding the malate dehydrogenase may be obtained from microorganisms of any genus. In one aspect, the malate dehydrogenase may be a bacterial, a yeast, or a filamentous fungal malate dehydrogenase obtained from the microorganisms described herein. In another aspect, the malate dehydrogenase is an *Aspergillus* malate dehydrogenase, such as the *Aspergillus oryzae* malate dehydrogenase of SEQ ID NO: 8.

Other malate dehydrogenases that can be used with the host cells and methods of use described herein include, but are not limited to, a *Aspergillus nidulans* malate dehydrogenase (AN6717.1; SIMS et al., 2004, *Mycol. Res.* 108: 853-857); *Aspergillus niger* malate dehydrogenase (An16g00120; Pel et al., 2007, *Nature Biotechnology* 25: 221-231); *Phytophthora infestans* malate dehydrogenase (PITG 13614.1; Calcagno et al., 2009, *Mycological Research* 113: 771-781); *Saccharomyces cerevisiae* malate dehydrogenase (YKL085W; McAlister-Henn and Thompson, 1987, *J. Bacteriol.* 169: 5157-5166); *Talaromyces emersonii* malate dehydrogenase (AF439996, AF487682; Maloney et al., 2004, *Eur. J. Biochem.* 271: 3115-3126); and *Ustilago maydis* malate dehydrogenase (um00403, um11161; McCann and Snetselaar, 2008, *Fungal Genetics and Biology* 45: S77-S87), the *Aspergillus oryzae* malate dehydrogenase of SEQ ID NO: 45 (encoded by the polynucleotide sequence of SEQ ID NO: 44; see U.S. application Ser. No. 12/870,523, entitled "Methods for Improving Malic Acid Production in Filamentous Fungi" filed Aug. 27, 2010), or any aspect of the malate dehydrogenase described in the respective reference therein. Any aspect described herein related to sequence identity, hybridization, amino acid modifications (e.g., substitutions, deletions, and/or insertions), fragments or subsequences thereof is embraced for the malate dehydrogenases above.

In some aspects, the malate dehydrogenase has at least 20%, e.g., at least 40%, at least 50%, at least 60%, at least 70%, at least 80%, at least 90%, at least 95%, at least 96%, at least 97%, at least 98%, at least 99%, or 100% of the malate dehydrogenase activity of the mature polypeptide of SEQ ID NO: 8 under the same conditions.

The malate dehydrogenase may also be identified and obtained from other sources including microorganisms isolated from nature (e.g., soil, composts, water, silage, etc.) or DNA samples obtained directly from natural materials (e.g., soil, composts, water, silage, etc.) as described supra.

Pyruvate Carboxylases and Polynucleotides Encoding Pyruvate Carboxylases

In some aspects of the recombinant host cells and methods described herein, the host cells have pyruvate carboxylase activity. The pyruvate carboxylase can be any pyruvate carboxylase that is suitable for the host cells and their methods of use described herein, such as a naturally occurring pyruvate carboxylase or a variant thereof that retains pyruvate carboxylase activity. In one aspect, the pyruvate carboxylase is present in the cytosol of the host cells. In some aspects, the host cells comprise one or more (e.g., two, several) heterologous polynucleotides that encode a pyruvate carboxylase.

In some aspects, the host cells comprising the one or more (e.g., two, several) heterologous polynucleotides that encode a pyruvate carboxylase have an increased level of pyruvate carboxylase activity compared to the host cells without the one or more polynucleotides that encode a pyruvate carboxylase, when cultivated under the same conditions. In some aspects, the host cells comprising the one or more heterologous polynucleotides that encode a pyruvate carboxylase have an increased level of pyruvate carboxylase activity of at least 5%, e.g., at least 10%, at least 15%, at least 20%, at least 25%, at least 50%, at least 100%, at least 150%, at least 200%, at least 300%, or at 500% compared to the host cells without the one or more polynucleotides that encode a pyruvate carboxylase, when cultivated under the same conditions.

In some aspects, the host cell comprises a heterologous polynucleotide that encodes a pyruvate carboxylase. In one aspect, the heterologous polynucleotide that encodes a pyruvate carboxylase is selected from: (a) a polynucleotide that encodes a pyruvate carboxylase having at least 65% sequence identity to SEQ ID NO: 10; (b) a polynucleotide that hybridizes under low stringency conditions with (i) SEQ ID NO: 9, (ii) the cDNA sequence of SEQ ID NO: 9, or (iii) the full-length complementary strand of (i) or (ii); and (c) a polynucleotide that has at least 65% sequence identity to SEQ ID NO: 9 or the cDNA sequence of SEQ ID NO: 9. As can be appreciated by one of skill in the art, in some instances the heterologous polynucleotide that encodes a pyruvate carboxylase may qualify under more than one of the selections (a), (b) and (c) noted above.

In one aspect, the heterologous polynucleotide encodes a pyruvate carboxylase having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 10. In one aspect, the pyruvate carboxylase sequence differs by no more than ten amino acids, e.g., by no more than five amino acids, by no more than four amino acids, by no more than three amino acids, by no more than two amino acids, or by one amino acid from SEQ ID NO: 10.

In one aspect, the pyruvate carboxylase comprises or consists of the amino acid sequence of SEQ ID NO: 10, an allelic variant thereof, or a fragment of the foregoing, having pyruvate carboxylase activity. In another aspect, the pyruvate carboxylase comprises or consists of the amino acid sequence of SEQ ID NO: 10. In another aspect, the pyruvate carboxylase comprises or consists of amino acids 1 to 1193 of SEQ ID NO: 10.

In one aspect, the heterologous polynucleotide encodes a pyruvate carboxylase having an amino acid substitution, deletion, and/or insertion of one or more (e.g., two, several) amino acids of SEQ ID NO: 10, as described supra. In some aspects, the total number of amino acid substitutions, deletions and/or insertions of SEQ ID NO: 10, is not more than 10, e.g., not more than 9, 8, 7, 6, 5, 4, 3, 2, or 1.

In one aspect, the heterologous polynucleotide that encodes a pyruvate carboxylase hybridizes under at least low stringency conditions, e.g., medium stringency conditions, medium-high stringency conditions, high stringency conditions, or very high stringency conditions with (i) SEQ ID NO: 9, (ii) the cDNA sequence of SEQ ID NO: 9, or (iii) the full-length complementary strand of (i) or (ii) (see, e.g., J. Sambrook, E. F. Fritsch, and T. Maniatus, 1989, supra). In one aspect, the heterologous polynucleotide that encodes a pyruvate carboxylase hybridizes under at least low stringency conditions, e.g., medium stringency conditions, medium-high stringency conditions, high stringency conditions, or very high stringency conditions with SEQ ID NO: 9, or the full-length complementary strand thereof. In one aspect, the heterologous polynucleotide that encodes a pyruvate carboxylase hybridizes under at least low stringency conditions, e.g., medium stringency conditions, medium-high stringency conditions, high stringency conditions, or very high stringency conditions with the cDNA sequence of SEQ ID NO: 9, or the full-length complementary strand thereof.

In one aspect, the heterologous polynucleotide that encodes a pyruvate carboxylase has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 9 or the cDNA sequence of SEQ ID NO: 9. In one aspect, the heterologous polynucleotide that encodes a pyruvate carboxylase has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 9. In one aspect, the heterologous polynucleotide that encodes a pyruvate carboxylase has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to the cDNA sequence of SEQ ID NO: 9.

In one aspect, the heterologous polynucleotide that encodes a pyruvate carboxylase comprises SEQ ID NO: 9. In one aspect, the heterologous polynucleotide comprises nucleotides 1 to 3643 of SEQ ID NO: 9. In one aspect, the heterologous polynucleotide comprises a subsequence of SEQ ID NO: 9, wherein the subsequence encodes a polypeptide having pyruvate carboxylase activity. In one aspect, the number of nucleotides residues in the subsequence is at least 75%, e.g., at least 80%, 85%, 90%, or 95% of the number of nucleotide residues in SEQ ID NO: 9.

In one aspect, the heterologous polynucleotide encodes a fragment of SEQ ID NO: 10, wherein the fragment has pyruvate carboxylase activity. In one aspect, the number of amino acid residues in the fragment is at least 75%, e.g., at least 80%, 85%, 90%, or 95% of the number of amino acid residues in SEQ ID NO: 10.

The pyruvate carboxylase may also be an allelic variant or artificial variant of a pyruvate carboxylase.

The pyruvate carboxylase can also include fused polypeptides or cleavable fusion polypeptides, as described supra.

Techniques used to isolate or clone a polynucleotide encoding a pyruvate carboxylase are described supra.

The polynucleotide sequence of SEQ ID NO: 9, or a subsequence thereof; as well as the amino acid sequence of SEQ ID NO: 10, or a fragment thereof; may be used to design nucleic acid probes to identify and clone DNA encoding a pyruvate carboxylase from strains of different genera or species, as described supra. A genomic DNA or cDNA library prepared from such other organisms may be screened for DNA that hybridizes with the probes described above and encodes a pyruvate carboxylase, as described supra.

In one aspect, the nucleic acid probe is SEQ ID NO: 9. In another aspect, the nucleic acid probe is a polynucleotide sequence that encodes SEQ ID NO: 10, or a fragment of the foregoing.

For long probes of at least 100 nucleotides in length, very low to very high stringency and washing conditions are defined as described supra. For short probes of about 15 nucleotides to about 70 nucleotides in length, stringency and washing conditions are defined as described supra.

Polynucleotides encoding the pyruvate carboxylase may be obtained from microorganisms of any genus. In one aspect, the pyruvate carboxylase may be a bacterial, a yeast, or a filamentous fungal pyruvate carboxylase obtained from the microorganisms described herein. In another aspect, the pyruvate carboxylase is an *Aspergillus* pyruvate carboxylase, such as the *Aspergillus oryzae* pyruvate carboxylase of SEQ ID NO: 10.

Other pyruvate carboxylases that can be used with the host cells and methods of use described herein include, but are not limited to, a *Aspergillus clavatus* NRRL 1 pyruvate carboxylase (XP_001271664; Direct Submission, Submitted (26 Oct. 2006), The Institute for Genomic Research, 9712 Medical Center Drive, Rockville, Md. 20850, USA); *Aspergillus fumigatus* Af293 pyruvate carboxylase (XP_752054; Nierman et al., 2005, *Nature* 438: 1151-1156); *Aspergillus nidulans* FGSC A4 pyruvate carboxylase (XP_662066; Galagan et al., 2005, *Nature* 438: 1105-1115); *Aspergillus niger* pyruvate carboxylase (An15g02820; Pel et al., 2007, *Nature Biotechnology* 25: 221-231; ASPNG 5061; Panneman et al., Submitted (July 1998) to the EMBL/GenBank/DDBJ databases); *Aspergillus terreus* pyruvate carboxylase (O93918; Direct Submission, Submitted (OCT 1998) The Institute for Genomic Research, 9712 Medical Center Drive, Rockville, Md. 20850, USA); *Magnaporthe grisea* 70-15 pyruvate carboxylase (XP_367852; Direct Submission, Submitted (26 Sep. 2005) Broad Institute of MIT and Harvard, 320 Charles Street, Cambridge, Mass. 02142, USA); *Neurospora crassa* OR74A pyruvate carboxylase (XP_965636; Galagan et al., 2003, *Nature* 422: 859-868); *Rhizopus oryzae* pyruvate carboxylase (RO3G_06931.1); *Saccharomyces cerevisiae* pyruvate carboxylase (NP_009777; Gaffeau et al., 1996, *Science* 274: 546-547); *Schizosaccharomyces pombe* pyruvate carboxylase (NP_595900; Direct Submission, Submitted (29 Jun. 2007) European *Schizosaccharomyces* genome sequencing project, Sanger Institute, The Wellcome Trust Genome Campus, Hinxton, Cambridge CB10 1SA); and *Ustilago maydis* pyruvate carboxylase (um01054; McCann and Snetselaar, 2008, *Fungal Genetics and Biology* 45: S77-S87). The invention embraces any aspect of sequence identity, hybridization, variants and fragments described herein as applied to the malate dehydrogenase polypeptide sequences and polynucleotide sequences described above.

In some aspects, the pyruvate carboxylase has at least 20%, e.g., at least 40%, at least 50%, at least 60%, at least 70%, at least 80%, at least 90%, at least 95%, at least 96%, at least 97%, at least 98%, at least 99%, or 100% of the pyruvate carboxylase activity of the mature polypeptide of SEQ ID NO: 10 under the same conditions.

The pyruvate carboxylase may also be identified and obtained from other sources including microorganisms isolated from nature (e.g., soil, composts, water, silage, etc.) or DNA samples obtained directly from natural materials (e.g., soil, composts, water, silage, etc.) as described supra.

Expression Vectors and Nucleic Acid Constructs

The recombinant host cells and methods utilize expression vectors comprising one or more (e.g., two, several) heterologous polynucleotides encoding a carbonic anhydrase, bicarbonate transporter, C4-dicarboxylic acid transporter, malate dehydrogenase, and/or pyruvate carboxylase linked to one or more control sequences that direct expression in a suitable host cell under conditions compatible with the control sequence(s). Such expression vectors may be used in any of the host cells and methods describe herein. The polynucleotides described herein may be manipulated in a variety of ways to provide for expression of a desired polypeptide. Manipulation of the polynucleotide prior to its insertion into a vector may be desirable or necessary depending on the expression vector. The techniques for modifying polynucleotides utilizing recombinant DNA methods are well known in the art.

The various nucleotide and control sequences may be joined together to produce a recombinant expression vector that may include one or more (e.g., two, several) convenient restriction sites to allow for insertion or substitution of the polynucleotide encoding the polypeptide at such sites. Alternatively, the polynucleotide(s) may be expressed by inserting the polynucleotide(s) or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

In one aspect, each polynucleotide encoding a carbonic anhydrase, bicarbonate transporter, C4-dicarboxylic acid transporter, malate dehydrogenase, and/or pyruvate carboxylase described herein is contained on an independent vector. In one aspect, at least two of the polynucleotides are contained on a single vector. In one aspect, at least three of the polynucleotides are contained on a single vector. In one aspect, at least four of the polynucleotides are contained on a single vector. In one aspect, all the polynucleotides encoding the carbonic anhydrase, bicarbonate transporter, C4-dicarboxylic acid transporter, malate dehydrogenase, and pyruvate carboxylase are contained on a single vector.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The expression vector may contain any suitable promoter sequence that is recognized by a host cell for expression of a polynucleotide encoding any polypeptide described herein (e.g., a carbonic anhydrase, bicarbonate transporter, C4-dicarboxylic acid transporter, malate dehydrogenase, or pyruvate carboxylase). The promoter sequence contains transcriptional control sequences that mediate the expression of the polypeptide. The promoter may be any polynucleotide that shows transcriptional activity in the host cell of choice including mutant, truncated, and hybrid promoters, and may be obtained from genes encoding extracellular or intracellular polypeptides either homologous or heterologous to the host cell.

Each polynucleotide described herein may be operably linked to a promoter that is foreign to the polynucleotide. For example, in one aspect, the heterologous polynucleotide encoding a carbonic anhydrase or subunit thereof is operably linked to a promoter that is foreign to the polynucleotide. In another aspect, the heterologous polynucleotide encoding a bicarbonate transporter or subunit thereof is operably linked to promoter foreign to the polynucleotide. In another aspect, the heterologous polynucleotide encoding a C4-dicarboxylic acid transporter or subunit thereof is operably linked to promoter foreign to the polynucleotide. In another aspect, the heterologous polynucleotide encoding a malate dehydrogenase or subunit thereof is operably linked to promoter foreign to the polynucleotide. In another aspect, the heterologous polynucleotide encoding a pyruvate carboxylase or subunit thereof is operably linked to promoter foreign to the polynucleotide.

Examples of suitable promoters for directing the transcription of the nucleic acid constructs in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *E. coli* lac operon, *E. coli* trc promoter (Egon et al., 1988, *Gene* 69: 301-315), *Streptomyces coelicolor* agarase gene (dagA), and prokaryotic beta-lactamase gene (VIIIa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American*, 242: 74-94; and in Sambrook et al., 1989, supra.

Examples of suitable promoters for directing the transcription of the nucleic acid constructs in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from a gene encoding a neutral alpha-amylase in Aspergilli in which the untranslated leader has been replaced by an untranslated leader from a gene encoding triose phosphate isomerase in Aspergilli; non-limiting examples include modified promoters from the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the host cell of choice may be used.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase (gpd). Other useful terminators for yeast host cells are described by Romanos et al., 1992, supra.

The control sequence may also be a suitable leader sequence, when transcribed is a nontranslated region of an mRNA that is important for translation by the host cell. The leader sequence is operably linked to the 5'-terminus of the polynucleotide encoding the polypeptide. Any leader sequence that is functional in the host cell of choice may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence; a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present at the N-terminus of a polypeptide, the propeptide sequence is positioned next to the N-terminus of a polypeptide and the signal peptide sequence is positioned next to the N-terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

The vectors may contain one or more (e.g., two, several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, chloramphenicol, kanamycin, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors may contain one or more (e.g., two, several) elements that permit integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide described herein may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors described herein are well known to one skilled in the art (see, e.g., Sambrook et al., 1989, supra).

Host Cells

Recombinant host cells may comprise one or more (e.g., two, several) polynucleotide(s) described herein which may be operably linked to one or more control sequences that direct the expression of one or more of the described polypeptides for the recombinant production of C4-dicarboxylic acid. The host cell may comprise any polynucleotide encoding a carbonic anhydrase described herein, and optionally comprise any one or combination of a plurality of additional polynucleotides described herein. For example, in one aspect, the recombinant host cell comprises a heterologous polynucleotide encoding a carbonic anhydrase described herein, and optionally comprises one or more heterologous polynucleotides encoding a bicarbonate transporter, a C4-dicarboxylic acid transporter, a malate dehydrogenase, or a pyruvate carboxylase described herein; wherein the host cell produces (or is capable of producing) a greater amount of C4-dicarboxylic acid compared to the host cell without the heterologous polynucleotides when cultivated under the same conditions.

In one aspect, the recombinant host cell comprises one or more (e.g., two, several) heterologous polynucleotides encoding a carbonic anhydrase described herein. In one aspect, the recombinant host cell comprises one or more heterologous polynucleotides encoding a carbonic anhydrase described herein, and one or more heterologous polynucleotide encoding a bicarbonate transporter described herein. In one aspect, the recombinant host cell comprises one or more heterologous polynucleotides encoding a carbonic anhydrase described herein, and one or more heterologous polynucleotides encoding a C4-dicarboxylic acid transporter described herein. In one aspect, the recombinant host cell comprises one or more heterologous polynucleotides encoding a carbonic anhydrase described herein, and one or more heterologous polynucleotides encoding a malate dehydrogenase described herein. In one aspect, the recombinant host cell comprises one or more heterologous polynucleotides encoding a carbonic anhydrase described herein, and one or more heterologous polynucleotides encoding a pyruvate carboxylase described herein.

In one aspect, the recombinant host cell comprises one or more (e.g., two, several) heterologous polynucleotides encoding a carbonic anhydrase described herein, one or more heterologous polynucleotides encoding a bicarbonate transporter described herein, and one or more heterologous polynucleotides encoding a C4-dicarboxylic acid transporter described herein. In one aspect, the recombinant host cell comprises one or more heterologous polynucleotides encoding a carbonic anhydrase described herein, one or more heterologous polynucleotides encoding a bicarbonate transporter described herein, and one or more heterologous polynucleotides encoding a malate dehydrogenase described herein. In one aspect, the recombinant host cell comprises one or more heterologous polynucleotides encoding a carbonic anhydrase described herein, one or more heterologous polynucleotides encoding a C4-dicarboxylic acid transporter described herein, and one or more heterologous polynucleotides encoding a malate dehydrogenase described herein. In one aspect, the recombinant host cell comprises one or more heterologous polynucleotides encoding a carbonic anhydrase described herein, one or more heterologous polynucleotides encoding a bicarbonate transporter described herein, and one or more heterologous polynucleotides encoding a pyruvate carboxylase described herein. In one aspect, the recombinant host cell comprises one or more heterologous polynucleotides encoding a carbonic anhydrase described herein, one or more heterologous polynucleotides encoding a C4-dicarboxylic acid transporter described herein, and one or more heterologous polynucleotides encoding a pyruvate carboxylase described herein. In one aspect, the recombinant host cell comprises one or more heterologous polynucleotides encoding a carbonic anhydrase described herein, one or more heterologous polynucleotides encoding a malate dehydrogenase described herein, and one or more heterologous polynucleotides encoding a pyruvate carboxylase described herein.

In one aspect, the recombinant host cell comprises one or more (e.g., two, several) heterologous polynucleotides encoding a carbonic anhydrase described herein, one or more heterologous polynucleotides encoding a bicarbonate transporter described herein, one or more heterologous polynucleotides encoding a C4-dicarboxylic acid transporter described herein, and one or more heterologous polynucleotides encoding a malate dehydrogenase described herein. In one aspect, the recombinant host cell comprises one or more heterologous polynucleotides encoding a carbonic anhydrase described herein, one or more heterologous polynucleotides encoding a bicarbonate transporter described herein, one or more heterologous polynucleotides encoding a C4-dicarboxylic acid transporter described herein, and one or more heterologous polynucleotides encoding a pyruvate carboxylase described herein. In one aspect, the recombinant host cell comprises one or more heterologous polynucleotides encoding a carbonic anhydrase described herein, one or more heterologous polynucleotides encoding a bicarbonate transporter described herein, one or more heterologous polynucleotides encoding a malate dehydrogenase described herein, and one or more heterologous polynucleotides encoding a pyruvate carboxylase described herein. In one aspect, the recombinant host cell comprises one or more heterologous polynucleotides encoding a carbonic anhydrase described herein, one or more heterologous polynucleotides encoding a C4-dicarboxylic acid transporter described herein, one or more heterologous polynucleotides encoding a malate dehydrogenase described herein, and one or more heterologous polynucleotides encoding a pyruvate carboxylase described herein.

In one aspect, the recombinant host cell comprises one or more (e.g., two, several) heterologous polynucleotides encoding a carbonic anhydrase described herein, one or more heterologous polynucleotides encoding a bicarbonate transporter described herein, one or more heterologous polynucleotides encoding a C4-dicarboxylic acid transporter described herein, one or more heterologous polynucleotides encoding a malate dehydrogenase described herein, and one or more heterologous polynucleotides encoding a pyruvate carboxylase described herein.

In some of these aspects, the recombinant host cell lacks an endogenous carbonic anhydrase, lacks an endogenous bicarbonate transporter, lacks an endogenous C4-dicarboxylic acid transporter, lacks an endogenous malate dehydrogenase, and/or lacks an endogenous pyruvate carboxylase.

In one aspect, the recombinant host cell comprises:

(1) a heterologous polynucleotide that encodes a carbonic anhydrase, wherein the polynucleotide is selected from: (a) a polynucleotide that encodes a carbonic anhydrase having at least 65% sequence identity to SEQ ID NO: 55; (b) a polynucleotide that hybridizes under low stringency conditions with (i) SEQ ID NO: 54, (ii) the cDNA sequence of SEQ ID NO: 54, or (iii) the full-length complementary strand of (i) or (ii); and (c) a polynucleotide that has at least 65% sequence identity to SEQ ID NO: 54 or the cDNA sequence of SEQ ID NO: 54;

and optionally comprises one or more (e.g., two, several) heterologous polynucleotides selected from:

(2) a heterologous polynucleotide that encodes a bicarbonate transporter, wherein the polynucleotide is selected from: (a) a polynucleotide that encodes a bicarbonate transporter having at least 65% sequence identity to SEQ ID NO: 2 or 4; (b) a polynucleotide that hybridizes under low stringency conditions with (i) SEQ ID NO: 1 or 3, (ii) the cDNA sequence of SEQ ID NO: 1 or 3, or (iii) the full-length complementary strand of (i) or (ii); and (c) a polynucleotide that has at least 65% sequence identity to SEQ ID NO: 1 or 3, or the cDNA sequence of SEQ ID NO: 1 or 3;

(3) a heterologous polynucleotide that encodes a C4-dicarboxylic acid transporter, wherein the polynucleotide is selected from: (a) a polynucleotide that encodes a C4-dicarboxylic acid transporter having at least 65% sequence identity to SEQ ID NO: 6; (b) a polynucleotide that hybridizes under low stringency conditions with SEQ ID NO: 5, or the full-length complementary strand thereof; and (c) a polynucleotide that has at least 65% sequence identity to SEQ ID NO: 5;

(4) a heterologous polynucleotide that encodes a malate dehydrogenase, wherein the polynucleotide is selected from: (a) a polynucleotide that encodes a malate dehydrogenase having at least 65% sequence identity to SEQ ID NO: 8; (b) a polynucleotide that hybridizes under low stringency conditions with (i) SEQ ID NO: 7, (ii) the cDNA sequence of SEQ ID NO: 7, or (iii) the full-length complementary strand of (i) or (ii); and (c) a polynucleotide that has at least 65% sequence identity to SEQ ID NO: 7 or the cDNA sequence of SEQ ID NO: 7; and (5) a heterologous polynucleotide that encodes a pyruvate carboxylase, wherein the polynucleotide is selected from: (a) a polynucleotide that encodes a pyruvate carboxylase having at least 65% sequence identity to SEQ ID NO: 10; (b) a polynucleotide that hybridizes under low stringency conditions with (i) SEQ ID NO: 9, (ii) the cDNA sequence of SEQ ID NO: 9, or (iii) the full-length complementary strand thereof; and (c) a polynucleotide that has at least 65% sequence identity to SEQ ID NO: 9 or the cDNA sequence of SEQ ID NO: 9;

wherein the host cell produces (or is capable of producing) a greater amount of C4-dicarboxylic acid compared to the host cell without the heterologous polynucleotide that encodes a carbonic anhydrase, when cultivated under the same conditions.

As can be appreciated by one of skill in the art, in some instances the heterologous polynucleotides that encode the polypeptides noted above may qualify under more than one of the respective selections (a), (b) and (c).

A construct or vector (or multiple constructs or vectors) comprising the one or more (e.g., two, several) polynucleotides is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. In some cases, the choice of a host cell depends upon the gene encoding the polypeptide and its source. The aspects described below apply to the host cells, per se, as well as methods using the host cells.

The host cell may be any cell capable of the recombinant production of a polypeptide described herein, e.g., a prokaryote or a eukaryote, and/or any cell capable of the recombinant production of C4-dicarboxylic acid.

The prokaryotic host cell may be any gram-positive or gram-negative bacterium. Gram-positive bacteria include, but not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but not limited to, *Campylobacter, E. coli, Flavobacterium, Fusobacterium, Helicobacter, Ilyobacter, Neisseria, Pseudomonas, Salmonella,* and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by electroporation (see, e.g., Shigekawa and Dower, 1988, *Biotechniques* 6: 742-751), or by conjugation (see, e.g., Koehler and Thorne, 1987, *J. Bacteriol.* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (*Praha*) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios* 68: 189-207, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes described herein, yeast shall be defined as described in *Biology and Activities of Yeast* (Skinner, F. A., Passmore, S. M., and Davenport, R. R., eds, Soc. App. Bacteriol. Symposium Series No. 9, 1980).

The yeast host cell may be a *Candida, Hansenula, Kluyveromyces, Pichia, Saccharomyces, Schizosaccharomyces, Yarrowia,* or *Issatchenkia* cell, such as a *Candida sonorensis, Candida methanosorbosa, Candida ethanolica, Kluyveromyces lactis, Kluyveromyces marxianus, Pichia fermentans, Pichia galeiformis, Pichia membranifaciens, Pichia deserticola, Saccharomyces carlsbergensis, Saccharomyces cerevisiae, Saccharomyces diastaticus, Saccharomyces bulderi, Saccharomyces douglasii, Saccharomyces kluyveri, Saccharomyces norbensis, Saccharomyces oviformis, Yarrowia lipolytica* or *Issatchenkia orientalis* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus aculeatus, Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum,*

*Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

In one aspect, the host cell is an *Aspergillus* host cell. In another aspect, the host cell is *Aspergillus oryzae.*

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023 and Yelton et al., 1984, *Proc. Natl. Acad. Sci. USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

In some aspects, the host cell comprises one or more (e.g., two, several) polynucleotides described herein, wherein the host cell secretes (and/or is capable of secreting) an increased level of C4-dicarboxylic acid compared to the host cell without the one or more polynucleotides when cultivated under the same conditions. In some aspects, the host cell secretes and/or is capable of secreting an increased level of C4-dicarboxylic acid of at least 5%, e.g., at least 10%, at least 15%, at least 20%, at least 25%, at least 50%, at least 100%, at least 150%, at least 200%, at least 300%, or at 500% compared to the host cell without the one or more polynucleotides, when cultivated under the same conditions. Examples of suitable cultivation conditions are described below and will be readily apparent to one of skill in the art based on the teachings herein.

In any of the aspects of the recombinant host cells and methods described herein, the C4-dicarboxylic acid may be malic acid, succinic acid, oxaloacetic acid, malonic acid, or fumaric acid, or combinations thereof. In some aspects, the C4-dicarboxylic acid is malic acid, succinic acid, or fumaric acid, or combinations thereof. In some aspects, the C4-dicarboxylic acid is malic acid or fumaric acid, or a combination of malic acid and fumaric acid. In some aspects, the C4-dicarboxylic acid is malic acid.

In any of these aspects, the host cell produces (and/or is capable of producing) C4-dicarboxylic acid at a yield of at least than 10%, e.g., at least than 20%, at least than 30%, at least than 40%, at least than 50%, at least than 60%, at least than 70%, at least than 80%, or at least than 90%, of theoretical.

In any of these aspects, the recombinant host has a C4-dicarboxylic acid volumetric productivity greater than about 0.1 g/L per hour, e.g., greater than about 0.2 g/L per hour, 0.5 g/L per hour, 0.6 g/L per hour, 0.7 g/L per hour, 0.8 g/L per hour, 0.9 g/L per hour, 1.0 g/L per hour, 1.1 g/L per hour, 1.2 g/L per hour, 1.3 g/L per hour, 1.5 g/L per hour, 1.75 g/L per hour, 2.0 g/L per hour, 2.25 g/L per hour, 2.5 g/L per hour, or 3.0 g/L per hour; or between about 0.1 g/L per hour and about 2.0 g/L per hour, e.g., between about 0.3 g/L per hour and about 1.7 g/L per hour, about 0.5 g/L per hour and about 1.5 g/L per hour, about 0.7 g/L per hour and about 1.3 g/L per hour, about 0.8 g/L per hour and about 1.2 g/L per hour, or about 0.9 g/L per hour and about 1.1 g/L per hour.

The recombinant host cells may be cultivated in a nutrient medium suitable for production of the carbonic anhydrase, bicarbonate transporter, C4-dicarboxylic acid transporter, malate dehydrogenase, or pyruvate carboxylase using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the desired polypeptide to be expressed and/or isolated. The cultivation takes place in a suitable nutrient medium comprising carbon and nitrogen sources and inorganic salts, as described herein, using procedures known in the art. Suitable media are available from commercial suppliers, may be prepared according to published compositions (e.g., in catalogues of the American Type Culture Collection), or may be prepared from commercially available ingredients.

The carbonic anhydrase, bicarbonate transporter, C4-dicarboxylic acid transporter, malate dehydrogenase, and pyruvate carboxylase, and activities thereof, can be detected using methods known in the art. These detection methods may include use of specific antibodies, formation of an enzyme product, or disappearance of an enzyme substrate. See, for example, Sambrook et al., *Molecular Cloning: A Laboratory Manual*, Third Ed., Cold Spring Harbor Laboratory, New York (2001); Ausubel et al., *Current Protocols in Molecular Biology*, John Wiley and Sons, Baltimore, Md. (1999); and Hanai et al., *Appl. Environ. Microbiol.* 73:7814-7818 (2007)).

Methods

The recombinant host cells described herein may be used for the production of C4-dicarboxylic acid. In one aspect is a method of producing C4-dicarboxylic acid (e.g., malic acid), comprising: (a) cultivating any one of the recombinant host cells described herein (e.g., any host cell with carbonic anhydrase activity, and optionally, bicarbonate transporter activity, C4-dicarboxylic acid transporter activity, malate dehydrogenase activity and/or pyruvate carboxylase activity) in a medium under suitable conditions to produce the C4-dicarboxylic acid; and (b) recovering the C4-dicarboxylic acid. In one aspect, is a method of producing C4-dicarboxylic acid, comprising: (a) cultivating in a medium any one of the recombinant host cells described herein, wherein the host cell comprises one or more (e.g., two, several) heterologous polynucleotides encoding a carbonic anhydrase described herein, and optionally, one or more heterologous polynucleotides encoding a bicarbonate transporter described herein, a C4-dicarboxylic acid transporter described herein, a malate dehydrogenase described herein, and/or a pyruvate carboxylase described herein, under suitable conditions to produce the C4-dicarboxylic acid; and (b) recovering the C4-dicarboxylic acid.

Methods for the production of C4-dicarboxylic acid may be performed in a fermentable medium comprising any one or more (e.g., two, several) sugars, such as glucose, fructose, sucrose, cellobiose, xylose, xylulose, arabinose, mannose, galactose, and/or soluble oligosaccharides. In some instances, the fermentation medium is derived from a natural source, such as sugar cane, starch, or cellulose, and may be the result of pretreating the source by enzymatic hydrolysis (saccharification).

In addition to the appropriate carbon sources from one or more (e.g., two, several) sugar(s), the fermentable medium may contain other nutrients or stimulators known to those skilled in the art, such as macronutrients (e.g., nitrogen sources) and micronutrients (e.g., vitamins, mineral salts, and metallic cofactors). In some aspects, the carbon source can be preferentially supplied with at least one nitrogen source, such as yeast extract, $N_2$, peptone (e.g., Bacto™ Peptone), or soytone (e.g., Bacto™ Soytone). Nonlimiting examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. Examples of mineral salts and metallic cofactors include, but are not limited to Na, P, K, Mg, S, Ca, Fe, Zn, Mn, and Cu.

Suitable conditions used for the methods of C4-dicarboxylic acid production may be determined by one skilled in the art in light of the teachings herein. In some aspects of the methods, the host cells are cultivated for about 12 hours to about 216 hours, such as about 24 hours to about 144 hours, or about 36 hours to about 96 hours. The temperature is typically between about 26° C. to about 60° C., e.g., about 34° C. to about 50° C., and at a pH of about 3.0 to about 8.0, such as about 3.0 to about 7.0, about 3.0 to about 6.0, about 3.0 to about 5.0, about 3.5 to about 4.5, about 4.0 to about 8.0, about 4.0 to about 7.0, about 4.0 to about 6.0, about 4.0 to about 5.0, about 5.0 to about 8.0, about 5.0 to about 7.0, or about 5.0 to about 6.0. In some aspects of the methods, the resulting intracellular pH of the host cell is about 3.0 to about 8.0, such as about 3.0 to about 7.0, about 3.0 to about 6.0, about 3.0 to about 5.0, about 3.5 to about 4.5, about 4.0 to about 8.0, about 4.0 to about 7.0, about 4.0 to about 6.0, about 4.0 to about 5.0, about 5.0 to about 8.0, about 5.0 to about 7.0, or about 5.0 to about 6.0. Cultivation may be performed under anaerobic, microaerobic, or aerobic conditions, as appropriate. In some aspects, the cultivation is performed under anaerobic conditions. Suitable buffering agents are known in the art.

Cultivation may be performed under anaerobic, substantially anaerobic (microaerobic), or aerobic conditions, as appropriate. Briefly, anaerobic refers to an environment devoid of oxygen, substantially anaerobic (microaerobic) refers to an environment in which the concentration of oxygen is less than air, and aerobic refers to an environment wherein the oxygen concentration is approximately equal to or greater than that of the air. Substantially anaerobic conditions include, for example, a culture, batch fermentation or continuous fermentation such that the dissolved oxygen concentration in the medium remains less than 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases. In some embodiments, the cultivation is performed under anaerobic conditions or substantially anaerobic conditions.

The methods of described herein can employ any suitable fermentation operation mode. For example, a batch mode fermentation may be used with a close system where culture media and host microorganism, set at the beginning of fermentation, have no additional input except for the reagents certain reagents, e.g., for pH control, foam control or others required for process sustenance. The process described herein can also be employed in Fed-batch or continuous mode.

The methods described herein may be practiced in several bioreactor configurations, such as stirred tank, bubble column, airlift reactor and others known to those skilled in the art.

The methods may be performed in free cell culture or in immobilized cell culture as appropriate. Any material support for immobilized cell culture may be used, such as alginates, fibrous bed, or argyle materials such as chrysotile, montmorillonite KSF and montmorillonite K-10.

In one aspect of the methods, the C4-dicarboxylic acid (e.g., malic acid) is produced at a titer greater than about 10 g/L, e.g., greater than about 25 g/L, 50 g/L, 75 g/L, 100 g/L, 125 g/L, 150 g/L, 160 g/L, 170 g/L, 180 g/L, 190 g/L, 200 g/L, 210 g/L, 225 g/L, 250 g/L, 275 g/L, 300 g/L, 325 g/L, 350 g/L, 400 g/L, or 500 g/L; or between about 10 g/L and about 500 g/L, e.g., between about 50 g/L and about 350 g/L, about 100 g/L and about 300 g/L, about 150 g/L and about 250 g/L, about 175 g/L and about 225 g/L, or about 190 g/L and about 210 g/L. In one aspect of the methods, the C4-dicarboxylic acid is produced at a titer greater than about 0.01 gram per gram of carbohydrate, e.g., greater than about 0.02, 0.05, 0.75, 0.1, 0.2, 0.3, 0.4, 0.5, 0.6, 0.7, 0.8, 0.9, or 1.0 gram per gram of carbohydrate.

In one aspect of the methods, the amount of produced C4-dicarboxylic acid (e.g., malic acid) is at least 5%, e.g., at least 10%, at least 15%, at least 20%, at least 25%, at least 30%, at least 50%, or at least 100% greater compared to cultivating the host cell without the one or more (e.g., two, several) polynucleotides that encode the carbonic anhydrase under the same conditions.

The recombinant C4-dicarboxylic acid (e.g., malic acid) can be optionally recovered and purified from the fermentation medium using any procedure known in the art (see, for example, WO 1998/022611 and U.S. Pat. No. 7,601,865) including, but not limited to, chromatography (e.g., size exclusion chromatography, adsorption chromatography, ion exchange chromatography), electrophoretic procedures, differential solubility, distillation, extraction (e.g., liquid-liquid extraction), pervaporation, extractive filtration, membrane filtration, membrane separation, reverse osmosis, ultrafiltration, or crystallization. In one example, the C4-dicarboxylic acid is recovered from other material in the fermentation medium by filtration.

In some aspects of the methods, the recombinant C4-dicarboxylic acid before and/or after being optionally purified is substantially pure. With respect to the methods of producing C4-dicarboxylic acid (or a specific C4-dicarboxylic acid thereof, such as malic acid), "substantially pure" intends a recovered preparation of C4-dicarboxylic acid that contains no more than 15% impurity, wherein impurity intends compounds other than C4-dicarboxylic acids. In one variation, a preparation of substantially pure C4-dicarboxylic acid is provided wherein the preparation contains no more than 25% impurity, or no more than 20% impurity, or no more than 10% impurity, or no more than 5% impurity, or no more than 3% impurity, or no more than 1% impurity, or no more than 0.5% impurity.

Suitable assays to test for the production of C4-dicarboxylic acid for the methods of production and host cells described herein can be performed using methods known in the art. For example, the final C4-dicarboxylic acid (and other organic compounds) can be analyzed by methods such as HPLC (High Performance Liquid Chromatography), GC-MS (Gas Chromatography Mass Spectroscopy) and LC-MS (Liquid Chromatography-Mass Spectroscopy) or other suitable analytical methods using routine procedures well known in the art. The release of C4-dicarboxylic acid in the fermentation broth can also be tested with the culture supernatant. Byproducts and residual sugar in the fermentation medium (e.g., glucose) can be quantified by HPLC using, for example, a refractive index detector for glucose and alcohols, and a UV detector for organic acids (Lin et al., *Biotechnol. Bioeng.* 90:775-779 (2005)), or using other suitable assay and detection methods well known in the art.

The following examples are provided by way of illustration and are not intended to be limiting of the invention.

EXAMPLES

Chemicals used as buffers and substrates were commercial products of at least reagent grade.

Fungal Strains

*Aspergillus clavatus* was used as a source of a carbonic anhydrase gene (ACLA_007930). *Aspergillus oryzae* NRRL 3488 (or ATCC 56747) was used as a source of a bicarbonate transporter gene (bt1), a pyruvate carboxylase gene (pyc), a malate dehydrogenase gene (mdh3), and for production of the C4-dicarboxylic acids. *Aspergillus aculeatus* was used as a source of a C4-dicarboxylic acid transport protein gene (c4t521).

Media and Solutions

YEG medium was composed of 20 g glucose, 5 g yeast extract, and deionized water to 1 liter.

COVE plates were composed of 1 M sucrose, 2% COVE salt solution, 10 mM acetamide, 15 mM CsCl, and 25 g/l Agar Noble.

COVE salt solution was composed of 26 g KCl, 26 g $MgSO_4.7H_2O$, 76 g $KH_2PO_4$, 50 ml of COVE trace elements solution, and deionized water to 1 liter.

COVE trace elements solution was composed of 0.04 g $Na_2B_4O_7.10H_2O$, 0.04 g $CuSO_4.5H_2O$, 1.2 g $FeSO_4.7H_2O$, 0.7 g $MnSO_4.H_2O$, 0.8 g $Na_2MoO_2.2H_2O$, 10 g $ZnSO_4.7H_2O$ and deionized water to 1 liter.

Seed medium was composed of 40 g glucose, 6 g Bacto-peptone, 750 mg $KH_2PO_4$, 750 mg $K_2HPO_4$, 100 mg $MgSO_4.7H_2O$, 100 mg $CaCl_2.H_2O$, 5 mg $FeSO_4.7H_2O$, 5 mg NaCl, and deionized water to 1 liter.

Seed medium B was composed of 30 g glucose, 3 g Bacto-peptone, 560 mg $KH_2PO_4$, 560 mg $K_2HPO_4$, 925 mg $NaH_2PO_4.H_2O$, 820 mg $Na_2HPO_4$, 75 mg $MgSO_4.7H_2O$, 75 mg $CaCl_2.H_2O$, 0.75 ml of 1000× Micronutrient Solution, and deionized water to 1 liter.

Acid production medium C was composed of 100 g glucose, 80 g $CaCO_3$, 6 g Bacto Peptone, 150 mg $KH_2PO_4$, 150 mg $K_2HPO_4$, 100 mg $MgSO_4.7H_2O$, 100 mg $CaCl_2.H_2O$, 1 ml 1000× Micronutrient Solution, and deionized water to 1 liter.

Fermentor batch medium was composed of 140 g glucose, 120 g $CaCO_3$, 9 g Bacto-peptone, 150 mg $KH_2PO_4$, 150 mg $K_2HPO_4$, 100 mg $MgSO_4.7H_2O$, 100 mg $CaCl_2$-$2H_2O$, 5 mg $FeSO_4.7H_2O$, 5 mg NaCl, 5 ml Pluronic L61, and deionized water to 1 liter.

1000× Micronutrient solution was composed of 5 g NaCl, 5 g $FeSO_4.7H_2O$, 1 g citric acid, and deionized water to 1 liter.

PDA plates were composed of 39 g/l potato dextrose agar.

2XYT+amp plates were composed of 16 g tryptone, 10 g yeast extract, 5 g NaCl, 100 mg ampicillin, 15 g Bacto agar, and deionized water to 1 liter.

MM plates were composed of 50 ml 20×MM salt solution, 1 mL COVE trace elements solution, 10 g glucose, 20 ml Biotin stock solution, 500 mg $MgSO_4$-$7H_2O$, 20 g Noble agar, pH 6.5 with NaOH, and deionized water to 1 liter.

2 mM+1M Sucrose plates were composed of 50 ml 20× MM salt solution, 1 ml COVE trace elements solution, 342.3 g sucrose, 10 g glucose, 20 ml Biotin stock solution, 500 mg $MgSO_4$-$7H_2O$, 20 g Noble agar, pH 6.5 with NaOH, and deionized water to 1 liter.

20×MM salt solution was composed of 120 g $NaNO_3$, 10.4 g KCl, 30.4 g $KH_2PO_4$, and deionized water to 1 liter.

Biotin stock solution was composed of 5 mM biotin in 100 mM Tris buffer (pH 8.0).

Example 1

Cloning of an *Aspergillus oryzae* Bicarbonate Transporter Gene (bt1) and Construction of Expression Vector pAmFs69

The bicarbonate transporter gene bt1 (AO090012000782) was cloned from *Aspergillus oryzae* NRRL3488 genomic DNA by PCR amplification using primers homologous to the *Aspergillus oryzae* predicted bicarbonate transporter gene model number AO090012000782 found in the published *A. oryzae* ATCC 42149 genome sequence (Galagan et al., 2005, *Nature* 438: 1105-1115).

Genomic DNA from *A. oryzae* NRRL3488 was isolated by inoculating 100 ml YEG medium in a shake flask with 2×10⁶ spores and incubating the flask at 37° C. overnight with shaking at 200 rpm. The mycelia were harvested in MIRACLOTH® (Calbiochem, San Diego, Calif., USA) lined funnel and approximately 2 grams of tissue was frozen in liquid nitrogen. The mycelia were disrupted by grinding in a cold mortar and pestle. Genomic DNA was isolated from the powdered mycelia using a DNeasy® Plant Maxi Kit (QIAGEN Inc., Valencia, Calif., USA) according to the manufacturer's instructions. The *Aspergillus oryzae* bt1 gene was amplified using forward primer 069824 and reverse primer 069825 shown below:

Primer 069824:
(SEQ ID NO: 11)
5'-GTGATAGAACATCGTCCATAATGGAATCCAGCGCTGTACA-3'

Primer 069825:
(SEQ ID NO: 12)
5'-GTGTCAGTCACCTCTAGTTATCAGATTTCAATCTCGTCTT-3'

The amplification reactions were performed using Phusion® Hot Start High-Fidelity DNA Polymerase (Finnzymes Inc., Massachusetts, USA) according to manufacturer's instructions. Each PCR reaction contained 47 ng of *Aspergillus oryzae* NRRL3488 genomic DNA, 200 μM dNTPs, 50 pM of forward primer, 50 pM reverse primer, 1× Phusion® GC Buffer reaction buffer (Finnzymes Inc.), and 50 units of Phusion® Hot Start High-Fidelity DNA Polymerase in a final volume of 50 μl. The amplification reactions were incubated in an EPPENDORF® MASTERCYCLER® (Eppendorf Scientific Inc., Westbury, N.Y., USA) programmed for 1 cycle at 98° C. for 30 seconds; 35 cycles at 98° C. for 10 seconds, 66° C. for 30 seconds, and 72° C. for 2.5 minutes; and 1 cycle at 72° C. for 10 minutes. The PCR product was purified by 1% agarose gel electrophoresis in 50 mM Tris base-50 mM acetate-0.1 mM disodium EDTA (TAE) buffer. A fragment of approximately 2.5 kb was excised from the gel and extracted from the agarose using a QIAQUICK® Gel Extraction Kit (QIAGEN Inc.).

Figure 2:
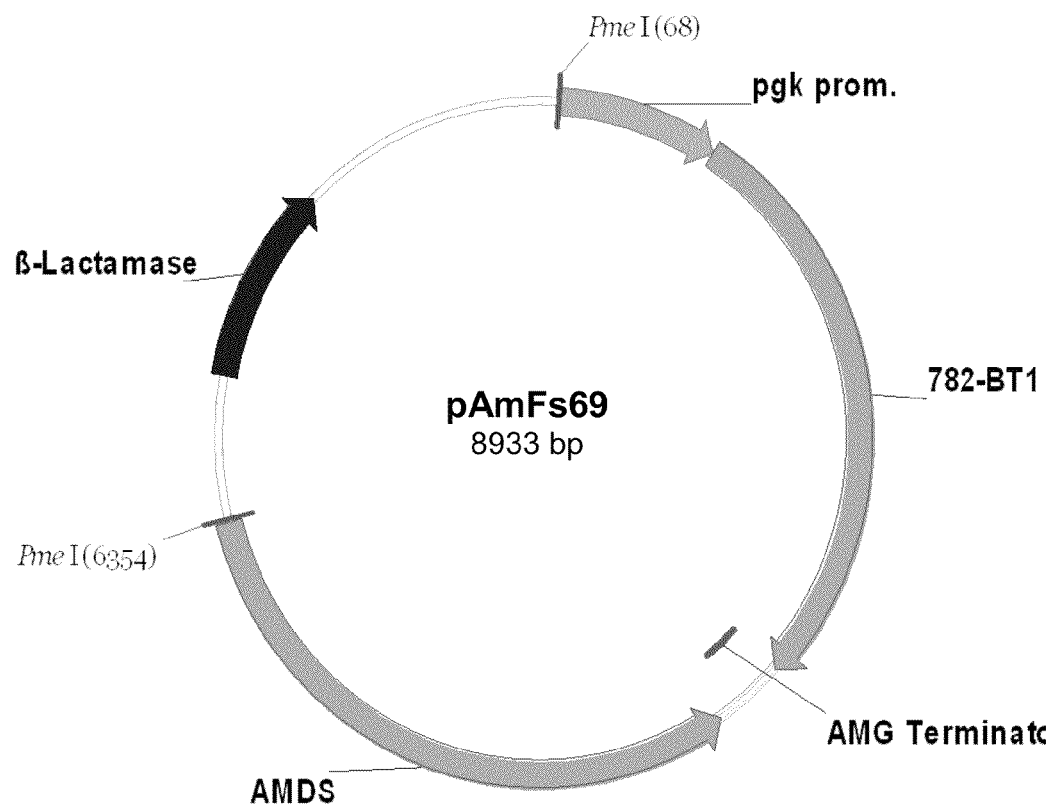
FIG. 2 shows a restriction map of pAmFs69.

Plasmid pShTh60 (FIG. 1; see also PCT Application No. PCT/US10/47002, filed Aug. 27, 2010) was digested with SexAI and Pac I, separated by 0.8% agarose gel electrophoresis in TBE buffer (10.8 g/L Tris Base, 5.5 g/L Boric acid, 2 mM EDTA, pH 8.0) and purified using a QIAQUICK® Gel Extraction Kit (QIAGEN Inc.). The purified PCR product above was then inserted into the digested pShTh60 fragment using an In-Fusion™ Advantage reaction kit (Clontech, Mountain View, Calif., USA) according to the manufacturer's instructions resulting in plasmid pAmFs69 (FIG. 2).

A 2.5 μl aliquot of the ligation reaction above was transformed into ONE SHOT® TOP10 chemically competent *E. coli* cells (Invitrogen, San Diego, Calif., USA) according to the manufacturer's instructions. Transformants were plated onto 2XYT+amp plates and incubated at 37° C. overnight.

DNA sequence analysis was used on the resulting transformants to confirm the integrity of the bt1 coding sequence. Primers 610849, 610851, 610853, 610855, 610857, 610859, and 610861 shown below were used with an ABI3130XL DNA Analyzer (Applied Biosystems, Inc., Foster City, Calif., USA) and the primer walking technique with dye-terminator chemistry (Giesecke et al., 1992, *J. Virol. Methods* 38: 47-60).

```
                                   (SEQ ID NO: 13)
Primer 610849:    5'-GAACAGGAAGAAATCCAAAA-3'

(SEQ ID NO: 14)
Primer 610851:    5'-GTCGGCATAGCCACTGCAAT-3'

(SEQ ID NO: 15)
Primer 610853:    5'-TGTTGCCGCCAAGGGACTTA-3'

(SEQ ID NO: 16)
Primer 610855:    5'-CCGAGAGCGTTGAGTTAATC-3'

(SEQ ID NO: 17)
Primer 610857:    5'-AGCATTAGGGCTAGCTCCGT-3'

(SEQ ID NO: 18)
Primer 610859:    5'-CCAAGATGCCATGTCAGGAC-3'

(SEQ ID NO: 19)
Primer 610861:    5'-TCACAAAAGAGTAGAGGCCA-3'
```

The nucleotide construct of the genomic DNA sequence (SEQ ID NO: 1), and deduced amino acid sequence (SEQ ID NO: 2) of the *Aspergillus aculeatus* bt1 gene are shown in FIGS. 3A and 3B. The genomic coding sequence of 2503 bp (including one stop codon) is interrupted by three introns of 78 bp (465-542), 51 bp (1173-1223), and 61 bp (1747-1807). The corresponding cDNA sequence (bold nucleotide sequence shown in FIGS. 3A and 3B) is 2313 bp, including one stop codon. The predicted encoded protein is 770 amino acids, with a predicted molecular mass of 83.9 kDa and an isoelectric pH of 6.9.

Example 2

Cloning of an *Aspergillus oryzae* Bicarbonate Transporter Gene AO090003000798 and Construction of Corresponding Expression Vector The bicarbonate transporter gene bt2 (AO090003000798) was cloned from *Aspergillus oryzae* NRRL3488 genomic DNA by PCR amplification using primers homologous to the *Aspergillus oryzae* predicted bicarbonate transporter gene model number AO090003000798 found in the published *A. oryzae* ATCC 42149 genome sequence (Galagan et al., 2005, supra).

Genomic DNA from *A. oryzae* NRRL3488 was isolated and the mycelia were harvested and processed as described in Example 1. The *Aspergillus oryzae* bt2 gene was amplified using forward primer 0614058 and reverse primer 0614057 shown below:

```
Primer 0614058:
                                             (SEQ ID NO: 63)
5'-GTGATAGAACATCGTCCATAATGCCGGGCGATCTCAAAACC-3'

Primer 0614057:
                                             (SEQ ID NO: 64)
5'-GTGTCAGTCACCTCTAGTTACTATGCATCAAGGACATTC-3'
```

The amplification reactions were performed using Phusion® Hot Start High-Fidelity DNA Polymerase (Finnzymes) according to manufacturer's instructions. Each PCR reaction contained 47 ng of *Aspergillus oryzae* NRRL3488 genomic DNA, 200 µM dNTPs, 50 pM of forward primer, 50 pM reverse primer, 1× Phusion® GC Buffer reaction buffer (Finnzymes), and 50 units of Phusion® Hot Start High-Fidelity DNA Polymerase in a final volume of 50 µl. The amplification reactions were incubated in an EPPENDORF® MASTERCYCLER® (Eppendorf Scientific Inc.) programmed for 1 cycle at 98° C. for 2 minutes; 35 cycles at 98° C. for 15 seconds, 65° C. for 15 seconds, and 74° C. for 1 minute; and 1 cycle at 74° C. for 1 minute. The PCR product was purified by 1% agarose gel electrophoresis in 50 mM Tris base-50 mM acetate-0.1 mM disodium EDTA (TAE) buffer. A fragment of approximately 2.7 kb was excised from the gel and extracted from the agarose using a QIAQUICK® Gel Extraction Kit (QIAGEN Inc.).

Figure 16:
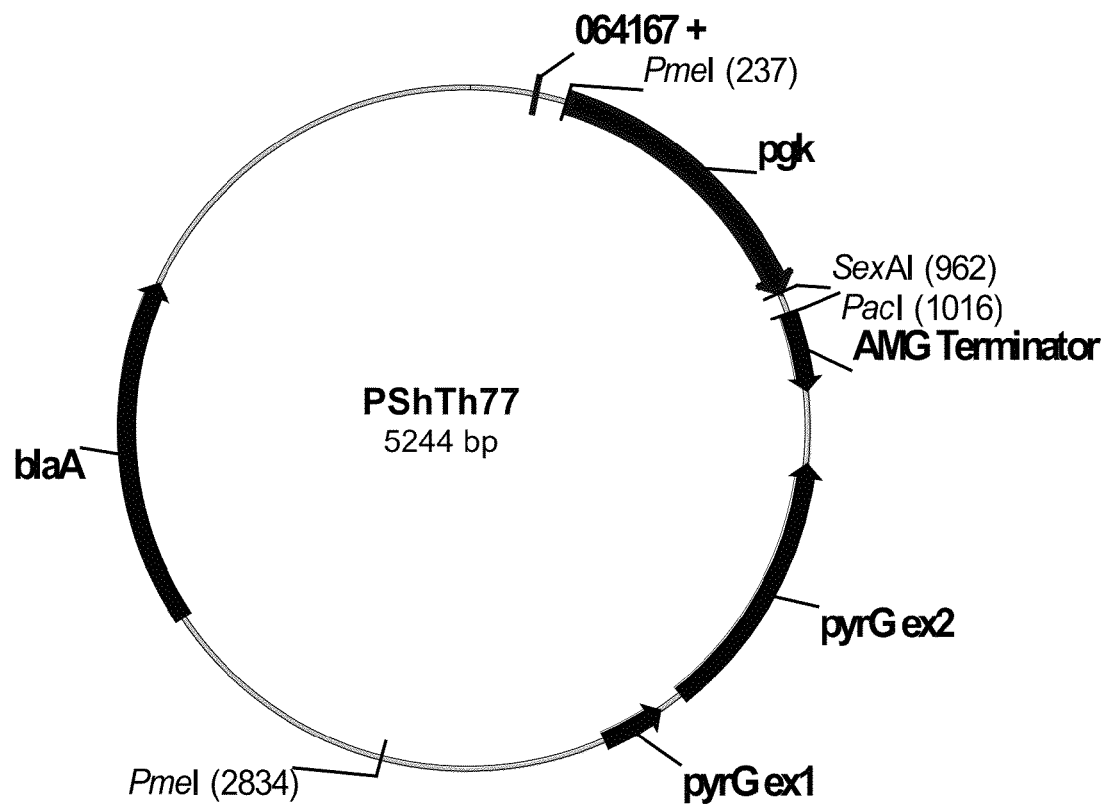
FIG. 16 shows a restriction map of pShTh77.
Figure 17:
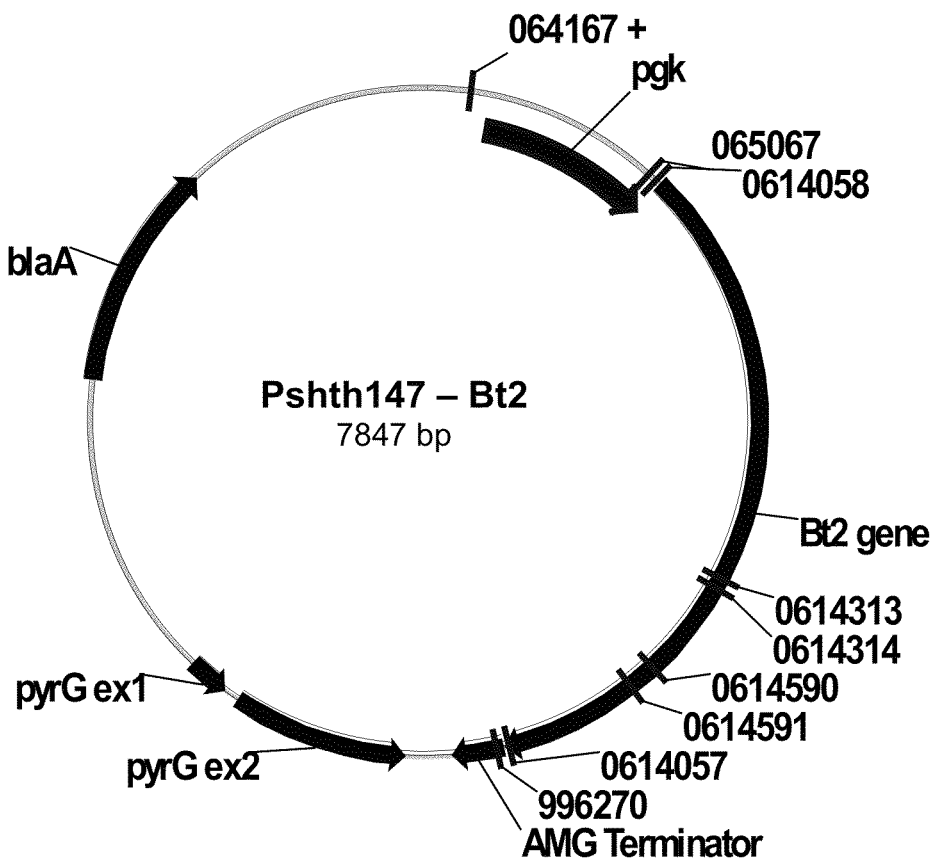
FIG. 17 shows a restriction map of pShTh147.

Plasmid pShTh77 (FIG. 16) was digested with Sex AI and Pac I, separated by 0.8% agarose gel electrophoresis in TBE buffer (10.8 g/L Tris Base, 5.5 g/L Boric acid, 2 mM EDTA, pH 8.0) and purified using a QIAQUICK® Gel Extraction Kit (QIAGEN Inc., Valencia, Calif., USA). The purified PCR product above was then inserted into the digested pShTh77 fragment using an In-Fusion™ Advantage reaction kit (Clontech) according to the manufacturer's instructions resulting in plasmid pShTh147 (FIG. 17).

A 2.5 µl aliquot of the ligation reaction above was transformed into ONE SHOT® TOP10 chemically competent *E. coli* cells according to the manufacturer's instructions. Transformants were plated onto 2XYT+amp plates and incubated at 37° C. overnight.

DNA sequence analysis was used on the resulting transformants to confirm the integrity of the bt2 coding sequence. Primers 0614313, 0614314, 996270, and 0611428, shown below were used with an ABI3130XL DNA Analyzer (Applied Biosystems, Inc., Foster City, Calif., USA) and the primer walking technique with dye-terminator chemistry (Giesecke et al., 1992, *J. Virol. Methods* 38: 47-60).

```
                                   (SEQ ID NO: 65)
Primer 0614313:   5'- GATTGAGATCGGCATTTACT-3'

(SEQ ID NO: 66)
Primer 0614314:   5'-ACGCGGAACAGCAGAATGGC-3'

(SEQ ID NO: 67)
Primer 996270:    5'-CTATAGCGAAATGGATTGATTGTCT-3'

(SEQ ID NO: 68)
Primer 0611428:   5'-TTCACCGTGAAACGTATTGA-3'
```

The nucleotide construct of the genomic DNA sequence (SEQ ID NO: 3), and deduced amino acid sequence (SEQ ID NO: 4) of the *Aspergillus oryzae* bt1 gene are shown in FIGS. 4A and 4B. The genomic coding sequence of 2657 bp (including stop codon) is interrupted by two introns of 64 bp (302-365) and 61 bp (512-572). The corresponding cDNA sequence (bold nucleotide sequence shown in FIGS. 4A and 4B) is 2532 bp, including one stop codon. The predicted encoded protein is 843 amino acids, with a predicted molecular mass of 92.5 kDa and an isoelectric pH of 8.4.

Example 3

Cloning of an *Aspergillus aculeatus* C4-Dicarboxylic Acid Transporter Gene and Construction of Expression Vector pSaMF36

Genomic DNA from *Aspergillus aculeatus* was isolated by inoculating 100 ml of YEG medium in a shake flask with 2×10⁶ spores and incubating the flask at 34° C. overnight with shaking at 160 rpm. The mycelia were harvested by filtration using a MIRACLOTH®(Calbiochem) lined funnel and approximately 2 g of mycelia were recovered and frozen in liquid nitrogen. The frozen mycelia were disrupted by quickly smashing with a hammer while wrapped inside the MIRACLOTH®. The disrupted mycelia were then transferred to a 50 ml polypropylene conical centrifuge tube containing 10 ml of 1× lysis buffer (100 mM EDTA, 10 mM Tris pH 8.0, 1% Triton® X-100, 0.5 M Guanidine-HCl, 200 mM NaCl) and 3 µl of RNase A (QIAGEN Inc.; 100 mg/ml). The tube was mixed by gentle vortexing, and then incubated at room temperature for 5 minutes after which was added 150 µl Proteinase K (QIAGEN Inc.; 20 mg/ml). The tube was mixed by inversion and incubated at 50° C. for 1 hour. The tube was then centrifuged at 7240×g for 20 minutes. The supernatant was then added to a pre-equilibrated QIAGEN-tip 100 (QIAGEN Inc.) and the remaining DNA extraction steps were performed according to the manufacturer's instructions. The DNA was resuspended in 100 µl TE buffer (10 mM Tris Base, 1 mM EDTA, pH 8.0).

The 1257 bp C4-dicarboxylic acid transporter gene c4t521 was amplified from isolated *Aspergillus aculeatus* genomic DNA using primers 069700 and 069701 shown below.

```
Primer 069700:
                                (SEQ ID NO: 20)
5'-TGTGATAGAACATCGTCCATAATGCACGACCACAGC-3'

Primer 069701:
                                (SEQ ID NO: 21)
5'-GTGTCAGTCACCTCTAGTTATCATTCGAACAACTCGGACA-3'
```

The PCR reaction was composed of 10 µl 5× reaction buffer, 1 µl *A. aculeatus* genomic DNA template (105 ng/µl), 1 µl primer 069700 (100 ng/µl), 1 µl primer 069701 (100 ng/µl), 1 µl dNTP mixture (10 mM), 35.5 µl deionized water, and 0.5 µl Phusion™ Hot Start High-Fidelity DNA polymerase (Finnzymes Inc.). The amplification reaction was incubated in an EPPENDORF® MASTERCYCLER® (Eppendorf Scientific Inc.) programmed for 1 cycle at 98° C. for 30 seconds; 30 cycles each at 98° C. for 10 seconds, 60° C. for 30 seconds, 72° C. for 1 minute; and one cycle at 72° C. for 10 minutes. The PCR product was digested with Dpn I for 1 hour to degrade any plasmid DNA template.

Figure 5:
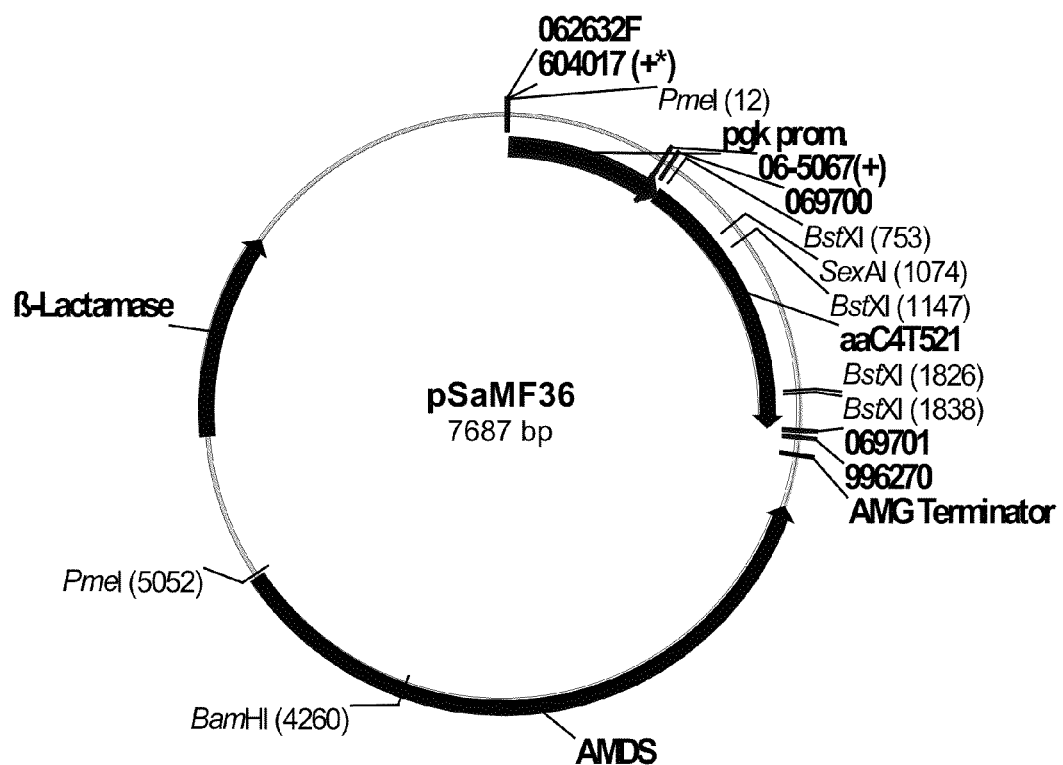
FIG. 5 shows a restriction map of pSaMF36.

Plasmid pShTh60 (FIG. 1) was digested with Sex AI and Pac I, separated by 0.8% agarose gel electrophoresis in TBE buffer, and purified using a QIAQUICK® Gel Extraction Kit. The purified PCR product above was then inserted into the digested pShTh60 fragment using an In-Fusion™ Advantage reaction kit composed of 2 µl 5× buffer, 3 µl purified PCR product (26 ng/µl), 1.5 µl gel-purified Sex AI and Pac I digested and gel-purified pShTh60 (132 ng/µl), 1 µl In-Fusion™ enzyme and 2.5 µl deionized water. The reaction was incubated at 37° C. for 15 minutes, 50° C. for 15 minutes, placed on ice for 5 minutes and diluted with 40 µl TE buffer resulting in pSaMF36 (FIG. 5).

A 2.5 µl aliquot of the ligation reaction above was transformed into ONE SHOT® TOP10 chemically competent *E. coli* cells according to the manufacturer's instructions. Transformants were plated onto 2XYT+amp plates and incubated at 37° C. overnight. The resulting transformants were picked and subjected to DNA sequencing to confirm that the mat521 gene was successfully integrated into the vector.

The nucleotide construct of the genomic DNA sequence (SEQ ID NO: 5) and deduced amino acid sequence (SEQ ID NO: 6) of the *Aspergillus aculeatus* c4t521 gene are shown in FIG. 6. The genomic coding sequence of 1257 bp (including stop codon) contains no introns. The predicted encoded protein is 418 amino acids, with a predicted molecular mass of 46.8 kDa and an isoelectric pH of 6.36. Using the SignalP program (Nielsen et al., 1997, *Protein Engineering* 10:1-6), a signal peptide of 17 residues was predicted. Based on this program, the predicted mature protein contains 401 amino acids with a predicted molecular mass of 44.9 kDa and an isoelectric pH of 6.89.

Example 4

Cloning of an *Aspergillus oryzae* Malate Dehydrogenase Gene and Construction of Expression Vector pSaMF21

Plasmid pSaMF21 was constructed to contain the NAD-dependent malate dehydrogenase (mdh3) gene sequence (DOGAN: AO090701000013), a 1430 bp fragment from *Aspergillus oryzae* as described in PCT Application No. PCT/US10/47002, filed Aug. 27, 2010. The nucleotide construct of the genomic DNA sequence (SEQ ID NO: 7) and deduced amino acid sequence (SEQ ID NO: 8) of the *Aspergillus oryzae* NRRL 3488 malate dehydrogenase mdh3 gene are shown in FIG. 7. The genomic coding sequence of 1430 bp (including stop codon) is interrupted by 7 introns of 57 bp (14-70 bp), 70 bp (103-172 bp), 74 bp (284-357 bp), 68 bp (446-513 bp), 58 bp (892-949 bp), 48 bp (1035-1082 bp), and 62 bp (1228-1289 bp). The G+C content of the coding region of the mdh3 gene is 50.3%. The corresponding cDNA sequence (bold nucleotide sequence shown in FIG. 7) is 993 bp, including one stop codon. The predicted encoded protein is 330 amino acids with a predicted mass of 34.5 kDa and an isoelectric pH of 6.79.

Briefly, the plasmid was constructed by linearizing pShTh60 (FIG. 1) by restriction digestion with Sex AI and Pac I. The digested vector was separated by 0.8% agarose gel electrophoresis in TBE buffer and purified using a QIAQUICK® Gel Extraction Kit. The mdh3 gene was amplified from pShTh71 (PCT Application No. PCT/US10/47002, filed Aug. 27, 2010) using primers 067522 and 067525.

```
Primer 067522:
                                (SEQ ID NO: 22)
5'-AGAACATCGTCCATAATGGTCAAAGCTGGTGAGTTA-3'

Primer 067525:
                                (SEQ ID NO: 23)
5'-GTGTCAGTCACCTCTAGTTATTACTTTGGTGGTGGGTTCT-3'
```

Figure 8:
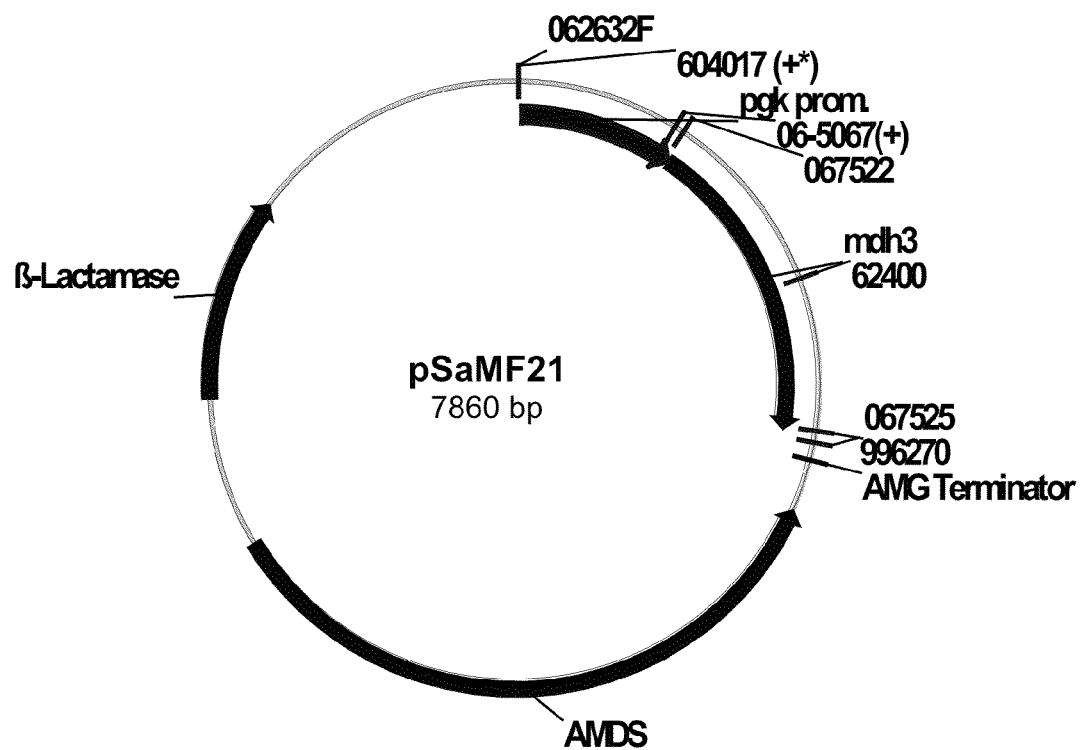
FIG. 8 shows a restriction map of pSaMF21.

The PCR reaction was composed of 5 µl 10× reaction buffer, 1 µl pShTh71 template (87 ng/µl), 1 µl primer 067522 (100 ng/µl), 1 µl primer 067525 (100 ng/µl), 1 µl dNTP mixture (10 mM), 45.5 µl deionized water, and 0.5 µl Herculase® HotStart DNA polymerase (Stratagene, La Jolla, Calif., USA). The amplification reaction was incubated in an EPPENDORF® MASTERCYCLER® (Eppendorf Scientific Inc.) programmed for 1 cycle at 95° C. for 2 minutes; 10 cycles each at 95° C. for 10 seconds, 58° C. for 30 seconds, and 72° C. for 1.5 minutes; 20 cycles each at 95° C. for 10 seconds, 50° C. for 30 seconds, and 72° C. for 1.5 minutes plus 10 seconds per cycle. The PCR reaction was subjected to a restriction digest with Dpn I for 1 hour to degrade any plasmid DNA template. The PCR product was then purified using the MinElute® PCR Purification Kit (QIAGEN Inc.). The purified PCR product was inserted into the vector using an In-Fusion™ Advantage reaction composed of 2 µl 5× buffer, 0.5 µl purified PCR product (110 ng/µl), 1.7 µl gel-purified Sex AI and Pac I restriction digested pShTh60 (FIG. 1; 78 ng/µl), 1 µl In-Fusion™ enzyme and 4.8 µl deinonized water. The reaction was incubated at 37° C. for 15 minutes followed by 50° C. for 15 minutes after which it was placed on ice for 5 minutes and diluted with 40 µl TE buffer resulting in pSaMF21 (FIG. 8). A 2 µl aliquot of the ligation reaction was transformed into ONE SHOT® TOP10 chemically competent *E. coli* cells (Invitrogen) according to the manufacturer's instructions. Transformants were plated onto 2XYT+amp plates and incubated at 37° C. overnight. The resulting transformants were picked and subjected to DNA sequencing to confirm that the mdh3 gene was successfully integrated into the vector.

Example 5

Cloning of an *Aspergillus oryzae* Pyruvate Carboxylase Gene and Construction of Expression Vector pRyan1

Plasmid pRyan1 was constructed to contain the pyruvate carboxylase (pyc) gene sequence (DOGAN: AO090023000801), a 3646 bp fragment from *Aspergillus oryzae* (including two stop codons) as described in PCT Application No. PCT/US10/47002, filed Aug. 27, 2010. The nucleotide construct of the genomic DNA sequence (SEQ ID NO: 9) and deduced amino acid sequence (SEQ ID NO: 10) of the *Aspergillus oryzae* pyruvate carboxylase gene are shown in FIGS. 9A and 9B. Both the *Aspergillus oryzae* NRRL 3488 and ATCC 56747 pyruvate carboxylase genes have the same nucleotide sequence. The G+C content of the coding region of the gene is 57.1%. The genomic coding sequence of 3643 bp (including one stop codon) is interrupted by 1 intron of 61 bp (3475-3535 bp). The G+C content of the coding region of the gene is 57.1%. The corresponding cDNA sequence (bold nucleotide sequence shown in FIGS. 9A and 9B) is 3582 bp, including one stop codon. The predicted encoded protein is 1193 amino acids with a predicted mass of 131 kDa.

Briefly, the plasmid was constructed by linearizing pShTh60 (FIG. 1) by restriction digestion with Sex AI and Pac I. The digested vector was separated by 0.8% agarose gel electrophoresis in TBE buffer and purified using a QIAQUICK® Gel Extraction Kit. The pyc gene was amplified from *Aspergillus oryzae* NRRL 3488 genomic DNA using primers 066549 and 067388 shown below.

```
Primer 066549:
                                (SEQ ID NO: 24)
5'-TAGAACATCGTCCATAATGGCGGCTCCGTTTCGTCA-3'

Primer 067388:
                                (SEQ ID NO: 25)
5'-GTGTCAGTCACCTCTAGTTATTATTACGCTTTGACGATCT-3'
```

The PCR reaction was composed of 5 µl 10× reaction buffer, 1 µl *Aspergillus oryzae* NRRL3488 genomic DNA (110 ng/µl), 1 µl primer 066549 (100 ng/µl), 1 µl primer 067388 (100 ng/µl), 1 µl dNTP mixture (10 mM), 45.5 µl deionized water, and 0.5 µl Herculase® HotStart DNA polymerase. The amplification reaction was incubated in an EPPENDORF® MASTERCYCLER® (Eppendorf Scientific Inc.) programmed for 1 cycle at 95° C. for 2 minutes; 10 cycles each at 95° C. for 10 seconds, 58° C. for 30 seconds, and 72° C. for 3.5 minutes; 20 cycles each at 95° C. for 10 seconds, 58° C. for 30 seconds, and 72° C. for 3.5 minutes plus 10 seconds per cycle. The PCR product was then purified using a MinElute® PCR Purification Kit.

Figure 10:
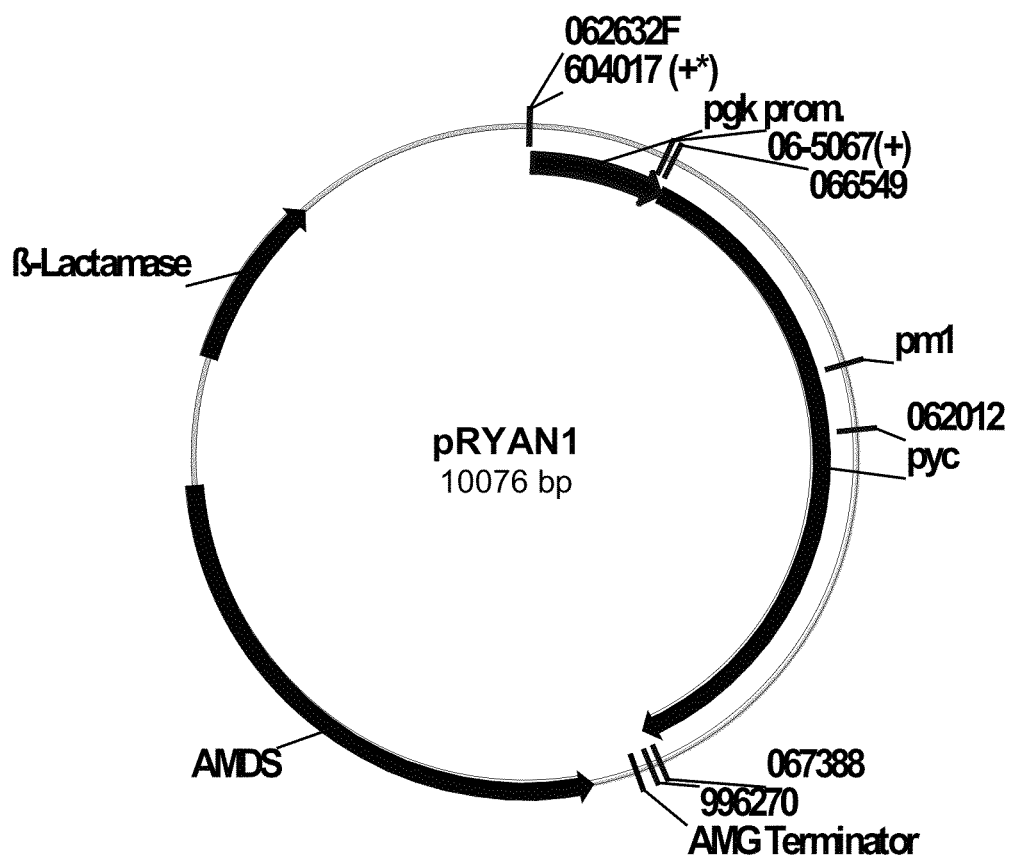
FIG. 10 shows a restriction map of pRYAN1.

The purified PCR product was inserted into the vector using an In-Fusion™ Advantage reaction composed of 2 µl 5× buffer, 1 µl purified PCR product (144 ng/µl), 2 µl gel purified Sex AI and Pac I restriction digested pShTh60 (FIG. 1; 78 ng/µl), 1 µl In-Fusion™ enzyme and 4 µl deionized water. The reaction was incubated at 37° C. for 15 minutes followed by 50° C. for 15 minutes after which it was placed on ice for 5 minutes and diluted with 40 µl TE buffer resulting in pRYAN1 (FIG. 10). A 2 µl aliquot of the ligation reaction was transformed into ONE SHOT® TOP10 chemically competent *E. coli* cells according to the manufacturer's instructions. Transformants were plated onto 2XYT+amp plates and incubated at 37° C. overnight. The resulting transformants were picked and subjected to DNA sequencing to confirm that the pyc gene was successfully integrated into the vector. Nucleotide 1308 was changed from C to T, but did not affect the protein sequence.

Example 6

Preparation of *Aspergillus oryzae* Transformants ShTh6900

Protoplast preparation and transformation of *Aspergillus oryzae* NRRL3488 were performed by inoculating approximately 2×10$^7$ spores into 100 ml YEG medium and incubating the flask at 27° C. for 16-18 hours at 140 rpm. Mycelia were collected by pouring the culture through a sterile funnel lined with MIRACLOTH® and rinsing with 50 ml of 0.7 M KCl. The washed mycelia were resuspended in a 125 ml flask with 20 ml of protoplasting solution composed of 5 mg of GLUCANEX™ (Novozymes A/S, Bagsvrd, Denmark) and 0.5 mg of chitinase (Sigma, USA) per ml of 0.7 M KCl (filter sterilized) and incubated at 34° C., for 30 minutes with mixing at 80 rpm. The protoplasting solution was poured through a sterile funnel lined with MIRACLOTH® and rinsed with 50 ml of STC composed of 1 M sorbitol-10 mM Tris-HCl pH 6.5-10 mM $CaCl_2$. The flow-through was collected in two 50 ml polypropylene tubes. The tubes were spun in the centrifuge at 1300×g for 10 minutes at room temperature. The supernatant was discarded and the protoplast pellet was resuspended in 20 ml of STC buffer. The protoplasts were washed by two rounds pellet resuspension in 20 ml of STC buffer and centrifugation at 1300×g for 10 minutes at room temperature. The final pellet was resuspended in 2 ml of STC buffer. The protoplasts were counted by removing a 10 µl sample and counting them in a haemocytometer (VWR, West Chester, Pa., USA). The volume was adjusted with STC buffer to obtain a protoplast concentration of 2×10$^7$ per ml.

The plasmid expression vectors pAmFs69 (Example 1), pSaMF36 (Example 3), pSaMF21 (Example 4) and pRyan1 (Example 5) were individually prepared for transformation by restriction digestion with Pme I for 4 hours at 37° C. The approximately 5-6 kb expression cassettes from each construct were separated from the vector sequences by 0.8% agarose gel electrophoresis in TBE buffer, and purified using a QIAQUICK® Gel Extraction Kit according to manufacturer's instructions.

Four transformation reactions were prepared by adding 100 µl of protoplast preparation above into four 12 ml polypropylene tubes. To each tube was added two micrograms of the digested pRyan1 pyc fragment, and one microgram each of the digested pAmFs69 bt1 fragment, digested pSaMF36 C4T521 fragment, and the digested pSaMF21 mdh fragment to a 250 µl polyethylene glycol (PEG) solution (60% w/v polyethylene glycol (PEG), 10 mM Tris 6.5, 10 mM CaCl) followed by gentle mixing and incubation at 37° C. for 30 minutes. Each transformation reaction was diluted with 6 ml of STC buffer, followed by plating three separate aliquots onto COVE plates. Each plate was then incubated at 34° C. for 7-10 days. Sixty of the resulting transformants (designated ShTh6900 transformants) were transferred to individual COVE plates and incubated at 34° C. for 5 days. Spore stocks were prepared by collecting the spores in 0.1% TWEEN® 80. Cultures were stored by preparing a glycerol stock of each (800 µl spore stock, 200 µl 0.1% TWEEN® 80) and frozen at −80° C.

Transformants were grown in shake flasks and genomic DNA isolated according to the description above. Individual PCR reactions to test for the presence of each of the four expression vector fragments were composed of 5 µl 10× reaction buffer; 0.5 µl template (80-300 ng/µl); 1.0 µl forward primer (50 pM; see below); 1.0 µl reverse primer (50 pM; see below); 0.5 µl dNTP mixture (10 mM), 16.75 µl deionized water, and 0.25 µl Phusion® DNA polymerase.

```
Forward Primer 065067
(for the pRyan1 pyc, pSaMf21 mdh, and
pSaMf36 C4T521 fragments):
                                    (SEQ ID NO: 46)
5'-TGACCTTCCACGCTGACCAC-3'

Forward Primer 0610854
(for the pAmFs69 bt1 fragment):
                                    (SEQ ID NO: 47)
5'-GGCTGAGAAAATATGTTGCA-3'

Reverse Primer 0611365
(for the pSaMF36 C4T521 fragment):
                                    (SEQ ID NO: 48)
5'-GATAGACCACTAATCATGGTGGCGATGGAG-3'

Reverse Primer 061752
(for the pRyan1 pyc fragment)
                                    (SEQ ID NO: 49)
5'-TGCGGTCCTGAGTCAGGCCCAGTTGCTCGA-3'

Reverse Primer 062400
(for the pSaMF21 mdh fragment)
                                    (SEQ ID NO: 50)
5'-GGGATTTGAACAGCAGAAGG-3'

Reverse Primer 996270
(for the pAmFs69 bt1 fragment)
                                    (SEQ ID NO: 51)
5'-TCACAAAAGAGTAGAGGCCA-3'
```

The amplification reactions were incubated in an EPPENDORF® MASTERCYCLER®(Eppendorf Scientific Inc.) programmed for 1 cycle at 98° C. for 30 seconds; 35 cycles each at 98° C. for 10 seconds; 66° C. (for the pRyan1 pyc fragment) or 58° C. (for the pAmFs69 bt1, pSaMf21 mdh, and pSaMf36 C4T521 fragments) for 10 seconds; 72° C. for 15 seconds; and one cycle of 72° C. for 10 minutes. *Aspergillus oryzae* NRRL 3488 genomic DNA (110 ng/µl) was used as a negative control template and each plasmid (pRyan1, pAmFs69, pSaMf21, or pSaMf36 diluted to 20 ng/µl) was used as positive control template. Amplification reaction mixtures were analyzed by gel electrophoresis using 2 µl of each reaction mixture on a 0.8% agarose gel.

Example 7

Preparation of *Aspergillus oryzae* Transformants ΔPyrG6900 from ShTh6900

Protoplast preparations of *Aspergillus oryzae* transformants ShTh6900 (supra) were performed by inoculating approximately 2×10⁷ spores into 100 ml YEG medium and incubating the flask at 34° C. for 16-18 hours at 160 rpm. Mycelia were collected by pouring the culture through a sterile funnel lined with MIRACLOTH® and rinsing with 50 ml of 0.7 M KCl. The washed mycelia were resuspended in a 125 ml flask with 20 ml of protoplasting solution composed of 5 mg of GLUCANEX™ (Novozymes A/S) and 0.5 mg of chitinase (Sigma) per ml of 0.7 M KCl (filter sterilized) and incubated at 34° C., for 45 minutes with mixing at 80 rpm. The protoplasting solution was poured through a sterile funnel lined with MIRACLOTH® and rinsed with 50 ml of STC buffer (1M Sorbitol, 10 mM CaCl, 10 mM Tris pH 7). The flow-through was collected in two 50 ml polypropylene tubes. The tubes were spun in the centrifuge at 1900×g for 5 minutes at room temperature. The supernatant was discarded and the protoplast pellet was resuspended in 20 ml of STC buffer. The protoplasts were washed by two rounds pellet resuspension in 20 ml of STC buffer and centrifugation at 1900×g for 5 minutes at room temperature. The final pellet was resuspended in 1 ml of STC buffer. The protoplasts were counted by removing a 10 µl sample and counting them in a haemocytometer (VWR). The volume was adjusted with STC buffer to obtain a protoplast concentration of 2×10⁷ per ml.

Figure 15:
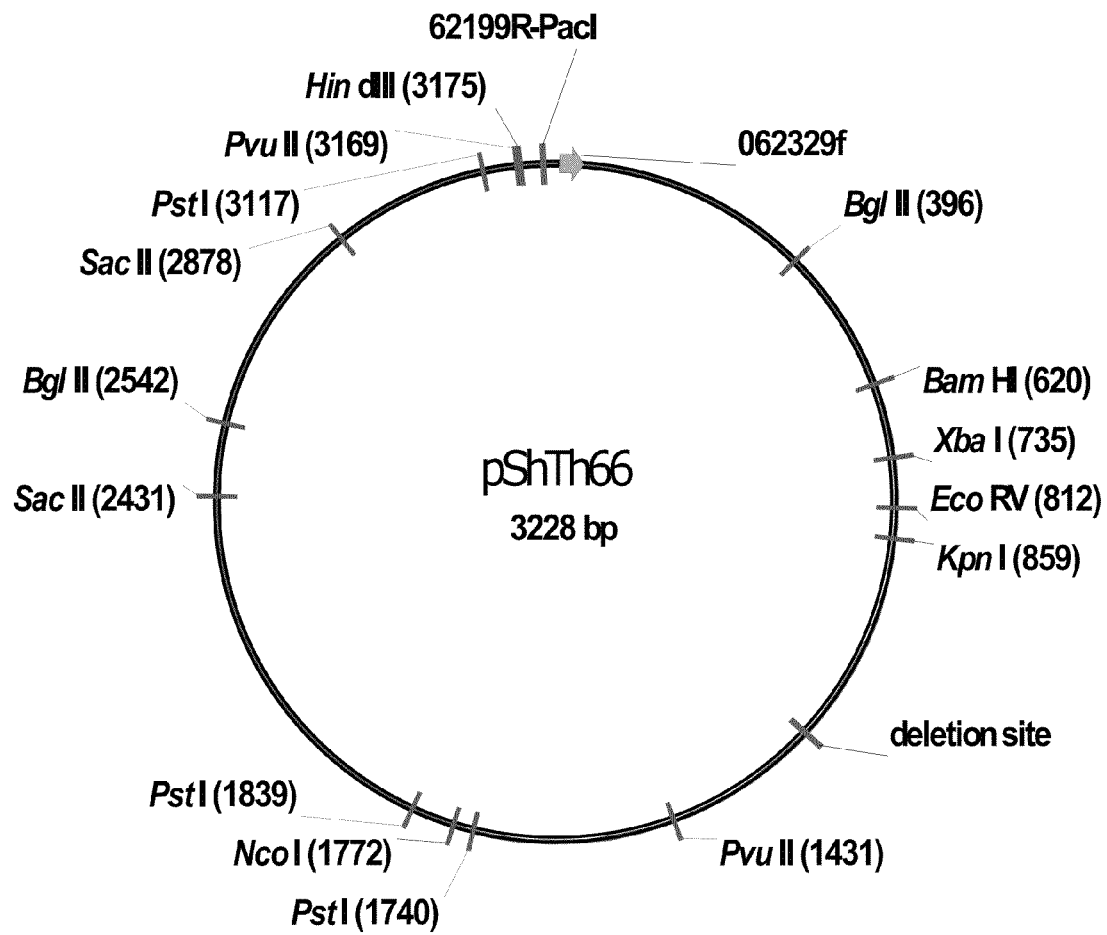
FIG. 15 shows a restriction map of pShTh66.

A pyrG deletion cassette was prepared for transformation by amplifying the deletion fragment from pShTh66 using primers 62329 and 62199. The PCR reaction was composed of 40 µl 10× reaction buffer, 2 µl pShTh66 template (FIG. 15; SEQ ID NO: 62; 200 ng/µl), 8 µl primer 62329 (50 pM/µl), 8 µl primer 62199 (50 pM/µl), 8 µl dNTP mixture (10 mM), 328 µl deionized water, and 6 µl Expand DNA Polymerase (Roche, USA) and split between 4 tubes. The amplification reactions were incubated in an EPPENDORF® MASTERCYCLER® (Eppendorf Scientific Inc.) programmed for 1 cycle at 95° C. for 3 minutes; 10 cycles each at 95° C. for 30 seconds, 57° C. for 30 seconds, and 68° C. for 3 minutes; 25 cycles each at 95° C. for 30 seconds, 57° C. for 30 seconds, and 68° C. for 3 minutes plus 5 seconds each successive cycle; and one cycle at 68° C. for 7 minutes. The PCR product was purified by 1% agarose gel electrophoresis in 50 mM Tris base-50 mM acetate-0.1 mM disodium EDTA (TAE) buffer. A fragment of approximately 3.2 kb was excised from the gel and extracted from the agarose using a QIAQUICK® Gel Extraction Kit (QIAGEN Inc.).

```
Primer 62329:
                                    (SEQ ID NO: 56)
5'-ATTAACTAAAGACCACGAGAGGGGAACTAGGGAAATC-3'

Primer 62199:
                                    (SEQ ID NO: 57)
5'-TTAATTAACTTTCCCCCCCGTAATCTAA-3'
```

Five transformation reactions each were prepared by mixing 100 µl of the *Aspergillus oryzae* ShTh6900 protoplast preparation above with 1 µg of the ~3.2 kb pyrG deletion fragment above in a 12 ml polypropylene tube. 250 µl of polyethylene glycol (PEG) was added and the reactions gently mixed, followed by incubation at 37° C. for 30 minutes. 5 ml YP5% glucose, 10 mM uridine was added to each reaction and the tubes allowed to incubate at 34° C. overnight. Each reaction was plated onto two MM 1M Sucrose+uridine+FOA plates and incubated at 34° C. for 7-10 days. The resulting transformants then were transferred to individual MM+uridine+FOA plates and incubated at 34° C. for 5 days. The transformants were subjected to 2 rounds of spore purification after which they were plated onto MM+uridine plates. Spore stocks were prepared by collecting the spores in 0.1% TWEEN® 80. The resulting transformant cultures, designated ΔPyrG6900, were stored at −80° C. in a glycerol stock (800 µl spore stock, 200 µl 0.1% TWEEN® 80).

The spore isolates were confirmed by Southern analysis and shown to lack the pyrG gene with no ectopic integration.

A second Southern analysis was prepared with the spore isolates and probed with the amp gene to ensure that no plasmid DNA sequence was present in the strain. No hybridization was seen between any of the transformants and the amp probe.

Example 8

Cloning of an *Aspergillus* Clavatus Carbonic Anhydrase Gene and Construction of Expression Vector pSaMF58

Genomic DNA from *Aspergillus clavatus* NRRL1 was isolated by inoculating 100 ml of YEG medium in a shake flask with all the harvested spores from a 10 day old PDA plate and incubating the flask at 34° C. overnight with shaking at 160 rpm. The mycelia were harvested by filtration using a MIRACLOTH® (Calbiochem) lined funnel and approximately 2 g of mycelia were recovered and frozen in liquid nitrogen. The frozen mycelia were disrupted by quickly smashing with a hammer while wrapped inside miracloth. The disrupted mycelia were then transferred to a 50 ml polypropylene conical centrifuge tube containing 10 ml of 1× lysis buffer (100 mM EDTA, 10 mM Tris pH 8.0, 1% Triton X-100, 0.5 M Guanidine-HCl, 200 mM NaCl) and 3 µl of 100 mg/ml RNase A. The centrifuge tube was mixed by gentle vortexing and then incubated at room temperature for 5 minutes, followed by the addition of 150 µl of 20 mg/ml Proteinase K. The centrifuge tube was mixed by inversion, placed at 50° C. to incubate for 1 hour, and then centrifuged at 7240×g for 20 minutes. The supernatant was then added to a pre-equilibrated QIAGEN-tip 100 (QIAGEN Inc.) and the remaining DNA extraction steps were according to the manufacturer's instructions. The DNA was resuspended in 50 µl of TE buffer.

The carbonic anhydrase (CA) gene (ACLA_007930) was amplified from isolated *Aspergillus clavatus* genomic DNA by PCR amplification using primers 0612826 and 0612827 shown below.

```
Primer 0612826:
                                    (SEQ ID NO: 52)
5'-CCAACAGACACATCTAAACAATGTCCGACAAGGCTC-3'

Primer 0612827:
                                    (SEQ ID NO: 53)
5'-GTGTCAGTCACCTCTAGTTATCAGCTCTTGGTGATATTGT-3'
```

The PCR reaction was composed of 10 µl 5× reaction buffer, 0.5 µl *A. clavatus* NRRL1 genomic DNA template (113 ng/µl), 1 µl primer 0612826 (100 ng/µl), 1 µl primer 0612827 (100 ng/µl), 1 µl dNTP mixture (10 mM), 36 µl deionized water, and 0.5 µl Phusion™ Hot Start High-Fidelity DNA Polymerase (Finnzymes Inc.). The amplification reaction was incubated in an EPPENDORF® MASTERCYCLER® (Eppendorf Scientific Inc.) programmed for 1 cycle at 98° C. for 30 seconds; 30 cycles each at 98° C. for 10 seconds, 60° C. for 30 seconds, and 72° C. for 30 seconds; and one cycle at 72° C. for 10 minutes. The PCR product was then purified using the MinElute® PCR Purification Kit (QIAGEN Inc.) according to the manufacturer's instructions.

Figure 11:
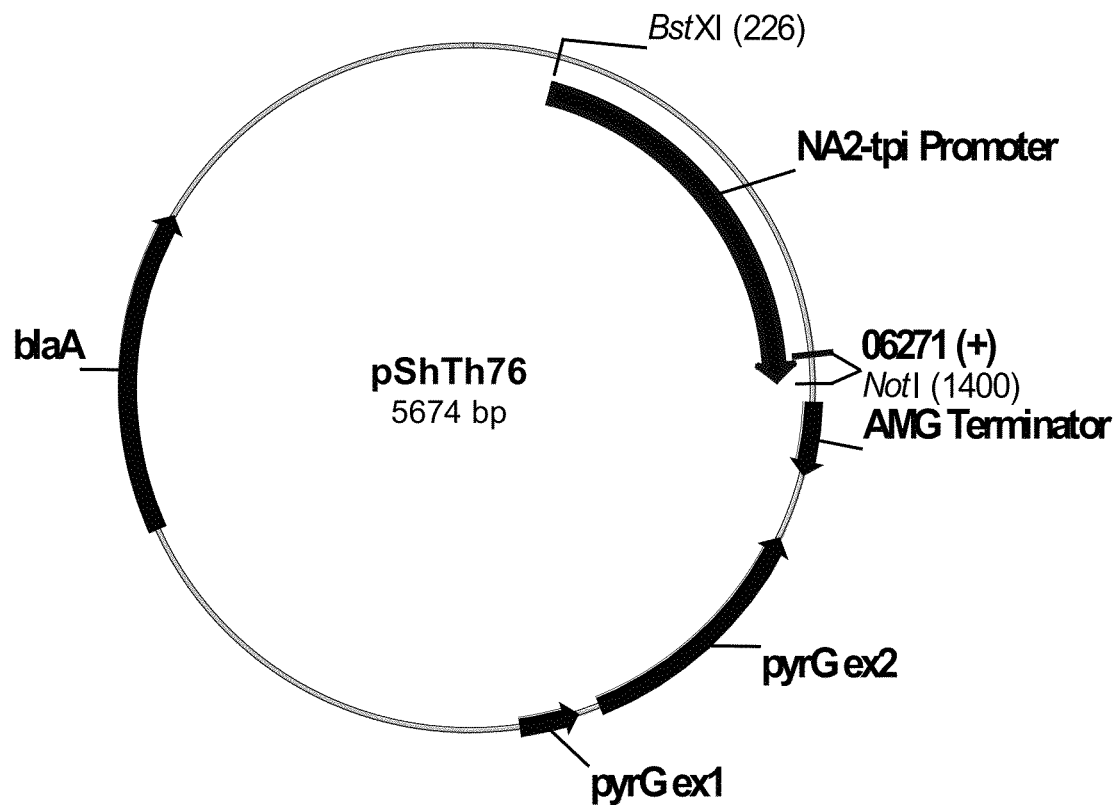
FIG. 11 shows a restriction map of pShTh76.

A Bst XI restriction site was introduced into plasmid pAILo2 (see WO2004/099228) up-stream of the NA2-tpi promoter using oligomer primers 064011 and 064012 with a Quick Change II SL Site Directed Mutagenesis kit (Agilent Technologies) resulting in plasmid pShTh76 (FIG. 11).

```
Primer 064011:
                                    (SEQ ID NO: 58)
5'-GGAAACAGCTATGACCATGATTATGGATTGTTTAAACGTCGACGC-
3'

Primer 064012:
                                    (SEQ ID NO: 59)
5'-GCGTCGACGTTTAAACAATCCATAATCATGGTCATAGCTGTTTCC-
3'
```

Plasmid pShTh76 then was linearized by digestion with Bst XI and Bgl II. The digested vector then was separated by 0.8% agarose gel electrophoresis in TBE buffer and gel purified using a Qiagen MinElute® PCR purification kit (QIAGEN Inc.) according to manufacturer's instructions.

The gpd promoter from *A. oryzae* NRRL3488 was amplified using primers 0612469 and 0612468.

```
Primer 0612469:
                                    (SEQ ID NO: 60)
5'-GGAAACAGCTATGACCATGATTCCAGATTGTAAATTAC-3'

Primer 0612468:
                                    (SEQ ID NO: 61)
5'-AGCACTAGTACGCGTAGATCTGTTTAGATGTGTCTGTTGG-3'
```

The PCR reaction was composed of 10 µl 5× reaction buffer, 0.5 µl *A. oryzae* NRRL3488 gDNA template (200 ng/µl), 1 µl primer 0612826 (100 ng/µl), 1 µl primer 0612827 (100 ng/µl), 1 µl dNTP mixture (10 mM), 36 µl deionized water, and 0.5 µl Phusion™ Hot Start High-Fidelity DNA Polymerase (Finnzymes Inc.). The amplification reaction was incubated in an EPPENDORF® MASTERCYCLER® (Eppendorf Scientific Inc.) programmed for 1 cycle at 98° C. for 30 seconds; 30 cycles each at 98° C. for 10 seconds, 65° C. for 30 seconds, and 72° C. for 60 seconds; and one cycle at 72° C. for 10 minutes. The PCR product was then column purified using the MinElute® PCR Purification Kit (QIAGEN Inc.).

Figure 12:
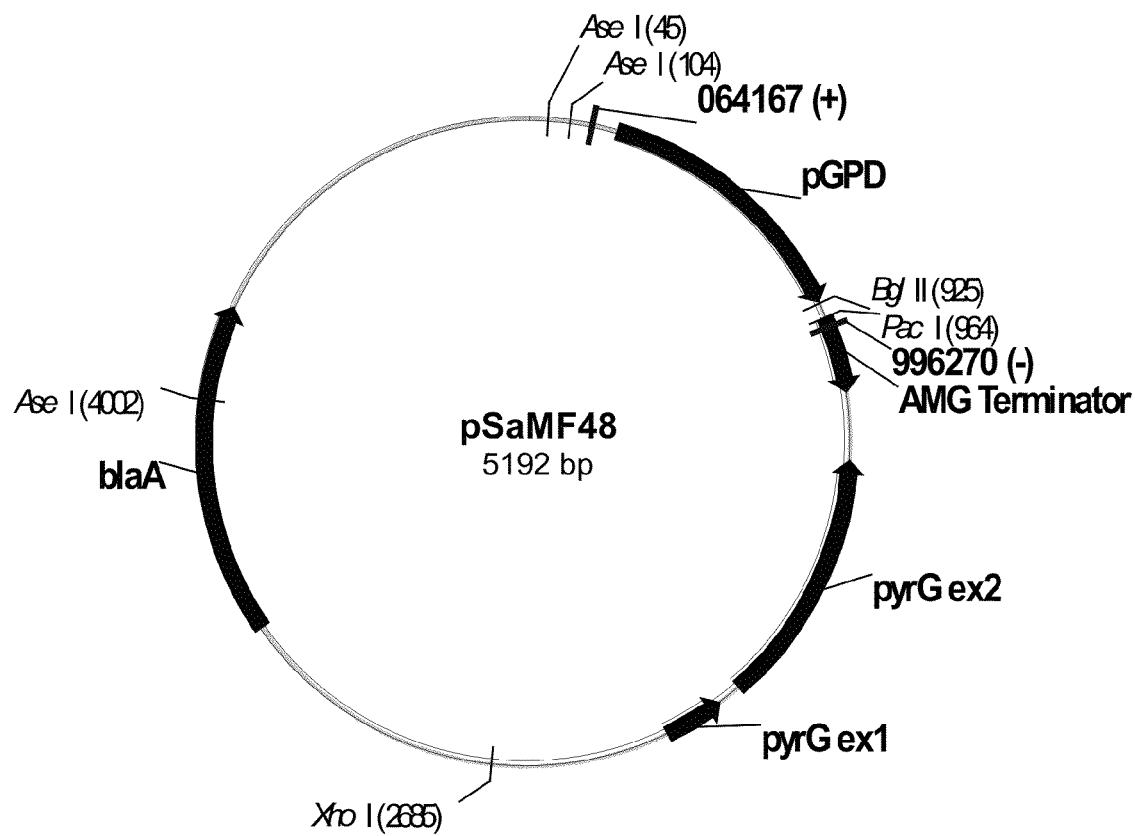
FIG. 12 shows a restriction map of pSaMF48.

The purified PCR product above containing the gpd promoter then was inserted into the digested pShTh76 vector using an In-Fusion™ Advantage reaction composed of 2 µl 5× buffer, 2 µl purified PCR product (42 ng/µl), 2.7 µl gel-purified Bst XI and Bgl II restriction digested pShTh76 (75 ng/µl), 1 µl In-Fusion™ enzyme and 2.3 µl deionized water. The reaction was incubated at 37° C. for 15 minutes then 50° C. for 15 minutes after which it was placed on ice for 5 minutes and diluted with 40 µl TE buffer resulting in pSaMF48. A 2.5 µl aliquot of the ligation reaction was transformed into ONE SHOT® TOP10 chemically competent *E. coli* cells (Invitrogen) according to the manufacturer's instructions. Transformants were plated onto 2XYT+amp plates and incubated at 37° C. overnight. The resulting transformants, designated pSaMF48 (FIG. 12), were picked and subjected to DNA sequencing to confirm that the gpd promoter was successfully integrated into the vector.

Figure 13:
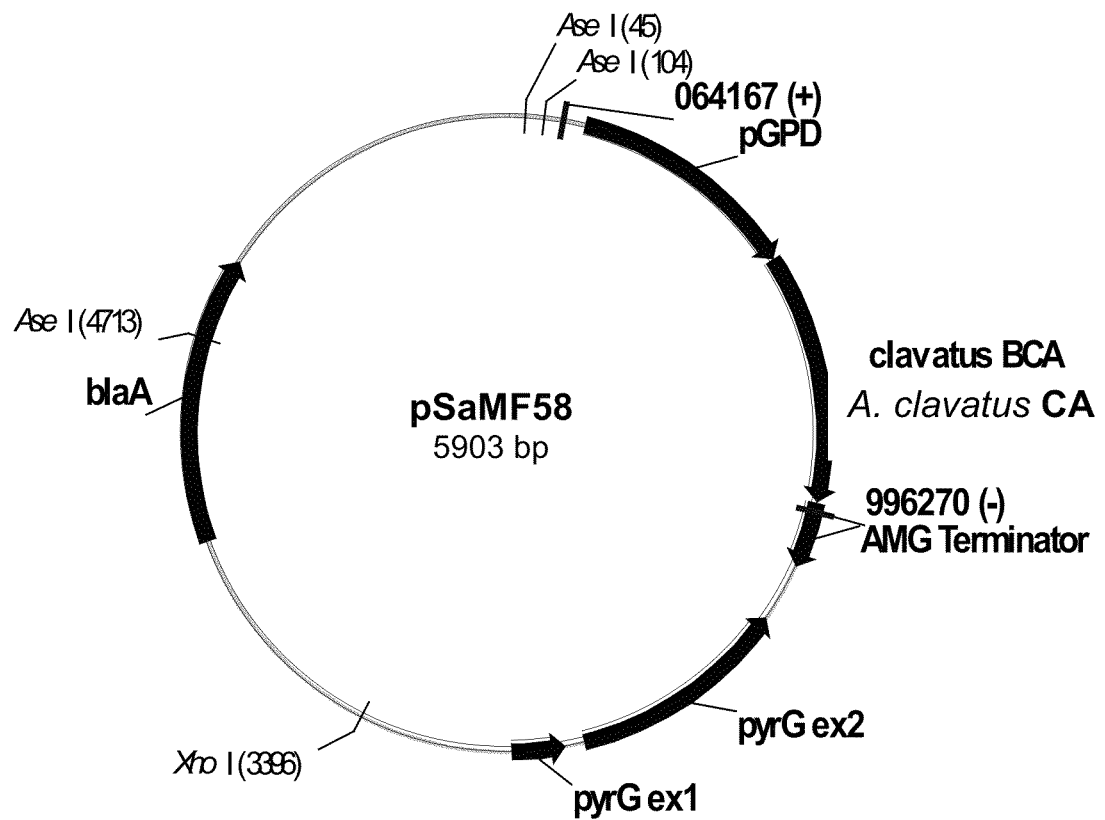
FIG. 13 shows a restriction map of pSaMF58.

Plasmid pSaMF48 (FIG. 12) was digested with Bgl II and Pac I, separated by 0.8% agarose gel electrophoresis in TBE buffer, and purified using a Nucleospin® Extract II Kit (Macherey-Nagel, Bethlehem, Pa., USA) according to manufacturer's instructions. The purified PCR product above containing the *Aspergillus clavatus* carbonic anhydrase gene of SEQ ID NO: 54 was then inserted into the vector using an In-Fusion™ Advantage reaction composed of 2 µl 5× buffer, 0.25 µl purified PCR product (187 ng/µl), 0.26 µl of the Bgl II and Pac I restriction digested and gel-purified pSaMF48 above (557 ng/µl), 1 µl In-Fusion™ enzyme, and 6.49 µl deionized water. The reaction was incubated at 37° C. for 15 minutes then 50° C. for 15 minutes after which it was placed on ice for 5 minutes and diluted with 40 µl TE buffer resulting in pSaMF58 (FIG. 13).

A 2.5 µl aliquot of the ligation reaction was transformed into ONE SHOT® TOP10 chemically competent *E. coli* cells (Invitrogen) according to the manufacturer's instructions. Transformants were plated onto 2XYT+amp plates and incubated at 37° C. overnight. The resulting transformants were picked and subjected to DNA sequencing to confirm that the CA gene was successfully integrated into the vector.

The nucleotide construct of the genomic DNA sequence (SEQ ID NO: 54) and deduced amino acid sequence (SEQ ID NO: 55) of the *Aspergillus* clavatus carbonic anhydrase gene are shown in FIG. 14. The genomic coding sequence of 750 bp (including stop codon) is interrupted by one intron of 72 bp (153-224). The corresponding cDNA sequence (bold nucleotide sequence shown in FIG. 13) is 678 bp, including one stop codon. The predicted encoded protein is 225 amino acids, with a predicted molecular mass of 25.7 kDa and an isoelectric pH of 6.48.

Example 9

Transformation of an Expression Vector Fragment of pSaMF58 Containing an *Aspergillus clavatus* Carbonic Anhydrase Gene into *Aspergillus oryzae* Transformants ΔPyrG6900 (SaMF58Q)

The plasmid expression vector pSaMF58 (FIG. 12) was prepared for transformation by digestion with Ase I and Xho I for 4 hours at 37° C. The digested vector was separated on a 0.8% agarose TBE gel, the 3292 bp band containing the expression cassette was cut out and purified using the Nucleospin® Extract II Kit (Macherey-Nagel) according to manufacturer's instructions.

Two transformation reactions were prepared by adding 100 µl of *Aspergillus oryzae* ΔPyrG6900 transformant protoplast preparation (prepared in a similar manner as described above) into each of two 12 ml polypropylene tubes. To each tube was added 5 µg of amp marker free, linearized pSaMF58 vector (supra) and 250 µl of polyethylene glycol (PEG) followed by gentle mixing and incubation at 37° C. for 30 minutes. Each transformation reaction was diluted with 6 ml of STC buffer, separated into 3 ml aliquots, and then each aliquot plated onto a 2 mM+1M Sucrose plate. Each plate was then incubated at 34° C. for 7-10 days. The resulting transformants (designated SaMF58Q) were transferred to individual MM plates and incubated at 34° C. for 5 days. Spore stocks were prepared by collecting the spores in 0.1% TWEEN® 80. Cultures were stored by preparing a glycerol stock of each (800 µl spore stock, 200 µl 0.1% TWEEN® 80) and frozen at −80° C.

Example 10

Production of Malic Acid in Shake Flask Cultures of *Aspergillus oryzae* Transformants Containing an *Aspergillus clavatus* Carbonic Anhydrase Gene (SaMF58Q)

Spores from SaMF58Q transformants described in Example 9 and *Aspergillus oryzae* NRRL 3488 as a control were plated onto individual PDA plates and allowed to sporulate at 34° C. for 5 to 7 days. Spores were collected in 0.1% TWEEN® 80 and counted using a hemacytometer. Seed cultures were prepared in 250 mL flasks containing 100 mL of seed medium B (supplemented with 4.4 mg/L $ZnSO_4.H_2O$) and inoculated with 1 mL of harvested spores. Seed cultures were grown for approximately 22 hours at 30° C. with shaking at 200 rpm. Acid production cultures were prepared in 250 mL unbaffled flasks containing 50 mL of acid production medium C (supplemented with 4.4 mg/L $ZnSO_4.H_2O$) and 3 mL of the 22 hour seed cultures. Cultures were incubated at 30° C. with shaking at 200 rpm for 3 days.

Quantitation of malic acid for the shake flask culture transformants was performed by Reverse Phase High Pressure Liquid Chromatography (RP-HPLC) using an 1200 Series Binary LC System and 1200 Series Diode Array Detector (DAD) (Agilent Technologies, Santa Clara, Calif. USA). Reverse phase separation was performed using an Aqua 5µ C18 125 Å 205×4.6 mm ID column and AQ C18 4×3.0 mm Security Guard Cartridge (Phenomenex, Inc., Torrance, Calif., USA). The mobile phase consisted of 10% methanol (HPLC grade) and 90% 145 mM phosphate pH 1.5 buffer.

Whole culture samples were removed and diluted 1:20 in HPLC Running Buffer composed of 900 ml of 145 mM phosphate buffer and 100 ml of methanol pH 1.50. The samples were then filtered through a 96 well 0.45 micron Durapore PVDF membrane into a 96 well plate for acid analysis.

RP-HPLC was performed using an injection volume of 10 µl at a flow rate of 0.7 ml/minute (isocratic) and column temperature at 20° C. Detection was at 210 nm, 4 nm bandwidth, with the reference at 360 nm, 40 nm bandwidth. The run time was 13 minutes. The void time was determined to be 3.8 minutes. The quantitative capabilities of the reverse phase method were determined for malic acid by performing replicate injections of serially diluted malic acid standards with concentrations ranging from 49.2-3.93 mM. The relative standard deviation for (RSD) for replicate injections was ≤5%. Malic acid shows $R^2 \geq 0.9999$.

*Aspergillus oryzae* SaMF58Q transformants containing an *Aspergillus clavatus* carbonic anhydrase gene (SEQ ID No: 54) showed malic acid titers more than two-fold over the *A. oryzae* NRRL 3488 strains. Additionally, *A. oryzae* SaMF58Q transformants produced titers higher than those observed in separate experiments with the comparable strain *A. oryzae* ShTh6900 (the parent strain to transformant SaMF58Q, but lacking the heterologous carbonic anhydrase gene of SEQ ID No: 54).

Example 11

Fermentation of *Aspergillus oryzae* Transformants Containing an *Aspergillus clavatus* Carbonic Anhydrase Gene (SaMF58Q)

Three *Aspergillus oryzae* SaMF58Q transformants described in Example 9 and control transformant *A. oryzae* ShTh6900 (the parent strain to transformant SaMF58Q, but lacking the heterologous carbonic anhydrase gene of SEQ ID No: 54) were grown for approximately 7 days at 34° C. on PDA plates. A 5-6 ml volume of sterile sodium phosphate buffer (50 mM, pH 6.8) containing 0.2% TWEEN® 80 was added to each plate and spores were suspended by scraping with an inoculating loop. Each suspension was transferred by pipette to a 50 ml conical tube. For each tube, 25 ml of sterile sodium phosphate buffer (50 mM, pH 6.8) containing 0.2% TWEEN® 80 was added to a 500 ml unbaffled flask containing 75 ml of seed medium, which was then inoculated with 2 ml of spore suspension. The flasks were then incubated at 34° C. and 180 rpm for about 24 hours. The seed flasks were combined to supply the 144 ml inoculum required per tank.

Three-liter fermentors containing 1.8 liters of fermentor batch medium (with or without 15 µM supplemental $ZnSO_4$)

were individually inoculated by introducing 144 ml (8%) of the seed culture broth from three combined seed flasks of either *Aspergillus oryzae* SaMF58Q transformants or *Aspergillus oryzae* ShTh6900 transformants. The fermentors were equilibrated at 34° C.±0.1° C. and stirred at 700 rpm. Inlet air flow was maintained at 1 v/v/m. A 30% glucose stream was administered at a rate of approximately 7.3 g/hr beginning at about 20 hours of fermentation, increasing to 9.3 g/hr at 68 hours. 150 g of sterile $CaCO_3$ was added on day 3 to keep the fermentation pH in the range of 6 to 7.

Samples were withdrawn daily and analyzed for malic acid production by liquid chromatography coupled with tandem mass spectrometry (LC-MS/MS) using an Agilent LC-MS/MS system with triple Quad detectors and Masshunter workstation (Agilent Technologies, Santa Clara, Calif. USA) based on the following:

LC column: Waters XBridge Amide column, 3.5 µm, 150× 2.1 mm ID (Waters, Milford, Mass., USA; P/N: 186004861)

Injection volume: 2.0 µL

Sample buffer: 584.48 mg EDTA, 154.16 mg $NH_4Ac$, 200 mL MeOH, 800 mL $H_2O$, 500 uL 25% $NH_3.H_2O$, 11.44 mg, $^{13}C$-labeled malic acid internal standard (Cambridge Isotope Laboratories, Inc., Andover, Mass., USA) and deionized water to 1 liter (pH 8.3).

Solvent A for HPLC: 5 mM $NH_4Ac$ in 80% MeOH

Solvent B for HPLC: 50 mM $(NH_4)_2CO_3$ in 20% AcN, adjust pH to 10 using 25% $NH_3.H_2O$ Running condition: isocratic 30% B, flow rate 0.3 mL/min; column temperature 45° C.

Standards: Malic acid: 60 g/L, 51 g/L, 45 g/L, 30 g/L, 15 g/L, 7.5 g/L, 3.75 g/L, 1.875 g/L each diluted 100 times with double-distilled water and 10 times with sample buffer (final dilution 1000 times); succinic acid, fumaric acid, citric acid, and oxalic acid: each diluted at 8 levels to 1000 times in a similar manner from a 5-10 g/L stock.

MS settings: gas temp: 300° C., gas flow: 10 L/min, nebulizer: 32 psi, Delta EMV(−): 450

MRM settings: Table 1 below.

TABLE 1

| Compound | Precursor | MS1 Res | Product | MS2 Res | Dwell | Fragmentor | Collision Energy | Polarity |
|---|---|---|---|---|---|---|---|---|
| $C_{13}$ Malic acid | 137 | unit | 92 | unit | 50 | 60 | 8 | negative |
| $C_{13}$ Malic acid | 137 | unit | 74 | unit | 50 | 60 | 10 | negative |
| Malic acid | 133 | unit | 89 | unit | 50 | 60 | 8 | negative |
| Malic acid | 133 | unit | 71 | unit | 50 | 60 | 10 | negative |
| Succinic acid | 117 | unit | 99 | unit | 150 | 50 | 5 | negative |
| Succinic acid | 117 | unit | 73 | unit | 50 | 50 | 5 | negative |
| Fumaric acid | 115 | unit | 71 | unit | 50 | 60 | 3 | negative |
| Fumaric acid | 115 | unit | 27 | unit | 50 | 60 | 4 | negative |
| Citric acid | 191 | unit | 111 | unit | 50 | 80 | 5 | negative |
| Citric acid | 191 | unit | 87 | unit | 50 | 80 | 11 | negative |
| Oxalic acid | 89 | unit | 61 | unit | 50 | 60 | 3 | negative |
| Oxalic acid | 89 | unit | 45 | unit | 50 | 60 | 2 | negative |

Whole culture samples were removed daily and diluted 1:10 in HPLC Running Buffer as described for shake-flask samples in Example 10. Samples from day one were further diluted 1:10 with aqueous ammonium (0.0125%), followed by a 1:10 dilution in sample buffer (resulting in a final dilution of 1000-fold). Samples from days 2, 3-5, and 6-8, were prepared in a similar manner, with additional double-distilled water to provide final dilutions of 2000-fold, 4000-fold, and 8000-fold, respectively. Standards for malic acid, succinic acid, fumaric acid, citric acid, and oxalic acid were prepared as appropriate for quantitation and to mimic any matrix effect in the samples. Diluted samples were then analyzed by LC-MS/MS using the parameters described above.

The malic acid production rates for each SaMF58Q transformant over 92 hours of fermentation (normalized to the respective ShTh6900 controls) are shown in Table 2 below. Two of three SaMF58Q transformants achieve malic acid production rates that are significantly above the respective controls.

TABLE 2

| Strain | Normalized C4 Acid Production Rate | |
|---|---|---|
|  | −Zn | +Zn |
| ShTh6900-64.3 | 1.00 | 1.00 |
| SaMF58Q-2 | ND | 1.55 |
| SaMF58Q-4 | ND | 1.15 |
| SaMF58Q-12 | 1.02 | 0.99 |

Although the foregoing has been described in some detail by way of illustration and example for the purposes of clarity of understanding, it is apparent to those skilled in the art that any equivalent aspect or modification, may be practiced. Therefore, the description and examples should not be construed as limiting the scope of the invention.

The present invention may be further described by the following numbered paragraphs:

[1] A recombinant host cell comprising a heterologous polynucleotide that encodes a carbonic anhydrase, wherein the host cell is capable of producing a greater amount of C4-dicarboxylic acid compared to the host cell without the heterologous polynucleotide when cultivated under the same conditions.

[2] The recombinant host cell of paragraph [1], wherein the carbonic anhydrase is a cytosolic carbonic anhydrase.

[3] The recombinant host cell of paragraph [1] or [2], wherein the heterologous polynucleotide:

(a) encodes a carbonic anhydrase having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 55;

(b) hybridizes under low stringency conditions, medium stringency conditions, medium-high stringency conditions, high stringency conditions, or very high stringency conditions with (i) SEQ ID NO: 54, (ii) the cDNA sequence of SEQ ID NO: 54; or (iii) the full-length complementary strand of (i) or (ii); or (c) has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 54, or the cDNA sequence of SEQ ID NO: 54.

[4] The recombinant host cell of any one of paragraphs [1]-[3], wherein the heterologous polynucleotide encodes a carbonic anhydrase having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 55.

[5] The recombinant host cell of any one of paragraphs [1]-[4], wherein the heterologous polynucleotide hybridizes under low stringency conditions, medium stringency conditions, medium-high stringency conditions, high stringency conditions, or very high stringency conditions with (i) SEQ ID NO: 54, (ii) the cDNA sequence of SEQ ID NO: 54; or (iii) the full-length complementary strand of (i) or (ii).

[6] The recombinant host cell of paragraph [5], wherein the heterologous polynucleotide hybridizes under low stringency conditions, medium stringency conditions, medium-high stringency conditions, high stringency conditions, or very high stringency conditions with SEQ ID NO: 54, or the full-length complementary strand thereof.

[7] The recombinant host cell of paragraph [5], wherein the heterologous polynucleotide hybridizes under low stringency conditions, medium stringency conditions, medium-high stringency conditions, high stringency conditions, or very high stringency conditions with the cDNA sequence of SEQ ID NO: 54, or the full-length complementary strand thereof.

[8] The recombinant host cell of any one of paragraphs [1]-[7], wherein the heterologous polynucleotide has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 54, or the cDNA sequence of SEQ ID NO: 54.

[9] The recombinant host cell of paragraph [8], wherein the heterologous polynucleotide has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 54.

[10] The recombinant host cell of paragraph [8], wherein the heterologous polynucleotide has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to the cDNA sequence of SEQ ID NO: 54.

[11] The recombinant host cell of any one of paragraphs [1]-[10], wherein the heterologous polynucleotide encodes a carbonic anhydrase variant of SEQ ID NO: 55, wherein the variant comprises a substitution, deletion, and/or insertion at not more than 10 positions, e.g., not more than 9, 8, 7, 6, 5, 4, 3, 2, or 1 position.

[12] The recombinant host cell of any one of paragraphs [1]-[10], wherein the heterologous polynucleotide encodes a carbonic anhydrase that comprises or consists of SEQ ID NO: 55.

[13] The recombinant host cell of any one of paragraphs [1]-[12], wherein the heterologous polynucleotide is operably linked to a promoter foreign to the polynucleotide.

[14] The recombinant host cell of any one of paragraphs [1]-[13], further comprising a heterologous polynucleotide that encodes a bicarbonate transporter (e.g., a heterologous polynucleotide of SEQ ID NO: 1 or 3, a heterologous polynucleotide that encodes a bicarbonate transporter set forth in SEQ ID NO: 2 or 4, or any related aspect thereof).

[15] The recombinant host cell of paragraph [14], wherein the heterologous polynucleotide that encodes a bicarbonate transporter is operably linked to a promoter foreign to the polynucleotide.

[16] The recombinant host cell of any one of paragraphs [1]-[15], further comprising a heterologous polynucleotide that encodes a C4-dicarboxylic acid transporter (e.g., a heterologous polynucleotide of SEQ ID NO: 5, 26, 28, 30, 31, 33, 35, 37, 38, 40, or 42, a heterologous polynucleotide that encodes a C4-dicarboxylic acid transporter set forth in SEQ ID NO: 6, 27, 29, 32, 34, 36, 39, 41, or 43, or any related aspect thereof).

[17] The recombinant host cell of paragraph [16], wherein the heterologous polynucleotide that encodes a C4-dicarboxylic acid transporter is operably linked to a promoter foreign to the polynucleotide.

[18] The recombinant host cell of any one of paragraphs [1]-[17], further comprising a heterologous polynucleotide that encodes a malate dehydrogenase (e.g., a heterologous polynucleotide of SEQ ID NO: 7 or 44, a heterologous polynucleotide that encodes a malate dehydrogenase set forth in SEQ ID NO: 8 or 45, or any related aspect thereof).

[19] The recombinant host cell of paragraph [18], wherein the heterologous polynucleotide that encodes a malate dehydrogenase is operably linked to a promoter foreign to the polynucleotide.

[20] The recombinant host cell of any one of paragraphs [1]-[19], further comprising a heterologous polynucleotide that encodes a pyruvate carboxylase (e.g., a heterologous polynucleotide of SEQ ID NO: 9, a heterologous polynucleotide that encodes a pyruvate carboxylase set forth in SEQ ID NO: 10, or any related aspect thereof).

[21] The recombinant host cell of paragraph [20], wherein the heterologous polynucleotide that encodes a pyruvate carboxylase is operably linked to a promoter foreign to the polynucleotide.

[22] The recombinant host cell of any one of paragraphs [1]-[13], further comprising a heterologous polynucleotide that encodes a bicarbonate transporter, a heterologous polynucleotide that encodes a C4-dicarboxylic acid transporter, a heterologous polynucleotide encoding a malate dehydrogenase, and a heterologous polynucleotide encoding a pyruvate carboxylase.

[23] The recombinant host cell of any one of paragraphs [1]-[22], wherein the host cell is a eukaryotic host cell.

[24] The recombinant host cell of paragraph [23], wherein the host cell is a filamentous fungal host cell.

[25] The recombinant host cell of paragraph [24], wherein the host cell is selected from the group consisting of an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus,*

*Rhizopus, Schizophyllum, Talaromyces, Thermoascus, Thielavia, Tolypocladium, Trametes,* and *Trichoderma.*

[26] The recombinant host cell of paragraph [25], wherein the host cell is an *Aspergillus* host cell.

[27] The recombinant host cell of paragraph [26], wherein the host cell is an *Aspergillus oryzae* host cell.

[28] The recombinant host cell of any one of paragraphs [1]-[27], wherein the C4-dicarboxylic acid is selected from malic acid, succinic acid, oxaloacetic acid, malonic acid, and fumaric acid.

[29] The recombinant host cell of paragraph [28], wherein the C4-dicarboxylic acid is malic acid.

[30] The recombinant host cell of any one of paragraphs [1]-[29], wherein the host cell is capable of C4-dicarboxylic acid volumetric productivity greater than about 0.1 g/L per hour, e.g., greater than about 0.2 g/L per hour, 0.5 g/L per hour, 0.6 g/L per hour, 0.7 g/L per hour, 0.8 g/L per hour, 0.9 g/L per hour, 1.0 g/L per hour, 1.1 g/L per hour, 1.2 g/L per hour, 1.3 g/L per hour, 1.5 g/L per hour, 1.75 g/L per hour, 2.0 g/L per hour, 2.25 g/L per hour, 2.5 g/L per hour, or 3.0 g/L per hour; or between about 0.1 g/L per hour and about 2.0 g/L per hour, e.g., between about 0.3 g/L per hour and about 1.7 g/L per hour, about 0.5 g/L per hour and about 1.5 g/L per hour, about 0.7 g/L per hour and about 1.3 g/L per hour, about 0.8 g/L per hour and about 1.2 g/L per hour, or about 0.9 g/L per hour and about 1.1 g/L per hour.

[31] The recombinant host cell of any one of paragraphs [1]-[30], wherein the host cell is capable of producing a greater amount of the C4-dicarboxylic acid by at least 5%, e.g., at least 10%, at least 15%, at least 20%, at least 25%, at least 30%, at least 50%, or at least 100% compared to the host cell without the heterologous polynucleotide that encodes the carbonic anhydrase, when cultivated under the same conditions.

[32] A composition comprising the recombinant host cell of any one of paragraphs [1]-[31].

[33] The composition of paragraph [32], comprising a fermentable medium.

[34] The composition of paragraph [32] or [33], further comprising a C4-dicarboxylic acid.

[35] The composition of any one of paragraphs [32]-[34], wherein the C4-dicarboxylic acid is at a titer greater than about 10 g/L, e.g., greater than about 25 g/L, 50 g/L, 75 g/L, 100 g/L, 125 g/L, 150 g/L, 160 g/L, 170 g/L, 180 g/L, 190 g/L, 200 g/L, 210 g/L, 225 g/L, 250 g/L, 275 g/L, 300 g/L, 325 g/L, 350 g/L, 400 g/L, or 500 g/L; or between about 10 g/L and about 500 g/L, e.g., between about 50 g/L and about 350 g/L, about 100 g/L and about 325 g/L, about 150 g/L and about 300 g/L, about 175 g/L and about 275 g/L, or about 190 g/L and about 250 g/L.

[36] A method of producing a C4-dicarboxylic acid, comprising:

(a) cultivating the recombinant host cell of any one of paragraphs 1-31 in a medium under suitable conditions to produce the C4-dicarboxylic acid; and (b) recovering the C4-dicarboxylic acid.

[37] The method of paragraph [36], wherein the medium is a fermentable medium.

[38] The method of paragraph [36] or [37], wherein the C4-dicarboxylic acid is at a titer greater than about 10 g/L, e.g., greater than about 25 g/L, 50 g/L, 75 g/L, 100 g/L, 125 g/L, 150 g/L, 160 g/L, 170 g/L, 180 g/L, 190 g/L, 200 g/L, 210 g/L, 225 g/L, 250 g/L, 275 g/L, 300 g/L, 325 g/L, 350 g/L, 400 g/L, or 500 g/L; or between about 10 g/L and about 500 g/L, e.g., between about 50 g/L and about 350 g/L, about 100 g/L and about 325 g/L, about 150 g/L and about 300 g/L, about 175 g/L and about 275 g/L, or about 190 g/L and about 250 g/L.

[39] The method of any one of paragraphs [36]-[38], wherein the amount of the produced C4-dicarboxylic acid is at least 5%, e.g., at least 10%, at least 15%, at least 20%, at least 25%, at least 30%, at least 50%, or at least 100% greater compared to cultivating the host cell without the polynucleotide that encodes the carbonic anhydrase under the same conditions.

What is claimed is:

1. A recombinant host cell comprising a heterologous polynucleotide that encodes a carbonic anhydrase, wherein the heterologous polynucleotide:
   (a) encodes a carbonic anhydrase having at least 95% sequence identity to SEQ ID NO: 55;
   (b) hybridizes under high stringency conditions with (i) the full-length complementary strand of SEQ ID NO: 54, or (ii) the full-length complementary strand of the cDNA sequence of SEQ ID NO: 54; or
   (c) has at least 95% sequence identity to SEQ ID NO: 54 or the cDNA sequence of SEQ ID NO: 54;
   wherein high stringency conditions are defined as prehybridization and hybridization at 42° C. in 5×SSPE, 0.3% SDS, 200 micrograms/mL sheared and denatured salmon sperm DNA, and 50% formamide for 12 to 24 hours, and washing three times each for 15 minutes using 2×SSC, 0.2% SDS at 65° C.;
   and wherein the host cell is capable of producing a greater amount of C4-dicarboxylic acid compared to the host cell without the heterologous polynucleotide when cultivated under the same conditions.

2. The recombinant host cell of claim 1, wherein the heterologous polynucleotide encodes a carbonic anhydrase having at least 95% sequence identity to SEQ ID NO: 55.

3. The recombinant host cell of claim 1, wherein the heterologous polynucleotide encodes a carbonic anhydrase that comprises or consists of SEQ ID NO: 55.

4. The recombinant host cell of claim 1, wherein the heterologous polynucleotide hybridizes under high stringency conditions with (i) the full-length complementary strand of SEQ ID NO: 54, or (ii) the full-length complementary strand of the cDNA sequence of SEQ ID NO: 54; wherein high stringency conditions are defined as prehybridization and hybridization at 42° C. in 5×SSPE, 0.3% SDS, 200 micrograms/mL sheared and denatured salmon sperm DNA, and 50% formamide for 12 to 24 hours, and washing three times each for 15 minutes using 2×SSC, 0.2% SDS at 65° C.

5. The recombinant host cell of claim 1, wherein the heterologous polynucleotide has at least 95% sequence identity to SEQ ID NO: 54 or the cDNA sequence of SEQ ID NO: 54.

6. The recombinant host cell of claim 1, wherein the heterologous polynucleotide comprises or consists of the sequence of SEQ ID NO: 54 or the cDNA sequence of SEQ ID NO: 54.

7. The recombinant host cell of claim 1, further comprising a heterologous polynucleotide that encodes a bicarbonate transporter.

8. The recombinant host cell of claim 1, further comprising a heterologous polynucleotide that encodes a C4-dicarboxylic acid transporter.

9. The recombinant host cell of claim 1, further comprising a heterologous polynucleotide that encodes a malate dehydrogenase.

10. The recombinant host cell of claim 1, further comprising a heterologous polynucleotide that encodes a pyruvate carboxylase.

11. The recombinant host cell of claim 1, wherein the host cell is a filamentous fungal host cell.

12. The recombinant host cell of claim 11, wherein the host cell is selected from the group consisting of an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Rhizopus, Schizophyllum, Talaromyces, Thermoascus, Thielavia, Tolypocladium, Trametes,* and *Trichoderma*.

13. The recombinant host cell of claim 12, wherein the host cell is an *Aspergillus* host cell.

14. The recombinant host cell of claim 13, wherein the host cell is an *Aspergillus oryzae* host cell.

15. The recombinant host cell of claim 1, wherein the C4-dicarboxylic acid is malic acid.

16. The recombinant host cell of claim 1, wherein the host cell is capable of producing a greater amount of the C4-dicarboxylic acid by at least 10% compared to the host cell without the heterologous polynucleotide that encodes the carbonic anhydrase, when cultivated under the same conditions.

17. The recombinant host cell of claim 1, wherein the host cell is capable of producing a greater amount of the C4-dicarboxylic acid by at least 50% compared to the host cell without the heterologous polynucleotide that encodes the carbonic anhydrase, when cultivated under the same conditions.

18. A method of producing a C4-dicarboxylic acid, comprising:
    (a) cultivating the recombinant host cell of claim 1 in a medium under suitable conditions to produce the C4-dicarboxylic acid; and
    (b) recovering the C4-dicarboxylic acid.

19. The method of claim 18, wherein the C4-dicarboxylic acid is malic acid.

20. The recombinant host cell of claim 1, wherein the heterologous polynucleotide encodes a carbonic anhydrase having at least 97% sequence identity to SEQ ID NO: 55.

21. The recombinant host cell of claim 1, wherein the heterologous polynucleotide encodes a carbonic anhydrase having at least 98% sequence identity to SEQ ID NO: 55.

22. The recombinant host cell of claim 1, wherein the heterologous polynucleotide encodes a carbonic anhydrase having at least 99% sequence identity to SEQ ID NO: 55.

23. The recombinant host cell of claim 1, wherein the heterologous polynucleotide hybridizes under very high stringency conditions with (i) the full-length complementary strand of SEQ ID NO: 54, or (ii) the full-length complementary strand of the cDNA sequence of SEQ ID NO: 54; wherein very high stringency conditions are defined as prehebridization and hybridization at 42° C. in 5×SSPE, 0.3% SDS, 200 micrograms/mL sheared and denatured salmon sperm DNA, and 50% formamide for 12 to 24 hours, and washing three times each for 15 minutes using 2×SSC, 0.2% SDS at 70° C.

24. The recombinant host cell of claim 1, wherein the heterologous polynucleotide has at least 97% sequence identity to SEQ ID NO: 54 or the cDNA sequence of SEQ ID NO: 54.

25. The recombinant host cell of claim 1, wherein the heterologous polynucleotide has at least 98% sequence identity to SEQ ID NO: 54 or the cDNA sequence of SEQ ID NO: 54.

26. The recombinant host cell of claim 1, wherein the heterologous polynucleotide has at least 99% sequence identity to SEQ ID NO: 54 or the cDNA sequence of SEQ ID NO: 54.

27. The recombinant host cell of claim 1, wherein the heterologous polynucleotide is operably linked to a promoter foreign to the polynucleotide.

28. A recombinant *Aspergillus oryzae* host cell comprising a heterologous polynucleotide that encodes a carbonic anhydrase, wherein:
    the heterologous polynucleotide is operably linked to a promoter foreign to the polynucleotide;
    the heterologous polynucleotide encodes a carbonic anhydrase having at least 95% sequence identity to SEQ ID NO: 55; and
    the host cell is capable of producing a greater amount of malic acid compared to the host cell without the heterologous polynucleotide when cultivated under the same conditions.

* * * * *

SEQUENCE LISTING

```
<160> NUMBER OF SEQ ID NOS: 68

<210> SEQ ID NO 1
<211> LENGTH: 2503
<212> TYPE: DNA
<213> ORGANISM: Aspergillus oryzae

<400> SEQUENCE: 1
atggaatcca gcgctgtaca ggagccgact caacagcgct ctttgcggga tcgcattttt      60
aacctctttc gtacctcttc ctcaaatgat gccccgggtc ttccggcaag actcgtaacc     120
gctgagagcg cagcgcaaaa cgaagggtcg gcgttaatct atccgccacg ggagcctgat     180
gcaaggactc gtcttctcga atcgtacgat cgcggggaac gtggtctgag gaactccggc     240
gttcatggga cttttctctc acgacctgaa caggaagaaa tccaaaaatg ggatgcaagc     300
tctttgcaga atgctggtaa cgaagaaaga tctcagtccc caggaggagc agacggccat     360
attgggtctc ccggcgacgt ctcaggatac ccacagggac cagagaatat accatcgcta     420
gactcctctt tcacagcatt gcacatgaag aatcataaat ctctgtaggt ttataatcac     480
gttcgccctg ctttctaaca caattgttat ctccatcgtg gagacaacta acgttcatca     540
aggtatatat cttactacat cccattttc aattggatta ctcaataccg gtggtcgtac      600
attcgaggtg atttggttgc tgcgacaacc attgcgtcca tctatatccc tatggctttg     660
```

```
tccttatcct caaatctcgc ccacgcacct cctatcaatg gcctctactc ttttgtgatc    720 aacccttttca tctatgcgat cttcgggagc agcccgctgt taatagtggg cccagaagca    780
gcaggctcct tgcttactgg cacgattgtc aaaactagtg tcagaccagg cccatctggt    840
gaggacgacg aagtagcgaa tgccatcgtg gtcggcatag ccactgcaat ggcgggcgcc    900
atgatactga tcgctgggct tacacggctg ggatttctgg acaatgtgct gagccggccc    960
tttcttaggg gtttcattac agcgatcggt tttgtgattt tgtggatca actcatcccc    1020 gaagtcggat tgaccgagct agcaaaggaa gctggtgtta cccatgggac tacagttgac    1080
aagctcatgt tccttataag aaacatagga ggttgccatg cgcttacaac cgcggtggct    1140
tttgggagct ttgctattat aatggtattt cggttagtgt tggtgactcg gaagcctggt    1200
gcttagactg attaccatta caggactctc aagaaaatgc tccagccgcg gtatcctcag    1260
gtgatttatc ttccggaccg aattctcgta gttattcttt cagccgtcct gacatggcat    1320
cttggttggg atgacaaagg gttggagatt cttgggccct tgaaacaaaa tgccaatggc    1380 cttttttgcgt tcaaatggcc tttccagttt agccagatga agcatgtacg cgctgcaatg    1440
agtacttctt tcgtcatcgc gttacttggc ttttttcgagt cttctgttgc cgccaaggga    1500
cttagtggcg aggccagaca agaaggtgtc cagggaatgc ctgtcagtgc taacagagag    1560
atggtggcgc tgggtcttgc taatactgtg gggggctgtt tcatggcgct tcctgcgttt    1620
ggtggctatg caagaagcaa agtcaacgct tcaactggag ctcggtctcc gatgagcagc    1680 atttttcctga gcattattac ctttgtttgt atcatggtgc ttttgccgta cttatactat    1740
cttccggtga gtctcgaccc caaatacttc cgagcgaagg ctgagaaaat atgttgcaat    1800
aattcagaaa gccgttcttt cttctatgat atctgtcgtc gcattcagtc tcattgaaga    1860
atgtcctcac gacgtggctt tctttatccg actgcgcgga tggacggagc tagccctaat    1920
gcttctcatc tttgtctcga ctattttcta ttctctagag ctgggaattg cccttggtat    1980
tggcctttct atcttgatcc ttattcgcca ttctacgcag cctcggatcc aaattctggg    2040
taagatagca ggcactaccg accgtttcga taacgctgaa ctccacccc g agagcgttga    2100 gttaatcgaa ggcgcgctta tgttaagat cccggaaccg ctcacctttg ccaatactgg    2160
tgagctcaag aatcgtcttc ggcggttgga attatatggc agtagccgag cgcacccttc    2220
tcttcccccc acgcgcaccc ccgaacataa caagaatatt atatttgatg ttcatggtgt    2280
tactagcatc gatggttccg gtacgcaagt cttatatgag attgtggacg gatatgcaga    2340 ccaggggggtc agcgtcttct tctgccgcgt cgcaactcgc aatgttttcc gcatgtttga    2400
acgaagtgga attgtggaac gatgcggtgg gataacgcac ttcgttcatg gtgtcgacga    2460
agccctccgc cttgccgaat cggaagacga gattgaaatc tga                       2503
```

<210> SEQ ID NO 2
<211> LENGTH: 770
<212> TYPE: PRT
<213> ORGANISM: Aspergillus oryzae

<400> SEQUENCE: 2

```
Met Glu Ser Ser Ala Val Gln Glu Pro Thr Gln Gln Arg Ser Leu Arg
1               5                   10                  15

Asp Arg Ile Phe Asn Leu Phe Arg Thr Ser Ser Ser Asn Asp Ala Pro
            20                  25                  30

Gly Leu Pro Ala Arg Leu Val Thr Ala Glu Ser Ala Ala Gln Asn Glu
        35                  40                  45
```

```
Gly Ser Ala Leu Ile Tyr Pro Pro Arg Glu Pro Asp Ala Arg Thr Arg
            50                  55                  60

Leu Leu Glu Ser Tyr Asp Arg Gly Glu Arg Gly Leu Arg Asn Ser Gly
 65                  70                  75                  80

Val His Gly Thr Phe Ser Ser Arg Pro Glu Gln Glu Glu Ile Gln Lys
                    85                  90                  95

Trp Asp Ala Ser Ser Leu Gln Asn Ala Gly Asn Glu Glu Arg Ser Gln
                100                 105                 110

Ser Pro Gly Gly Ala Asp Gly His Ile Gly Ser Pro Gly Asp Val Ser
            115                 120                 125

Gly Tyr Pro Gln Gly Pro Glu Asn Ile Pro Ser Leu Asp Ser Ser Phe
130                 135                 140

Thr Ala Leu His Met Lys Asn His Lys Ser Leu Tyr Ile Ser Tyr Tyr
145                 150                 155                 160

Ile Pro Phe Phe Asn Trp Ile Thr Gln Tyr Arg Trp Ser Tyr Ile Arg
                165                 170                 175

Gly Asp Leu Val Ala Ala Thr Thr Ile Ala Ser Ile Tyr Ile Pro Met
            180                 185                 190

Ala Leu Ser Leu Ser Ser Asn Leu Ala His Ala Pro Pro Ile Asn Gly
            195                 200                 205

Leu Tyr Ser Phe Val Ile Asn Pro Phe Ile Tyr Ala Ile Phe Gly Ser
210                 215                 220

Ser Pro Leu Leu Ile Val Gly Pro Glu Ala Ala Gly Ser Leu Leu Thr
225                 230                 235                 240

Gly Thr Ile Val Lys Thr Ser Val Arg Pro Gly Pro Ser Gly Glu Asp
                245                 250                 255

Asp Glu Val Ala Asn Ala Ile Val Val Gly Ile Ala Thr Ala Met Ala
            260                 265                 270

Gly Ala Met Ile Leu Ile Ala Gly Leu Thr Arg Leu Gly Phe Leu Asp
            275                 280                 285

Asn Val Leu Ser Arg Pro Phe Leu Arg Gly Phe Ile Thr Ala Ile Gly
            290                 295                 300

Phe Val Ile Phe Val Asp Gln Leu Ile Pro Glu Val Gly Leu Thr Glu
305                 310                 315                 320

Leu Ala Lys Glu Ala Gly Val Thr His Gly Thr Thr Val Asp Lys Leu
                325                 330                 335

Met Phe Leu Ile Arg Asn Ile Gly Gly Cys His Ala Leu Thr Thr Ala
                340                 345                 350

Val Ala Phe Gly Ser Phe Ala Ile Ile Met Val Phe Arg Thr Leu Lys
            355                 360                 365

Lys Met Leu Gln Pro Arg Tyr Pro Gln Val Ile Tyr Leu Pro Asp Arg
370                 375                 380

Ile Leu Val Val Ile Leu Ser Ala Val Leu Thr Trp His Leu Gly Trp
385                 390                 395                 400

Asp Asp Lys Gly Leu Glu Ile Leu Gly Pro Leu Lys Gln Asn Ala Asn
                405                 410                 415

Gly Leu Phe Ala Phe Lys Trp Pro Phe Gln Phe Ser Gln Met Lys His
            420                 425                 430

Val Arg Ala Ala Met Ser Thr Ser Phe Val Ile Ala Leu Leu Gly Phe
            435                 440                 445

Phe Glu Ser Ser Val Ala Ala Lys Gly Leu Ser Gly Glu Ala Arg Gln
450                 455                 460

Glu Gly Val Gln Gly Met Pro Val Ser Ala Asn Arg Glu Met Val Ala
465                 470                 475                 480
```

-continued

```
Leu Gly Leu Ala Asn Thr Val Gly Gly Cys Phe Met Ala Leu Pro Ala
                485                 490                 495
Phe Gly Gly Tyr Ala Arg Ser Lys Val Asn Ala Ser Thr Gly Ala Arg
            500                 505                 510
Ser Pro Met Ser Ser Ile Phe Leu Ser Ile Ile Thr Phe Val Cys Ile
        515                 520                 525
Met Val Leu Leu Pro Tyr Leu Tyr Tyr Leu Pro Lys Ala Val Leu Ser
    530                 535                 540
Ser Met Ile Ser Val Val Ala Phe Ser Leu Ile Glu Glu Cys Pro His
545                 550                 555                 560
Asp Val Ala Phe Phe Ile Arg Leu Arg Gly Trp Thr Glu Leu Ala Leu
                565                 570                 575
Met Leu Leu Ile Phe Val Ser Thr Ile Phe Tyr Ser Leu Glu Leu Gly
            580                 585                 590
Ile Ala Leu Gly Ile Gly Leu Ser Ile Leu Ile Leu Ile Arg His Ser
        595                 600                 605
Thr Gln Pro Arg Ile Gln Ile Leu Gly Lys Ile Ala Gly Thr Thr Asp
    610                 615                 620
Arg Phe Asp Asn Ala Glu Leu His Pro Glu Ser Val Glu Leu Ile Glu
625                 630                 635                 640
Gly Ala Leu Ile Val Lys Ile Pro Glu Pro Leu Thr Phe Ala Asn Thr
                645                 650                 655
Gly Glu Leu Lys Asn Arg Leu Arg Arg Leu Glu Leu Tyr Gly Ser Ser
            660                 665                 670
Arg Ala His Pro Ser Leu Pro Pro Thr Arg Thr Pro Glu His Asn Lys
        675                 680                 685
Asn Ile Ile Phe Asp Val His Gly Val Thr Ser Ile Asp Gly Ser Gly
    690                 695                 700
Thr Gln Val Leu Tyr Glu Ile Val Asp Gly Tyr Ala Asp Gln Gly Val
705                 710                 715                 720
Ser Val Phe Phe Cys Arg Val Ala Thr Arg Asn Val Phe Arg Met Phe
                725                 730                 735
Glu Arg Ser Gly Ile Val Glu Arg Cys Gly Gly Ile Thr His Phe Val
            740                 745                 750
His Gly Val Asp Glu Ala Leu Arg Leu Ala Glu Ser Glu Asp Glu Ile
        755                 760                 765
Glu Ile
    770

<210> SEQ ID NO 3
<211> LENGTH: 2657
<212> TYPE: DNA
<213> ORGANISM: Aspergillus oryzae

<400> SEQUENCE: 3
atgccgggcg atctcaaaac caaaattggt cacggcgcgg ccaaggcctt ggggatcaag      60
atcccctacc gtgatcctct cggagttcat gctgacccag tcacacgagg cgagtcgatg     120
ttctccgtcg gaacgatcga cacatactcc tatctcgagc ccgaacccac tcccgctgaa     180
tggctgaagg aagtctgccc tagctggcat caggtgggcc gttatttta caaccttttc     240 cctttcctct cgtggattac gaggtacaac ttgcaatggt tgctgggaga tatgattgcc     300
ggtaagagcc tttccactgt gtttgatttg atcgacaagt agacaacata ctcattggaa     360
tgcaggcgtc acggtcggtg ctgtggtcgt tccgcaggga atggcctacg ctaaactggc     420
```

```
aaacctacct gtagagtatg gtctctattc ctcgttcatg ggtgttctca tttattggtt    480
ttttgccacc tcaaaggata tcaccattgg tgtaagtcat tctgcaccca tgtcagcatg    540
tatcttgcta atatagtatc ttccctgttc agccggtggc tgtcatgtct acccttacag    600
gtaagatagt tgccgaggcg caaacgaagc tcccagatgt cgaagggcat gtaatcgcct    660
cctgtttggc tatcatttgt ggagccgtgg tttgcgctat gggcctgctt cggctgggat    720
ttatcgtgga tttcattcct ctgccggcaa tttcagcttt catgacgggt tccgccatca    780
atatctgctc cggacaggtc aaagacatgc tgggagagac ggccgacttc tcgacgaaag    840
attctaccta tctggttatc atcaacaccc tcaagcatct tccctccgca aaaatcgatg    900
ccgccatggg tgtcagtgct ttagctatgc tgtacattat ccgttcgggt tgcaattatg    960
gcgcgaagaa gttcccccgt catgccaagg tttggttctt cgtttcgact ttgcgcacag   1020
tgttcgtgat cttgttctat acgatgatca gtgccgctgt gaacttgcac cggcggtcta   1080
acccgcggtt caagctcctg ggtaaagttc ctcgtggttt ccaacatgcg gctgtccctc   1140
aggtaaattc gaggatcatc agcgcatttg ctagcgaact tcctgcttcg attattgtcc   1200
tgcttatcga acacatcgct atctcgaaat cctttggccg tgtcaacaac tacacaattg   1260
atccctctca ggagctggtt gctattggtg tgtcgaactt gcttggaccg ttccttggtg   1320
gttacccagc gactggatcg ttctcccgaa ctgcaatcaa atcgaaagcg ggtgtccgca   1380
ccccacttgc cggtgttatt actgcggttg ttgtcctcct cgccatttac gctctgcccg   1440
ctgtcttctt ttacatcccg aaagcttccc ttgctggtgt catcattcat gcagtcggtg   1500
acctcattac cccaccaaac accgtttacc agttctggcg cgtgtcccct ctggatgcga   1560
tcattttctt tatcggtgtt atcgtgactg tcttcaccac gattgagatc ggcatttact   1620
gtaccgtttg tgtgtctgtt gccattctgc tgttccgcgt cgccaaggcc cgcggtcaat   1680
tcttaggaag agtcactatc cactcggtga tcggtgacca tctggtacag gatgatggga   1740
aatatgggtc tgccaactcc cctaatgctg ccagcgatga caaagatgaa ttgagccggt   1800
ctatcttctt gcctatcaac cacacggacg gatcgaatcc cgatgtcgag gtgcagcaac   1860
cttatcctgg tatcttcatc taccgattct cggaaggatt caactacccc aatgccaatc   1920
actacaccga ttatttggtc cagactatct tcaagcatac acgtcgcaca aatccgttct   1980
cctacggtaa accgggtgat cggccatgga ataatcctgg ccctcgcagg ggcaagtctg   2040
aagatgacga gtcgcatttg cccttactgc aggctgtcat tcttgacttc tcatccgtca   2100
acaatgttga tgtgacctcg gtccagaacc tcatcgatgt ccgcaatcaa ctcgacctct   2160
acgcttcgcc taagactgtg cagtggcact tgctcatat taacaaccgc tggacgaaac   2220
gagcccttgc agcagcaggt ttcggcttcc catctccgga ctcggatgaa ggattccaga   2280
gatggaagcc aattttcagc gtggctgaga tcgaaggcag tgcctctgcc gcagctcatg   2340
cagagatggt gaacaacaga cacacccagc ataacatcaa gagcgaagac ctcgagcatg   2400
gcctcaagca cgattcagag accaccgagc gtgagacaca cggcatcgaa gaatcctccg   2460
atgccagcag cacccgggag acaagttgc aacgggacct gaaggatagc aaggcttacc    2520
gcagtcgccg aagggtcgct atggtgcagg gcctcaaccg gccattcttc cacatcgacc   2580
tgactagtgc actgcagagt gccttggcca acgcgggcga gcagccggac cctaaaatga   2640
atgtccttga tgcatag                                                  2657
```

<210> SEQ ID NO 4
<211> LENGTH: 843
<212> TYPE: PRT

<213> ORGANISM: Aspergillus oryzae

<400> SEQUENCE: 4

| | | | | | | | | | | | | | | |
|---|---|---|---|---|---|---|---|---|---|---|---|---|---|---|
| Met | Pro | Gly | Asp | Leu | Lys | Thr | Lys | Ile | Gly | His | Gly | Ala | Ala | Lys | Ala |
| 1 | | | | 5 | | | | | 10 | | | | | 15 | |
| Leu | Gly | Ile | Lys | Ile | Pro | Tyr | Arg | Asp | Pro | Leu | Gly | Val | His | Ala | Asp |
| | | | 20 | | | | | 25 | | | | | 30 | | |
| Pro | Val | Thr | Arg | Gly | Glu | Ser | Met | Phe | Ser | Val | Gly | Thr | Ile | Asp | Thr |
| | | 35 | | | | | 40 | | | | | 45 | | | |
| Tyr | Ser | Tyr | Leu | Glu | Pro | Glu | Pro | Thr | Pro | Ala | Glu | Trp | Leu | Lys | Glu |
| | 50 | | | | | 55 | | | | | 60 | | | | |
| Val | Cys | Pro | Ser | Trp | His | Gln | Val | Gly | Arg | Tyr | Phe | Tyr | Asn | Leu | Phe |
| 65 | | | | | 70 | | | | | 75 | | | | | 80 |
| Pro | Phe | Leu | Ser | Trp | Ile | Thr | Arg | Tyr | Asn | Leu | Gln | Trp | Leu | Leu | Gly |
| | | | | 85 | | | | | 90 | | | | | 95 | |
| Asp | Met | Ile | Ala | Gly | Val | Thr | Val | Gly | Ala | Val | Val | Pro | Gln | Gly |
| | | | 100 | | | | | 105 | | | | | 110 | | |
| Met | Ala | Tyr | Ala | Lys | Leu | Ala | Asn | Leu | Pro | Val | Glu | Tyr | Gly | Leu | Tyr |
| | | | 115 | | | | | 120 | | | | | 125 | | |
| Ser | Ser | Phe | Met | Gly | Val | Leu | Ile | Tyr | Trp | Phe | Phe | Ala | Thr | Ser | Lys |
| | 130 | | | | | 135 | | | | | 140 | | | | |
| Asp | Ile | Thr | Ile | Gly | Pro | Val | Ala | Val | Met | Ser | Thr | Leu | Thr | Gly | Lys |
| 145 | | | | | 150 | | | | | 155 | | | | | 160 |
| Ile | Val | Ala | Glu | Ala | Gln | Thr | Lys | Leu | Pro | Asp | Val | Glu | Gly | His | Val |
| | | | | 165 | | | | | 170 | | | | | 175 | |
| Ile | Ala | Ser | Cys | Leu | Ala | Ile | Ile | Cys | Gly | Ala | Val | Val | Cys | Ala | Met |
| | | | 180 | | | | | 185 | | | | | 190 | | |
| Gly | Leu | Leu | Arg | Leu | Gly | Phe | Ile | Val | Asp | Phe | Ile | Pro | Leu | Pro | Ala |
| | | | 195 | | | | | 200 | | | | | 205 | | |
| Ile | Ser | Ala | Phe | Met | Thr | Gly | Ser | Ala | Ile | Asn | Ile | Cys | Ser | Gly | Gln |
| | 210 | | | | | 215 | | | | | 220 | | | | |
| Val | Lys | Asp | Met | Leu | Gly | Glu | Thr | Ala | Asp | Phe | Ser | Thr | Lys | Asp | Ser |
| 225 | | | | | 230 | | | | | 235 | | | | | 240 |
| Thr | Tyr | Leu | Val | Ile | Ile | Asn | Thr | Leu | Lys | His | Leu | Pro | Ser | Ala | Lys |
| | | | | 245 | | | | | 250 | | | | | 255 | |
| Ile | Asp | Ala | Ala | Met | Gly | Val | Ser | Ala | Leu | Ala | Met | Leu | Tyr | Ile | Ile |
| | | | 260 | | | | | 265 | | | | | 270 | | |
| Arg | Ser | Gly | Cys | Asn | Tyr | Gly | Ala | Lys | Lys | Phe | Pro | Arg | His | Ala | Lys |
| | | 275 | | | | | 280 | | | | | 285 | | | |
| Val | Trp | Phe | Phe | Val | Ser | Thr | Leu | Arg | Thr | Val | Phe | Val | Ile | Leu | Phe |
| | 290 | | | | | 295 | | | | | 300 | | | | |
| Tyr | Thr | Met | Ile | Ser | Ala | Ala | Val | Asn | Leu | His | Arg | Arg | Ser | Asn | Pro |
| 305 | | | | | 310 | | | | | 315 | | | | | 320 |
| Arg | Phe | Lys | Leu | Leu | Gly | Lys | Val | Pro | Arg | Gly | Phe | Gln | His | Ala | Ala |
| | | | | 325 | | | | | 330 | | | | | 335 | |
| Val | Pro | Gln | Val | Asn | Ser | Arg | Ile | Ile | Ser | Phe | Ala | Ser | Glu | Leu |
| | | | 340 | | | | | 345 | | | | | 350 | | |
| Pro | Ala | Ser | Ile | Ile | Val | Leu | Leu | Ile | Glu | His | Ile | Ala | Ile | Ser | Lys |
| | | | 355 | | | | | 360 | | | | | 365 | | |
| Ser | Phe | Gly | Arg | Val | Asn | Asn | Tyr | Thr | Ile | Asp | Pro | Ser | Gln | Glu | Leu |
| | 370 | | | | | 375 | | | | | 380 | | | | |
| Val | Ala | Ile | Gly | Val | Ser | Asn | Leu | Leu | Gly | Pro | Phe | Leu | Gly | Gly | Tyr |
| 385 | | | | | 390 | | | | | 395 | | | | | 400 |
| Pro | Ala | Thr | Gly | Ser | Phe | Ser | Arg | Thr | Ala | Ile | Lys | Ser | Lys | Ala | Gly |

```
                405                 410                 415
Val Arg Thr Pro Leu Ala Gly Val Ile Thr Ala Val Val Leu Leu
            420                 425                 430

Ala Ile Tyr Ala Leu Pro Ala Val Phe Phe Tyr Ile Pro Lys Ala Ser
            435                 440                 445

Leu Ala Gly Val Ile Ile His Ala Val Gly Asp Leu Ile Thr Pro Pro
450                 455                 460

Asn Thr Val Tyr Gln Phe Trp Arg Val Ser Pro Leu Asp Ala Ile Ile
465                 470                 475                 480

Phe Phe Ile Gly Val Ile Val Thr Val Phe Thr Thr Ile Glu Ile Gly
            485                 490                 495

Ile Tyr Cys Thr Val Cys Val Ser Val Ala Ile Leu Leu Phe Arg Val
            500                 505                 510

Ala Lys Ala Arg Gly Gln Phe Leu Gly Arg Val Thr Ile His Ser Val
            515                 520                 525

Ile Gly Asp His Leu Val Gln Asp Asp Gly Lys Tyr Gly Ser Ala Asn
            530                 535                 540

Ser Pro Asn Ala Ala Ser Asp Asp Lys Asp Glu Leu Ser Arg Ser Ile
545                 550                 555                 560

Phe Leu Pro Ile Asn His Thr Asp Gly Ser Asn Pro Asp Val Glu Val
                565                 570                 575

Gln Gln Pro Tyr Pro Gly Ile Phe Ile Tyr Arg Phe Ser Glu Gly Phe
            580                 585                 590

Asn Tyr Pro Asn Ala Asn His Tyr Thr Asp Tyr Leu Val Gln Thr Ile
            595                 600                 605

Phe Lys His Thr Arg Arg Thr Asn Pro Phe Ser Tyr Gly Lys Pro Gly
            610                 615                 620

Asp Arg Pro Trp Asn Asn Pro Gly Pro Arg Arg Gly Lys Ser Glu Asp
625                 630                 635                 640

Asp Glu Ser His Leu Pro Leu Leu Gln Ala Val Ile Leu Asp Phe Ser
                645                 650                 655

Ser Val Asn Asn Val Asp Val Thr Ser Val Gln Asn Leu Ile Asp Val
            660                 665                 670

Arg Asn Gln Leu Asp Leu Tyr Ala Ser Pro Lys Thr Val Gln Trp His
            675                 680                 685

Phe Ala His Ile Asn Asn Arg Trp Thr Lys Arg Ala Leu Ala Ala Ala
            690                 695                 700

Gly Phe Gly Phe Pro Ser Pro Asp Ser Asp Glu Gly Phe Gln Arg Trp
705                 710                 715                 720

Lys Pro Ile Phe Ser Val Ala Glu Ile Glu Gly Ser Ala Ser Ala Ala
                725                 730                 735

Ala His Ala Glu Met Val Asn Asn Arg His Thr Gln His Asn Ile Lys
            740                 745                 750

Ser Glu Asp Leu Glu His Gly Leu Lys His Asp Ser Gly Thr Thr Glu
            755                 760                 765

Arg Glu Thr His Gly Ile Glu Glu Ser Ser Asp Ala Ser Ser Thr Arg
            770                 775                 780

Glu Asp Lys Leu Gln Arg Asp Leu Lys Asp Ser Lys Ala Tyr Arg Ser
785                 790                 795                 800

Arg Arg Arg Val Ala Met Val Gln Gly Leu Asn Arg Pro Phe Phe His
                805                 810                 815

Ile Asp Leu Thr Ser Ala Leu Gln Ser Ala Leu Ala Asn Ala Gly Glu
            820                 825                 830
```

```
Gln Pro Asp Pro Lys Met Asn Val Leu Asp Ala
        835                 840
```

<210> SEQ ID NO 5
<211> LENGTH: 1257
<212> TYPE: DNA
<213> ORGANISM: Aspergillus aculeatus

<400> SEQUENCE: 5

```
atgcacgacc acagcactgg atctagtcca tacatctcgg acgtggaaac cttgaaccac     60
gcctgcgaga gtccgtcaa ccccgagacc aaagtctccc agcctcagga atctcccatt    120
atcagcaata atgaacatca ggagtttgtt aagctgggca tccgccaacg gctgcgtcat    180
ttcacctggg cctggtatac cctaaccatg agcgcaggtg gactggccct tcttctccgc    240
aaccagccgt atcaattcaa gggggttaag agatataggc tggtggtata catagccaat    300
ctcgtcttct ttactatcat cggctctctt atgatcacca ggtttgttct ttacaacaac    360
ctgatggact ctctccgcca cgaccgagaa ggtttcttct ttccaacctt ctggctctcc    420
atcgccacca tgattagtgg tctatctgcc tacttctcta ctgaagacac gcaccgcctc    480
aattatgctc tcgagggtct cttctgggcg tactgtatct tcacgtttgc ctcagcagtg    540
atccagtact cctttgtctt ctcctatcac acgttccctc tgcaaactat gatgccatca    600
tggatcttac cggcattccc tatcatgctg agcggaacca ttgcctctgc cgcttccagc    660
taccagcctg cggtgtctgc cacgcctatg attgttgccg gcatcacgtt ccagggactc    720
ggattctgca tcagcttcat gatgtacgcc cactacatcg ggcgtctgat ggagacgggc    780
atcccttcga gcgagcaccg tcctggtatg ttcatctgtg tcggccccc tgccttcacg    840
ctgctggcta tcatcggcat ggccaacggc cttcccgagg gcttcagtat cctgggcgat    900
ggtggcatgg acgaccgtca tcatgcgca gtactggccg tctgcgcggg catgttcctc    960
tgggctctga gcatttggtt cttctgtgtc gctctgggct cagttgtgcg ggcgcctccc   1020
catgatttcc acctcaactg gtgggctatg gtcttcccta caccggact cactctcgcc   1080
accatcaccc tggccaagtc actggacagt gccgcgttga atgggtggg cgtgggcatg   1140
tccctctgcg tgatctgcat gttcatcttc gtcttcgtga gcaccattag gctgttctc   1200
ttgaagagga tcatgtggcc aggtcgggat gaggatgtgt ccgagttgtt cgaatga     1257
```

<210> SEQ ID NO 6
<211> LENGTH: 418
<212> TYPE: PRT
<213> ORGANISM: Aspergillus aculeatus

<400> SEQUENCE: 6

```
Met His Asp His Ser Thr Gly Ser Ser Pro Tyr Ile Ser Asp Val Glu
1               5                   10                  15

Thr Leu Asn His Ala Cys Glu Lys Ser Val Asn Pro Glu Ala Lys Val
            20                  25                  30

Ser Gln Pro Gln Glu Ser Pro Ile Ile Ser Asn Asn Glu His Gln Glu
        35                  40                  45

Phe Val Lys Leu Gly Ile Arg Gln Arg Leu Arg His Phe Thr Trp Ala
    50                  55                  60

Trp Tyr Thr Leu Thr Met Ser Ala Gly Gly Leu Ala Leu Leu Leu Arg
65                  70                  75                  80

Asn Gln Pro Tyr Gln Phe Lys Gly Leu Lys Glu Ile Gly Leu Val Val
                85                  90                  95

Tyr Ile Ala Asn Leu Val Phe Phe Thr Ile Ile Gly Ser Leu Met Ile
```

```
                    100                 105                 110
Thr Arg Phe Val Leu Tyr Asn Asn Leu Met Asp Ser Leu Arg His Asp
                115                 120                 125
Arg Glu Gly Phe Phe Phe Pro Thr Phe Trp Leu Ser Ile Ala Thr Met
            130                 135                 140
Ile Ser Gly Leu Ser Ala Tyr Phe Ser Thr Glu Asp Thr His Arg Leu
145                 150                 155                 160
Asn Tyr Ala Leu Glu Gly Leu Phe Trp Ala Tyr Cys Ile Phe Thr Phe
                165                 170                 175
Ala Ser Ala Val Ile Gln Tyr Ser Phe Val Phe Ser Tyr His Thr Phe
            180                 185                 190
Pro Leu Gln Thr Met Met Pro Ser Trp Ile Leu Pro Ala Phe Pro Ile
            195                 200                 205
Met Leu Ser Gly Thr Ile Ala Ser Ala Ser Ser Tyr Gln Pro Ala
            210                 215                 220
Val Ser Ala Thr Pro Met Ile Val Ala Gly Ile Thr Phe Gln Gly Leu
225                 230                 235                 240
Gly Phe Cys Ile Ser Phe Met Met Tyr Ala His Tyr Ile Gly Arg Leu
                245                 250                 255
Met Glu Thr Gly Ile Pro Ser Ser Glu His Arg Pro Gly Met Phe Ile
            260                 265                 270
Cys Val Gly Pro Pro Ala Phe Thr Leu Leu Ala Ile Ile Gly Met Ala
            275                 280                 285
Asn Gly Leu Pro Glu Gly Phe Ser Ile Leu Gly Asp Gly Gly Met Asp
            290                 295                 300
Asp Arg His Ile Met Arg Val Leu Ala Val Cys Ala Gly Met Phe Leu
305                 310                 315                 320
Trp Ala Leu Ser Ile Trp Phe Phe Cys Val Ala Leu Gly Ser Val Val
                325                 330                 335
Arg Ala Pro Pro His Asp Phe His Leu Asn Trp Trp Ala Met Val Phe
            340                 345                 350
Pro Asn Thr Gly Leu Thr Leu Ala Thr Ile Thr Leu Ala Lys Ser Leu
            355                 360                 365
Asp Ser Ala Ala Leu Lys Trp Val Gly Val Gly Met Ser Leu Cys Val
            370                 375                 380
Ile Cys Met Phe Ile Phe Val Phe Val Ser Thr Val Arg Ala Val Leu
385                 390                 395                 400
Leu Lys Arg Ile Met Trp Pro Gly Arg Asp Glu Asp Val Ser Glu Leu
                405                 410                 415
Phe Glu

<210> SEQ ID NO 7
<211> LENGTH: 1430
<212> TYPE: DNA
<213> ORGANISM: Aspergillus oryzae

<400> SEQUENCE: 7
atggtcaaag ctggtgagtt agcaatcctt aacagatgac actctcatag gtactaactc      60
gaaacgttag cggtacttgg agcttctggt ggcattggcc aggtatggat atccccacgc     120
cttacaaccc tggtcacaat atgaccttgt tcgatactga ctatctccca agccactgtc     180
tctcctgttg aagacctgtc ccttagttga agagcttgct ctctacgatg ttgtgaacac     240
ccctggtgtt gctgctgatc tatcccacat ctcgtctatc gctgtacgtt actgccacaa     300
tgcgaattgc ccgatggaag aggcgaaaaa tggtatcttg cttacctggg cgattagaaa     360
```

```
atctctggtt ttctgcccaa agatgatggg ctgaagcagg cccttactgg tgctaatatt     420
gttgtcatcc cggctggtat tccccgtaag tccctaccct ttcgcattgc tcctcgtatg     480
ttcgctggtg gccagttttc tgatagttga taggcaagcc tggtatgacc cgtgacgacc     540
tcttcaagat caacgccggc atagtgcgag acttggtcaa gggtatcgcc gagttctgcc     600
ccaaggcctt tgttctggtt atctcaaacc ccgttaattc tactgttcct attgctgcag     660
aggtgctcaa agccgctggc gtctttgacc cgaagcgcct ctttggtgtc accacactgg     720
acgtcgttcg tgcagagact ttcacccaag agttctcggg ccagaaggat ccttctgctg     780
ttcaaatccc agttgttggt ggccactctg gagagaccat tgtccccctc ttcagcaaga     840
ctaccccgc aattcagata cccgaggaga agtatgacgc actgatccac cgtaggttgt     900
cccaaagaat ctcatgaata tcttgctgta agcactaact atgcttcagg cgtccaattt     960
ggtggagatg aggtggtcca agctaaggac ggtgctggtt ccgccacctt gtctatggcc    1020
tatgccggtt acaggtaggg atgctgcgta ccgtgagagc actcgcggct aacatgccat    1080
aggttcgctg agagtgtaat caaagcttca aagggtcaaa cgggtattgt cgagcctacc    1140
ttcgtctacc tgcctggaat tcccggcggt gatgagatcg ttaaggcaac tggcgtggaa    1200
ttcttctcta ctcttgtaac cttaggagta agattcatct cctcacagaa tcttcgttca    1260
tatcacgcca ggctaacgct attaaacaga ctaatgcgc agagaaggct agcaacgttc    1320
ttgagggcgt gaccgagaag gaaagaagc ttctcgaggc ttgcacgaaa ggccttaagg    1380
gtaatatcga gaaggcatc gacttcgtta agaacccacc accaaagtaa                1430

<210> SEQ ID NO 8
<211> LENGTH: 330
<212> TYPE: PRT
<213> ORGANISM: Aspergillus oryzae

<400> SEQUENCE: 8

Met Val Lys Ala Ala Val Leu Gly Ala Ser Gly Gly Ile Gly Gln Pro
1               5                   10                  15

Leu Ser Leu Leu Leu Lys Thr Cys Pro Leu Val Glu Glu Leu Ala Leu
            20                  25                  30

Tyr Asp Val Val Asn Thr Pro Gly Val Ala Ala Asp Leu Ser His Ile
        35                  40                  45

Ser Ser Ile Ala Lys Ile Ser Gly Phe Leu Pro Lys Asp Asp Gly Leu
    50                  55                  60

Lys Gln Ala Leu Thr Gly Ala Asn Ile Val Ile Pro Ala Gly Ile
65                  70                  75                  80

Pro Arg Lys Pro Gly Met Thr Arg Asp Asp Leu Phe Lys Ile Asn Ala
                85                  90                  95

Gly Ile Val Arg Asp Leu Val Lys Gly Ile Ala Glu Phe Cys Pro Lys
            100                 105                 110

Ala Phe Val Leu Val Ile Ser Asn Pro Val Asn Ser Thr Val Pro Ile
        115                 120                 125

Ala Ala Glu Val Leu Lys Ala Ala Gly Val Phe Asp Pro Lys Arg Leu
    130                 135                 140

Phe Gly Val Thr Thr Leu Asp Val Val Arg Ala Glu Thr Phe Thr Gln
145                 150                 155                 160

Glu Phe Ser Gly Gln Lys Asp Pro Ser Ala Val Gln Ile Pro Val Val
                165                 170                 175

Gly Gly His Ser Gly Glu Thr Ile Val Pro Leu Phe Ser Lys Thr Thr
            180                 185                 190
```

```
Pro Ala Ile Gln Ile Pro Glu Glu Lys Tyr Asp Ala Leu Ile His Arg
        195                 200                 205

Val Gln Phe Gly Gly Asp Glu Val Val Gln Ala Lys Asp Gly Ala Gly
    210                 215                 220

Ser Ala Thr Leu Ser Met Ala Tyr Ala Gly Tyr Arg Phe Ala Glu Ser
225                 230                 235                 240

Val Ile Lys Ala Ser Lys Gly Gln Thr Gly Ile Val Glu Pro Thr Phe
                245                 250                 255

Val Tyr Leu Pro Gly Ile Pro Gly Gly Asp Glu Ile Val Lys Ala Thr
                260                 265                 270

Gly Val Glu Phe Phe Ser Thr Leu Val Thr Leu Gly Thr Asn Gly Ala
                275                 280                 285

Glu Lys Ala Ser Asn Val Leu Glu Gly Val Thr Glu Lys Glu Lys Lys
        290                 295                 300

Leu Leu Glu Ala Cys Thr Lys Gly Leu Lys Gly Asn Ile Glu Lys Gly
305                 310                 315                 320

Ile Asp Phe Val Lys Asn Pro Pro Lys
                325                 330

<210> SEQ ID NO 9
<211> LENGTH: 3643
<212> TYPE: DNA
<213> ORGANISM: Aspergillus oryzae

<400> SEQUENCE: 9
atggcggctc cgtttcgtca gcctgaggag gcggtcgatg acaccgagtt catcgatgac        60
caccatgaac acctccgtga taccgtgcac catcggttgc gcgccaattc ctccattatg       120
cacttccaga agatcctcgt cgccaaccgt ggtgagatcc ccattcgtat cttcagaacg       180
gcccacgagc tgtcattgca gacggttgct atctactctc atgaggatcg actgtcaatg       240
caccgtcaaa aggccgatga ggcctacatg attggccacc gcggtcagta caccctgtc        300 ggtgcgtacc tggcgggcga tgagatcatc aagatcgccc tggagcacgg tgtccagctg       360
atccacccgg gctacggttt cttgtccgag aacgccgact cgcccgcaa ggttgagaac         420 gccggcattg tctttgtggg acccactccc gataccattg acagcttggg tgacaaggtg       480
tcggcccgtc ggctggccat taagtgcgag gtccctgtcg ttccgggtac ggagggcccc       540
gtcgagcgct atgaggaggt caaggcgttc acagacacct atggcttccc catcatcatc       600
aaggctgcct ttggcggtgg tggccgtggt atgcgtgtgg tccgtgacca ggccgagctg       660
cgtgactcgt cgagcgagc cacctctgag gcccgctccg ccttcggcaa tggtaccgtc         720
ttcgtcgagc gcttcctcga caaacccaag cacattgaag tccagcttct gggtgacagc       780
cacggcaacg ttgtccatct gtttgagcgt gactgctccg tgcagcgtcg tcaccagaag       840
gtcgttgagg ttgctccggc taaggacctg ccagccgatg tccgggaccg catcctggcc       900
gatgctgtga agctggccaa gtccgtcaac taccgtaacg ccggtacagc tgagttcctg       960
gtggaccagc agaaccgcca ctacttcatt gaaatcaatc ctcgtatcca agtcgagcac      1020
accatcaccg aagagattac tggtatcgat atcgtggctg cacagatcca gattgctgct      1080
ggtgcaagcc tcgagcaact gggcctgact caggaccgca ctccgcccg cggatttgcc       1140 attcaatgtc gtatcaccac ggaagatccc gccaaggggt ctctccggga tactggtaag      1200
attgaggttt atcgttccgc tggtggtaac ggtgtccgtc tggatggtgg taacggtttc       1260
gctggtgcta tcatcacccc tcactacgac tccatgctgg tcaagtgtac ctgccgtggt      1320
```

```
tcgacctatg aaatcgctcg tcgcaaggtt gtgcgtgcct tggtcgagtt ccgtattcgt    1380
ggtgtgaaga ccaacattcc cttcctgact tcgcttctga gccacccgac cttcgtcgat    1440
ggaaactgct ggaccacttt catcgacgac acccctgaat tgttctctct tgtcggcagt    1500
cagaaccgtg cccagaagct gctcgcatac ctcggcgatg tagctgtcaa cggtagtagc    1560
atcaagggcc aaattggcga gcccaagctc aagggtgatg tcatcaagcc gaagcttttc    1620
gatgccgagg gcaagccgct tgacgttccc gcccctgca ccaagggttg gaagcagatt     1680
ctggaccggg agggcccggc tgcctttgcg aaggccgtgc gtgccaacaa gggttgcttg    1740
atcatggata ctacctggcg tgacgcccac cagtctttgc tggccacccg tgtgcgtacc    1800
atcgacttgt tgaacatcgc ccatgagacc agctacgcct actccaatgc gtacagtttg    1860
gaatgctggg gtggtgctac cttcgatgtg gccatgcgtt tcctctatga ggaccctgg     1920 gaccgcctgc gcaagatgcg taaggctgtt cctaacatcc cattccagat gttgctccgt    1980
ggtgccaacg tgtcgcccta ctcttccctc ccagacaacg ccatctacca cttctgtaag    2040
caggctaaga agtgcggtgt cgacattttc cgtgttttcg acgccctcaa cgatgtcgat    2100
cagctcgagg tcggtatcaa ggctgttcat gctgccgagg gtgttgtcga ggccaccatg    2160
tgctacagcg gtgacatgct gaaccccac aagaagtaca acctggagta ctacatggcc     2220
ttggtggata agattgtagc catgaagcct cacatccttg gtatcaagga tatgccggt     2280 gtgctgaagc cccaggccgc tcgcctgttg gtgggctcca tccgtcagcg ctaccctgac    2340
cttcccatcc acgtccacac ccacgactcc gctggtactg gtgtagcttc catgattgcc    2400
tgtgcccagg cgggtgccga cgccgtggac gccgcgaccg acagcatgtc cggtatgacc    2460
tcccagccta gcattggtgc cattctggcc tctcttgagg gcactgagca agaccccggt    2520
ctcaacctcg cccacgtgcg cgctattgat agctactggg cacagctgcg cttgctctac    2580
tctcctttcg aggcgggtct cactggcccc gaccctgagg tctacgagca cgagatccct    2640
ggtggtcagt tgaccaacct tatcttccag gccagtcagc tcggcttggg ccagcagtgg    2700
gccgaaacca agaaggccta tgaggcggct aatgatttac tcggcgacat tgtaaaggtc    2760
actcccacct ccaaggtggt cggtgacttg gctcagttca tggtctcgaa caaactgact    2820
ccggaggatg ttgttgagcg tgctggtgag ctggacttcc ctggttctgt gctcgaattc    2880
ctcgaaggtc tcatgggaca gcccttcggt ggattccccg agccattgcg ctcccgcgcc    2940
ctgcgcgatc gccgcaagct cgagaagcgt ccaggtctct acctcgagcc tttggatttg    3000
gctaagatca gagccagat ccgtgagaag ttcggtgctg ctactgagta tgacgtggcc      3060
agctatgcca tgtatcccaa ggtcttcgag gactacaaga agttcgtcca gaagttcggt    3120
gatctctccg tcttgcccac acggtacttc ttggccaagc tgagattgg cgaggagttc      3180 cacgttgagc tggagaaggg taaggtgctc atcctgaagt tgttggccat cggccctctt    3240
tcagagcaga ctggtcagcg tgaggtcttc tacgaagtca acggtgaggt gcgccaggtc    3300
gctgttgatg acaacaaggc ttccgtggac aacacttcac gccctaaggc cgatgtgggt    3360
gacagcagcc aggtcggtgc tcctatgagc ggtgtggttg ttgaaatccg tgtccacgat    3420
ggtctggagg ttaagaaggg tgacccactt gccgtcctga gtgccatgaa gatggtaagt    3480
tcattccgaa tcattttct cactggtcaa ctacagatgc taacagctta tccaggaaat     3540
ggttatctct gctcctcaca gtggaaaggt ctccagcttg ctggtcaagg agggcgattc    3600
tgtggatggc caggatctcg tctgcaagat cgtcaaagcg taa                      3643
```

<210> SEQ ID NO 10

<211> LENGTH: 1193
<212> TYPE: PRT
<213> ORGANISM: Aspergillus oryzae

<400> SEQUENCE: 10

```
Met Ala Ala Pro Phe Arg Gln Pro Glu Glu Ala Val Asp Asp Thr Glu
1               5                   10                  15

Phe Ile Asp Asp His His Glu His Leu Arg Asp Thr Val His His Arg
            20                  25                  30

Leu Arg Ala Asn Ser Ser Ile Met His Phe Gln Lys Ile Leu Val Ala
        35                  40                  45

Asn Arg Gly Glu Ile Pro Ile Arg Ile Phe Arg Thr Ala His Glu Leu
    50                  55                  60

Ser Leu Gln Thr Val Ala Ile Tyr Ser His Glu Asp Arg Leu Ser Met
65                  70                  75                  80

His Arg Gln Lys Ala Asp Glu Ala Tyr Met Ile Gly His Arg Gly Gln
                85                  90                  95

Tyr Thr Pro Val Gly Ala Tyr Leu Ala Gly Asp Glu Ile Ile Lys Ile
            100                 105                 110

Ala Leu Glu His Gly Val Gln Leu Ile His Pro Gly Tyr Gly Phe Leu
        115                 120                 125

Ser Glu Asn Ala Asp Phe Ala Arg Lys Val Glu Asn Ala Gly Ile Val
    130                 135                 140

Phe Val Gly Pro Thr Pro Asp Thr Ile Asp Ser Leu Gly Asp Lys Val
145                 150                 155                 160

Ser Ala Arg Arg Leu Ala Ile Lys Cys Glu Val Pro Val Val Pro Gly
                165                 170                 175

Thr Glu Gly Pro Val Glu Arg Tyr Glu Glu Val Lys Ala Phe Thr Asp
            180                 185                 190

Thr Tyr Gly Phe Pro Ile Ile Ile Lys Ala Ala Phe Gly Gly Gly Gly
        195                 200                 205

Arg Gly Met Arg Val Val Arg Asp Gln Ala Glu Leu Arg Asp Ser Phe
    210                 215                 220

Glu Arg Ala Thr Ser Glu Ala Arg Ser Ala Phe Gly Asn Gly Thr Val
225                 230                 235                 240

Phe Val Glu Arg Phe Leu Asp Lys Pro Lys His Ile Glu Val Gln Leu
                245                 250                 255

Leu Gly Asp Ser His Gly Asn Val Val His Leu Phe Glu Arg Asp Cys
            260                 265                 270

Ser Val Gln Arg Arg His Gln Lys Val Val Glu Val Ala Pro Ala Lys
        275                 280                 285

Asp Leu Pro Ala Asp Val Arg Asp Arg Ile Leu Ala Asp Ala Val Lys
    290                 295                 300

Leu Ala Lys Ser Val Asn Tyr Arg Asn Ala Gly Thr Ala Glu Phe Leu
305                 310                 315                 320

Val Asp Gln Gln Asn Arg His Tyr Phe Ile Glu Ile Asn Pro Arg Ile
                325                 330                 335

Gln Val Glu His Thr Ile Thr Glu Glu Ile Thr Gly Ile Asp Ile Val
            340                 345                 350

Ala Ala Gln Ile Gln Ile Ala Ala Gly Ala Ser Leu Glu Gln Leu Gly
        355                 360                 365

Leu Thr Gln Asp Arg Ile Ser Ala Arg Gly Phe Ala Ile Gln Cys Arg
    370                 375                 380

Ile Thr Thr Glu Asp Pro Ala Lys Gly Phe Ser Pro Asp Thr Gly Lys
385                 390                 395                 400
```

```
Ile Glu Val Tyr Arg Ser Ala Gly Gly Asn Gly Val Arg Leu Asp Gly
            405                 410                 415

Gly Asn Gly Phe Ala Gly Ala Ile Ile Thr Pro His Tyr Asp Ser Met
            420                 425                 430

Leu Val Lys Cys Thr Cys Arg Gly Ser Thr Tyr Glu Ile Ala Arg Arg
            435                 440                 445

Lys Val Val Arg Ala Leu Val Glu Phe Arg Ile Arg Gly Val Lys Thr
450                 455                 460

Asn Ile Pro Phe Leu Thr Ser Leu Leu Ser His Pro Thr Phe Val Asp
465                 470                 475                 480

Gly Asn Cys Trp Thr Thr Phe Ile Asp Asp Thr Pro Glu Leu Phe Ser
                485                 490                 495

Leu Val Gly Ser Gln Asn Arg Ala Gln Lys Leu Leu Ala Tyr Leu Gly
            500                 505                 510

Asp Val Ala Val Asn Gly Ser Ser Ile Lys Gly Gln Ile Gly Glu Pro
            515                 520                 525

Lys Leu Lys Gly Asp Val Ile Lys Pro Lys Leu Phe Asp Ala Glu Gly
            530                 535                 540

Lys Pro Leu Asp Val Ser Ala Pro Cys Thr Lys Gly Trp Lys Gln Ile
545                 550                 555                 560

Leu Asp Arg Glu Gly Pro Ala Ala Phe Ala Lys Ala Val Arg Ala Asn
                565                 570                 575

Lys Gly Cys Leu Ile Met Asp Thr Thr Trp Arg Asp Ala His Gln Ser
            580                 585                 590

Leu Leu Ala Thr Arg Val Arg Thr Ile Asp Leu Leu Asn Ile Ala His
            595                 600                 605

Glu Thr Ser Tyr Ala Tyr Ser Asn Ala Tyr Ser Leu Glu Cys Trp Gly
            610                 615                 620

Gly Ala Thr Phe Asp Val Ala Met Arg Phe Leu Tyr Glu Asp Pro Trp
625                 630                 635                 640

Asp Arg Leu Arg Lys Met Arg Lys Ala Val Pro Asn Ile Pro Phe Gln
                645                 650                 655

Met Leu Leu Arg Gly Ala Asn Gly Val Ala Tyr Ser Ser Leu Pro Asp
            660                 665                 670

Asn Ala Ile Tyr His Phe Cys Lys Gln Ala Lys Lys Cys Gly Val Asp
            675                 680                 685

Ile Phe Arg Val Phe Asp Ala Leu Asn Asp Val Asp Gln Leu Glu Val
690                 695                 700

Gly Ile Lys Ala Val His Ala Ala Glu Gly Val Val Glu Ala Thr Met
705                 710                 715                 720

Cys Tyr Ser Gly Asp Met Leu Asn Pro His Lys Lys Tyr Asn Leu Glu
                725                 730                 735

Tyr Tyr Met Ala Leu Val Asp Lys Ile Val Ala Met Lys Pro His Ile
            740                 745                 750

Leu Gly Ile Lys Asp Met Ala Gly Val Leu Lys Pro Gln Ala Ala Arg
            755                 760                 765

Leu Leu Val Gly Ser Ile Arg Gln Arg Tyr Pro Asp Leu Pro Ile His
            770                 775                 780

Val His Thr His Asp Ser Ala Gly Thr Gly Val Ala Ser Met Ile Ala
785                 790                 795                 800

Cys Ala Gln Ala Gly Ala Asp Ala Val Asp Ala Ala Thr Asp Ser Met
                805                 810                 815

Ser Gly Met Thr Ser Gln Pro Ser Ile Gly Ala Ile Leu Ala Ser Leu
```

```
                      820              825              830
Glu Gly Thr Glu Gln Asp Pro Gly Leu Asn Leu Ala His Val Arg Ala
        835              840              845
Ile Asp Ser Tyr Trp Ala Gln Leu Arg Leu Tyr Ser Pro Phe Glu
    850              855              860
Ala Gly Leu Thr Gly Pro Asp Pro Glu Val Tyr Glu His Glu Ile Pro
865             870              875              880
Gly Gly Gln Leu Thr Asn Leu Ile Phe Gln Ala Ser Gln Leu Gly Leu
                885              890              895
Gly Gln Gln Trp Ala Glu Thr Lys Lys Ala Tyr Glu Ala Ala Asn Asp
            900              905              910
Leu Leu Gly Asp Ile Val Lys Val Thr Pro Thr Ser Lys Val Val Gly
            915              920              925
Asp Leu Ala Gln Phe Met Val Ser Asn Lys Leu Thr Pro Glu Asp Val
            930              935              940
Val Glu Arg Ala Gly Glu Leu Asp Phe Pro Gly Ser Val Leu Glu Phe
945             950              955              960
Leu Glu Gly Leu Met Gly Gln Pro Phe Gly Phe Pro Glu Pro Leu
                965              970              975
Arg Ser Arg Ala Leu Arg Asp Arg Arg Lys Leu Glu Lys Arg Pro Gly
            980              985              990
Leu Tyr Leu Glu Pro Leu Asp Leu  Ala Lys Ile Lys Ser  Gln Ile Arg
                995              1000             1005
Glu Lys  Phe Gly Ala Ala Thr  Glu Tyr Asp Val Ala  Ser Tyr Ala
    1010             1015             1020
Met Tyr Pro Lys Val Phe Glu  Asp Tyr Lys Lys Phe  Val Gln Lys
    1025             1030             1035
Phe Gly  Asp Leu Ser Val Leu  Pro Thr Arg Tyr Phe  Leu Ala Lys
    1040             1045             1050
Pro Glu  Ile Gly Glu Glu Phe  His Val Glu Leu Glu  Lys Gly Lys
    1055             1060             1065
Val Leu  Ile Leu Lys Leu Leu  Ala Ile Gly Pro Leu  Ser Glu Gln
    1070             1075             1080
Thr Gly  Gln Arg Glu Val Phe  Tyr Glu Val Asn Gly  Glu Val Arg
    1085             1090             1095
Gln Val  Ala Val Asp Asp Asn  Lys Ala Ser Val Asp  Asn Thr Ser
    1100             1105             1110
Arg Pro  Lys Ala Asp Val Gly  Asp Ser Ser Gln Val  Gly Ala Pro
    1115             1120             1125
Met Ser  Gly Val Val Val Glu  Ile Arg Val His Asp  Gly Leu Glu
    1130             1135             1140
Val Lys  Lys Gly Asp Pro Leu  Ala Val Leu Ser Ala  Met Lys Met
    1145             1150             1155
Glu Met  Val Ile Ser Ala Pro  His Ser Gly Lys Val  Ser Ser Leu
    1160             1165             1170
Leu Val  Lys Glu Gly Asp Ser  Val Asp Gly Gln Asp  Leu Val Cys
    1175             1180             1185
Lys Ile  Val Lys Ala
    1190

<210> SEQ ID NO 11
<211> LENGTH: 40
<212> TYPE: DNA
<213> ORGANISM: Aspergillus oryzae
```

-continued

<400> SEQUENCE: 11
gtgatagaac atcgtccata atggaatcca gcgctgtaca    40

<210> SEQ ID NO 12
<211> LENGTH: 40
<212> TYPE: DNA
<213> ORGANISM: Aspergillus oryzae

<400> SEQUENCE: 12
gtgtcagtca cctctagtta tcagatttca atctcgtctt    40

<210> SEQ ID NO 13
<211> LENGTH: 20
<212> TYPE: DNA
<213> ORGANISM: Aspergillus oryzae

<400> SEQUENCE: 13
gaacaggaag aaatccaaaa    20

<210> SEQ ID NO 14
<211> LENGTH: 20
<212> TYPE: DNA
<213> ORGANISM: Aspergillus oryzae

<400> SEQUENCE: 14
gtcggcatag ccactgcaat    20

<210> SEQ ID NO 15
<211> LENGTH: 20
<212> TYPE: DNA
<213> ORGANISM: Aspergillus oryzae

<400> SEQUENCE: 15
tgttgccgcc aagggactta    20

<210> SEQ ID NO 16
<211> LENGTH: 20
<212> TYPE: DNA
<213> ORGANISM: Aspergillus oryzae

<400> SEQUENCE: 16
ccgagagcgt tgagttaatc    20

<210> SEQ ID NO 17
<211> LENGTH: 20
<212> TYPE: DNA
<213> ORGANISM: Aspergillus oryzae

<400> SEQUENCE: 17
agcattaggg ctagctccgt    20

<210> SEQ ID NO 18
<211> LENGTH: 20
<212> TYPE: DNA
<213> ORGANISM: Aspergillus oryzae

<400> SEQUENCE: 18
ccaagatgcc atgtcaggac    20

<210> SEQ ID NO 19
<211> LENGTH: 20
<212> TYPE: DNA
<213> ORGANISM: Aspergillus oryzae

<400> SEQUENCE: 19
tcacaaaaga gtagaggcca                                              20

<210> SEQ ID NO 20
<211> LENGTH: 36
<212> TYPE: DNA
<213> ORGANISM: Aspergillus oryzae

<400> SEQUENCE: 20
tgtgatagaa catcgtccat aatgcacgac cacagc                            36

<210> SEQ ID NO 21
<211> LENGTH: 40
<212> TYPE: DNA
<213> ORGANISM: Aspergillus oryzae

<400> SEQUENCE: 21
gtgtcagtca cctctagtta tcattcgaac aactcggaca                        40

<210> SEQ ID NO 22
<211> LENGTH: 36
<212> TYPE: DNA
<213> ORGANISM: Aspergillus oryzae

<400> SEQUENCE: 22
agaacatcgt ccataatggt caaagctggt gagtta                            36

<210> SEQ ID NO 23
<211> LENGTH: 40
<212> TYPE: DNA
<213> ORGANISM: Aspergillus oryzae

<400> SEQUENCE: 23
gtgtcagtca cctctagtta ttactttggt ggtgggttct                        40

<210> SEQ ID NO 24
<211> LENGTH: 36
<212> TYPE: DNA
<213> ORGANISM: Aspergillus oryzae

<400> SEQUENCE: 24
tagaacatcg tccataatgg cggctccgtt tcgtca                            36

<210> SEQ ID NO 25
<211> LENGTH: 40
<212> TYPE: DNA
<213> ORGANISM: Aspergillus oryzae

<400> SEQUENCE: 25
gtgtcagtca cctctagtta ttattacgct ttgacgatct                        40

<210> SEQ ID NO 26
<211> LENGTH: 1143
<212> TYPE: DNA
<213> ORGANISM: Aspergillus oryzae

<400> SEQUENCE: 26
atgctgacac ctcccaagtt tgaggatgag aagcagctgg gccccgtggg tatccgggag    60
aggcttcgcc atttcacttg ggcctggtac acattaacga tgagtggagg agggctggcc   120
gtcctcatca tcagccagcc ctttgggttc cgcggattga gagagatcgg catcgctgtc   180
tatatcctca acctgatcct cttcgccctt gtctgctcta ccatggctat aaggttcatc   240

```
ctgcacggca accttctgga gtccctccgt catgaccgcg agggtctctt cttcccgacc      300
ttctggctct ccgtcgcaac catcatctgc ggcttgtctc gctacttcgg tgaagaatcg      360
aatgagtcct tccaactagc cctcgaagcc ctcttctgga tctactgcgt ctgcacctta      420
ctcgtcgcaa tcatccaata tcgttcgtc ttctcatccc acaagtacgg ccttcaaacc       480
atgatgcctt catggatcct tccagccttc cccatcatgc tcagcggcac catcgcctcc      540
gtcatcggtg aacaacaacc cgctcgcgca ccctcccca tcatcggcgc cggcgtcacc       600
ttccagggcc tcggcttctc catcagcttc atgatgtacg cccactacat cggccgactg      660
atggagtccg gcctccccca cagcgaccac agaccaggca tgttcatctg cgtcggaccc      720
cccgccttca cagccctcgc cctcgtcggc atgagcaaag gcctccccga agacttcaag      780
ctgctccacg acgcccacgc cctggaagat ggccgcatca tcgagctgct ggccatctcc      840
gccggcgtct cctctgggc cctgagtctc tggttcttct gcatcgccat tgtcgccgtc      900
atccgctcgc cccccgaggc cttccacctc aactggtggg ccatggtctt ccccaacacc      960
ggcttcaccc tggccaccat caccctgggc aaggctctca cagtaacgg cgtgaagggc      1020 gtcggctccg ccatgtctat ctgcatcgtg tgcatgtaca tcttcgtctt tgtcaacaat     1080
gtccgcgccg ttatccggaa ggatatcatg tacccgggta agatgagga tgtatctgat      1140 tag                                                                    1143

<210> SEQ ID NO 27
<211> LENGTH: 380
<212> TYPE: PRT
<213> ORGANISM: Aspergillus oryzae

<400> SEQUENCE: 27

Met Leu Thr Pro Pro Lys Phe Glu Asp Glu Lys Gln Leu Gly Pro Val
1               5                   10                  15

Gly Ile Arg Glu Arg Leu Arg His Phe Thr Trp Ala Trp Tyr Thr Leu
                20                  25                  30

Thr Met Ser Gly Gly Gly Leu Ala Val Leu Ile Ile Ser Gln Pro Phe
            35                  40                  45

Gly Phe Arg Gly Leu Arg Glu Ile Gly Ile Ala Val Tyr Ile Leu Asn
        50                  55                  60

Leu Ile Leu Phe Ala Leu Val Cys Ser Thr Met Ala Ile Arg Phe Ile
65                  70                  75                  80

Leu His Gly Asn Leu Leu Glu Ser Leu Arg His Asp Arg Glu Gly Leu
                85                  90                  95

Phe Phe Pro Thr Phe Trp Leu Ser Val Ala Thr Ile Ile Cys Gly Leu
            100                 105                 110

Ser Arg Tyr Phe Gly Glu Glu Ser Asn Glu Ser Phe Gln Leu Ala Leu
        115                 120                 125

Glu Ala Leu Phe Trp Ile Tyr Cys Val Cys Thr Leu Leu Val Ala Ile
    130                 135                 140

Ile Gln Tyr Ser Phe Val Phe Ser Ser His Lys Tyr Gly Leu Gln Thr
145                 150                 155                 160

Met Met Pro Ser Trp Ile Leu Pro Ala Phe Pro Ile Met Leu Ser Gly
                165                 170                 175

Thr Ile Ala Ser Val Ile Gly Glu Gln Gln Pro Ala Arg Ala Ala Leu
            180                 185                 190

Pro Ile Ile Gly Ala Gly Val Thr Phe Gln Gly Leu Gly Phe Ser Ile
        195                 200                 205

Ser Phe Met Met Tyr Ala His Tyr Ile Gly Arg Leu Met Glu Ser Gly
```

|     |     |     |     |     |     |     |     |     |     |     |     |     |     |     |
|-----|-----|-----|-----|-----|-----|-----|-----|-----|-----|-----|-----|-----|-----|-----|
|     |     |     | 210 |     |     |     |     | 215 |     |     |     |     | 220 |     |

Leu Pro His Ser Asp His Arg Pro Gly Met Phe Ile Cys Val Gly Pro
225                 230                 235                 240

Pro Ala Phe Thr Ala Leu Ala Leu Val Gly Met Ser Lys Gly Leu Pro
            245                 250                 255

Glu Asp Phe Lys Leu Leu His Asp Ala His Ala Leu Glu Asp Gly Arg
        260                 265                 270

Ile Ile Glu Leu Leu Ala Ile Ser Ala Gly Val Phe Leu Trp Ala Leu
    275                 280                 285

Ser Leu Trp Phe Phe Cys Ile Ala Ile Val Ala Ile Arg Ser Pro
290                 295                 300

Pro Glu Ala Phe His Leu Asn Trp Trp Ala Met Val Phe Pro Asn Thr
305                 310                 315                 320

Gly Phe Thr Leu Ala Thr Ile Thr Leu Gly Lys Ala Leu Asn Ser Asn
            325                 330                 335

Gly Val Lys Gly Val Gly Ser Ala Met Ser Ile Cys Ile Val Cys Met
        340                 345                 350

Tyr Ile Phe Val Phe Val Asn Asn Val Arg Ala Val Ile Arg Lys Asp
    355                 360                 365

Ile Met Tyr Pro Gly Lys Asp Glu Asp Val Ser Asp
370                 375                 380

<210> SEQ ID NO 28
<211> LENGTH: 1182
<212> TYPE: DNA
<213> ORGANISM: Aspergillus terreus

<400> SEQUENCE: 28

| | |
|---|---|
| atgtttgaga acactgcccc tccagggagc tcccgctccg actctggcat cctggaccat | 60 |
| gaattcgaga agcagccggg ttccgtgggc atgcgtgaac gcatccgcca ttttacctgg | 120 |
| gcctggtata ctctcacaat gagtgctggt ggcttggccc cctccttgg gagccagcca | 180 |
| aacaccttca ccggcctgag ggagattgga ctcgccgtgt acctgctcaa cctgctcttc | 240 |
| tttgccctgg tctgctcgac catggccggc cggttcatcc tgcacggagg ctggtcgac | 300 |
| tctctccggc acgaacgcga gggcatcttc ttcccaacct tctggctctc gatcgccacc | 360 |
| atcatcacag gctgtaccg ctacttcggc gaagacgccg acgcccctt cgtgctcgcc | 420 |
| ctcgaagccc tcttctggat ctactgcgct tgcaccctcc tcgtcgccgt catccaatac | 480 |
| tcctggctct tctccggccc caaataccgc tccaaaccg ccatgccggg ctggatcctc | 540 |
| cccgccttcc ctgtcatgct ctctggcacc atcgcctccg tcatcgccga gcagcagccg | 600 |
| gcccgcgccg ccatcccat catcgtcgcc ggcaccacct tccagggcct gggcttctcc | 660 |
| atcagcatga tcatgtacgc ccactacgtc ggccgcctca tggagtccgg cctgccgtgc | 720 |
| cgcgagcacc gcccgggcat gttcatcgcc gtcggcccgc cggctttcac ggcgctggcc | 780 |
| ctcgtcggca tgaccaaggg gctcccgcac gacttccagc tcatcggcga tgacttcgcc | 840 |
| ttcgaggatg cccgcatcct gcagctgctg gcgatcgccg tcggcgtgtt tctctgggcg | 900 |
| ctgagtctgt ggttcttttg cattgcggcc attgcgtcg tgcgctcccc gccaacggcc | 960 |
| ttccacctga gctggtgggc catggtcttc cccaacacgg gcttcaccct cgccacgatc | 1020 |
| aacctgggta cggccctcaa gagcgagggt atccagggtg tggggacggc catgtcgatt | 1080 |
| ggaattgtgt ctattttctt gtttgtgttt atcagccatg tgcgggctgt catcaggaaa | 1140 |
| gacattatgt atcctgggaa agacgaggat gtggtggagt aa | 1182 |

<210> SEQ ID NO 29
<211> LENGTH: 393
<212> TYPE: PRT
<213> ORGANISM: Aspergillus terreus

<400> SEQUENCE: 29

Met Phe Glu Asn Thr Ala Pro Pro Gly Ser Arg Ser Asp Ser Gly
1               5                   10                  15

Ile Leu Asp His Glu Phe Glu Lys Gln Pro Gly Ser Val Gly Met Arg
            20                  25                  30

Glu Arg Ile Arg His Phe Thr Trp Ala Trp Tyr Thr Leu Thr Met Ser
        35                  40                  45

Ala Gly Gly Leu Ala Leu Leu Gly Ser Gln Pro Asn Thr Phe Thr
    50                  55                  60

Gly Leu Arg Glu Ile Gly Leu Ala Val Tyr Leu Asn Leu Leu Phe
65                  70                  75                  80

Phe Ala Leu Val Cys Ser Thr Met Ala Gly Arg Phe Ile Leu His Gly
                85                  90                  95

Gly Leu Val Asp Ser Leu Arg His Glu Arg Glu Gly Ile Phe Phe Pro
            100                 105                 110

Thr Phe Trp Leu Ser Ile Ala Thr Ile Ile Thr Gly Leu Tyr Arg Tyr
        115                 120                 125

Phe Gly Glu Asp Ala Gly Arg Pro Phe Val Leu Ala Leu Glu Ala Leu
    130                 135                 140

Phe Trp Ile Tyr Cys Ala Cys Thr Leu Leu Val Ala Val Ile Gln Tyr
145                 150                 155                 160

Ser Trp Leu Phe Ser Gly Pro Lys Tyr Arg Leu Gln Thr Ala Met Pro
                165                 170                 175

Gly Trp Ile Leu Pro Ala Phe Pro Val Met Leu Ser Gly Thr Ile Ala
            180                 185                 190

Ser Val Ile Ala Glu Gln Gln Pro Ala Arg Ala Ala Ile Pro Ile Ile
        195                 200                 205

Val Ala Gly Thr Thr Phe Gln Gly Leu Gly Phe Ser Ile Ser Met Ile
    210                 215                 220

Met Tyr Ala His Tyr Val Gly Arg Leu Met Glu Ser Gly Leu Pro Cys
225                 230                 235                 240

Arg Glu His Arg Pro Gly Met Phe Ile Ala Val Gly Pro Pro Ala Phe
                245                 250                 255

Thr Ala Leu Ala Leu Val Gly Met Thr Lys Gly Leu Pro His Asp Phe
            260                 265                 270

Gln Leu Ile Gly Asp Asp Phe Ala Phe Glu Asp Ala Arg Ile Leu Gln
        275                 280                 285

Leu Leu Ala Ile Ala Val Gly Val Phe Leu Trp Ala Leu Ser Leu Trp
    290                 295                 300

Phe Phe Cys Ile Ala Ala Ile Ala Val Val Arg Ser Pro Pro Thr Ala
305                 310                 315                 320

Phe His Leu Ser Trp Trp Ala Met Val Phe Pro Asn Thr Gly Phe Thr
                325                 330                 335

Leu Ala Thr Ile Asn Leu Gly Thr Ala Leu Lys Ser Glu Gly Ile Gln
            340                 345                 350

Gly Val Gly Thr Ala Met Ser Ile Gly Ile Val Ser Ile Phe Leu Phe
        355                 360                 365

Val Phe Ile Ser His Val Arg Ala Val Ile Arg Lys Asp Ile Met Tyr
    370                 375                 380

Pro Gly Lys Asp Glu Asp Val Val Glu
385                 390

<210> SEQ ID NO 30
<211> LENGTH: 1317
<212> TYPE: DNA
<213> ORGANISM: Schizosaccharomyces pombe

<400> SEQUENCE: 30

| | | |
|---|---|---|
| atgggagaat tgaaggaaat tctcaagcag cgctaccatg aattgctcga ctggaacgtc | 60 |
| aaagcacccc acgtccctct ctcgcagagg ttgaagcatt tcacatggtc gtggttcgcg | 120 |
| tgtacgatgg caaccggtgg cgtcggactc atcatcggat ccttcccttt ccgattctac | 180 |
| ggactcaaca cgatcggcaa gattgtgtac atcctccaga ttttcctctt ctccttgttc | 240 |
| ggctcgtgta tgctcttcag gttcatcaag tatccgtcca caatcaagga ctcctggaac | 300 |
| catcatctcg agaaactctt cattgcgact tgtctcctct cgatttcgac attcatcgat | 360 |
| atgttggcga tctacgccta ccccgacaca ggcgagtgga tggtgtgggt catccgaatc | 420 |
| ctctactaca tctacgtcgc ggtctccttc atttactgtg tgatggcgtt cttcacgatc | 480 |
| ttcaacaacc acgtctatac cattgaaacc gcctcgcctg catggatcct ccctatcttc | 540 |
| cctccgatga tctgtggtgt cattgccggt gcggtgaact ccacccagcc tgcgcaccag | 600 |
| ctcaaaaaca tggtgatttt cggaatcctc ttccaggdat tgggtttctg ggtctacttg | 660 |
| ctcttgttcg cagtcaacgt gctccggttc ttcacggtcg gcttggcaaa gccccaggac | 720 |
| cgacctggca tgttcatgtt cgtgggacct cctgcgttct ccggcttggc actcatcaac | 780 |
| atcgcgaggg gtgccatggg ctcgaggccg tacatcttcg tgggagcaaa ctcctcggaa | 840 |
| tacttggggtt tcgtgtcgac gttcatggcg attttcatct ggggcttggc agcatggtgt | 900 |
| tattgtctcg ccatggtgtc cttcctcgca ggcttcttca cacgcgcacc tttgaagttc | 960 |
| gcgtgtggtt ggttcgcatt catcttcccc aacgtgggct tcgtgaactg tacgattgag | 1020 |
| atcggcaaga tgatcgactc caaagccttc cagatgttcg ccacattat cggtgtcatc | 1080 |
| ctctgtatcc agtggatttt gctcatgtat ttgatggtgc gtgcgttctt ggtcaacgac | 1140 |
| ttgtgttatc ccggtaaaga cgaggacgcc catccgcctc ccaaacccaa cacaggcgtc | 1200 |
| ctcaaccccca ccttccctcc cgaaaaagca cctgcctccc tcgaaaaagt cgatacacat | 1260 |
| gtcacttcca ctggcggaga gtcggatcct ccgtcctccg aacacgagtc ggtctaa | 1317 |

<210> SEQ ID NO 31
<211> LENGTH: 1317
<212> TYPE: DNA
<213> ORGANISM: Schizosaccharomyces pombe

<400> SEQUENCE: 31

| | | |
|---|---|---|
| atgggtgaac tcaaggaaat cttgaaacag aggtatcatg agttgcttga ctggaatgtc | 60 |
| aaagcccctc atgtccctct cagtcaacga ctgaagcatt ttacatggtc ttggtttgca | 120 |
| tgtactatgg caactggtgg tgttggtttg attattggtt cttttcccctt tcgattttat | 180 |
| ggtcttaata caattggcaa aattgtttat attcttcaaa tcttttttgtt ttctctcttt | 240 |
| ggatcatgca tgcttttcg ctttattaaa tatccttcaa ctatcaagga ttcctggaac | 300 |
| catcatttgg aaaagcttt cattgctact tgtcttcttt caatatccac gttcatcgac | 360 |
| atgcttgcca tatacgccta tcctgatacc ggcgagtgga tggtgtgggt cattcgaatc | 420 |
| ctttattaca tttacgttgc agtatccttt atatactgcg taatggcttt ttttacaatt | 480 |
| ttcaacaacc atgtatatac cattgaaacc gcatctcctg cttggattct tcctattttc | 540 |

```
cctcctatga tttgtggtgt cattgctggc gccgtcaatt ctacacaacc cgctcatcaa     600
ttaaaaaata tggttatctt tggtatcctc tttcaaggac ttggttttg ggtttatctt     660 ttactgtttg ccgtcaatgt cttacggttt tttactgtag gcctggcaaa accccaagat    720
cgacctggta tgtttatgtt tgtcggtcca ccagctttct caggtttggc cttaattaat   780
attgcgcgtg gtgctatggg cagtcgccct tatattttg ttggcgccaa ctcatccgag    840
tatcttggtt ttgtttctac ctttatggct atttttattt ggggtcttgc tgcttggtgt   900
tactgtctcg ccatggttag ctttttagcg ggcttttca ctcgagcccc tctcaagttt    960
gcttgtggat ggtttgcatt cattttcccc aacgtgggtt ttgttaattg taccattgag   1020
ataggtaaaa tgatagattc caaagctttc caaatgtttg gacatatcat tggggtcatt   1080
ctttgtattc agtggatcct cctaatgtat ttaatggtcc gtgcgtttct cgtcaatgat   1140
ctttgctatc ctggcaaaga cgaagatgcc catcctccac caaaaccaaa tacaggtgtc   1200
cttaacccta ccttcccacc tgaaaaagca cctgcatctt tggaaaaagt cgatacacat   1260
gtcacatcta ctggtggtga atcggatcct cctagtagtg aacatgaaag cgtttaa     1317
```

<210> SEQ ID NO 32
<211> LENGTH: 438
<212> TYPE: PRT
<213> ORGANISM: Schizosaccharomyces pombe

<400> SEQUENCE: 32

```
Met Gly Glu Leu Lys Glu Ile Leu Lys Gln Arg Tyr His Glu Leu Leu
1               5                   10                  15

Asp Trp Asn Val Lys Ala Pro His Val Pro Leu Ser Gln Arg Leu Lys
            20                  25                  30

His Phe Thr Trp Ser Trp Phe Ala Cys Thr Met Ala Thr Gly Gly Val
        35                  40                  45

Gly Leu Ile Ile Gly Ser Phe Pro Phe Arg Phe Tyr Gly Leu Asn Thr
    50                  55                  60

Ile Gly Lys Ile Val Tyr Ile Leu Gln Ile Phe Leu Phe Ser Leu Phe
65                  70                  75                  80

Gly Ser Cys Met Leu Phe Arg Phe Ile Lys Tyr Pro Ser Thr Ile Lys
                85                  90                  95

Asp Ser Trp Asn His His Leu Glu Lys Leu Phe Ile Ala Thr Cys Leu
            100                 105                 110

Leu Ser Ile Ser Thr Phe Ile Asp Met Leu Ala Ile Tyr Ala Tyr Pro
        115                 120                 125

Asp Thr Gly Glu Trp Met Val Trp Val Arg Ile Leu Tyr Tyr Ile
    130                 135                 140

Tyr Val Ala Val Ser Phe Ile Tyr Cys Val Met Ala Phe Phe Thr Ile
145                 150                 155                 160

Phe Asn Asn His Val Tyr Thr Ile Glu Thr Ala Ser Pro Ala Trp Ile
                165                 170                 175

Leu Pro Ile Phe Pro Pro Met Ile Cys Gly Val Ile Ala Gly Ala Val
            180                 185                 190

Asn Ser Thr Gln Pro Ala His Gln Leu Lys Asn Met Val Ile Phe Gly
        195                 200                 205

Ile Leu Phe Gln Gly Leu Gly Phe Trp Val Tyr Leu Leu Phe Ala
    210                 215                 220

Val Asn Val Leu Arg Phe Phe Thr Val Gly Leu Ala Lys Pro Gln Asp
225                 230                 235                 240
```

```
Arg Pro Gly Met Phe Met Phe Val Gly Pro Pro Ala Phe Ser Gly Leu
                245                 250                 255

Ala Leu Ile Asn Ile Ala Arg Gly Ala Met Gly Ser Arg Pro Tyr Ile
            260                 265                 270

Phe Val Gly Ala Asn Ser Ser Glu Tyr Leu Gly Phe Val Ser Thr Phe
        275                 280                 285

Met Ala Ile Phe Ile Trp Gly Leu Ala Ala Trp Cys Tyr Cys Leu Ala
    290                 295                 300

Met Val Ser Phe Leu Ala Gly Phe Phe Thr Arg Ala Pro Leu Lys Phe
305                 310                 315                 320

Ala Cys Gly Trp Phe Ala Phe Ile Phe Pro Asn Val Gly Phe Val Asn
                325                 330                 335

Cys Thr Ile Glu Ile Gly Lys Met Ile Asp Ser Lys Ala Phe Gln Met
            340                 345                 350

Phe Gly His Ile Ile Gly Val Ile Leu Cys Ile Gln Trp Ile Leu Leu
        355                 360                 365

Met Tyr Leu Met Val Arg Ala Phe Leu Val Asn Asp Leu Cys Tyr Pro
    370                 375                 380

Gly Lys Asp Glu Asp Ala His Pro Pro Lys Pro Asn Thr Gly Val
385                 390                 395                 400

Leu Asn Pro Thr Phe Pro Pro Glu Lys Ala Pro Ala Ser Leu Glu Lys
                405                 410                 415

Val Asp Thr His Val Thr Ser Thr Gly Gly Glu Ser Asp Pro Pro Ser
            420                 425                 430

Ser Glu His Glu Ser Val
        435

<210> SEQ ID NO 33
<211> LENGTH: 1194
<212> TYPE: DNA
<213> ORGANISM: Aspergillus aculeatus

<400> SEQUENCE: 33
atgctcgggc aacatccgcc tcccgacacc tcctgctcgg accttacaac ataccagcat      60
gagctcaaag cctccaaata ctctagttcc accaatgtgt ctctacggga ccgtctgcgt     120
cattttacct gggcgtggta tactctgact atgagcaccg gcggtctagc cctcctgctg     180
gccagccagc cctactcctt ctccggactg caacagatcg gcttgcagt ctacatcatc      240 aacctggcct tctttgcgtt gctgtgtagc ctcatggccg cacgcttcat tctccacggc     300
aacttcctcg actccctccg acacgaccgc gagggtcttt tctttcctac tttctggctt     360
tctattgcaa ctatcatcac cggcctgtac cgctacttcg cgacaccac acagcctgca      420 ttcatttacg ctcttgaggt gctcttctgg ctctactgtg ccttcactct gatgaccgct     480
attatccaat actcctttgt ctttaccgcc caccactacc ctctacaaac gatgatgccc     540
tcatggatcc tccccgcatt ccctatcatg ctcagcggca cgatcgcctc cgtcattgcc     600
gaacagcagc cgcgcgctc tgctattccc atgatcgtcg ccggcaccac cttccaaggc      660
cttggcttct ccatcagttt cctcatgtac gcgcactata tcgggcggct catggagacg     720
ggccttccgt cccgggaaca ccgacccggg atgttcatct gcgttggccc cccggctttc     780
acggcccttg cctaatcgg catgaccaac ggccttcctg aggattttca agtccttcaa      840
gacccgcacc cctttcaaga cgcgcacatc ctccgactcc ttgccatcgc cacgggcgcc     900
ttcctctggg ccctcagtct ctggttcttt agcattgcca tcatcgccac catccgcctc     960
ccacctacag ccttccacct caactggtgg gccatggttt ttccaaacac gggttttact    1020
```

```
ctcgcgacca tcacgctggg caaagccttc gatagccctg gagtcaaggg cgtcggatct    1080
gccatgtcca tttgcatcgt ggggatgtgg ctgttcgtgt ttgcgagcaa tatccgtgcc    1140
gttgtcaaac gggatattgt tttccctggg aaggacgagg atgtatcgga gtaa          1194
```

<210> SEQ ID NO 34
<211> LENGTH: 397
<212> TYPE: PRT
<213> ORGANISM: Aspergillus aculeatus

<400> SEQUENCE: 34

```
Met Leu Gly Gln His Pro Pro Asp Thr Ser Cys Ser Asp Leu Thr
1               5                   10                  15

Thr Tyr Gln His Glu Leu Lys Ala Ser Lys Tyr Ser Ser Ser Thr Asn
            20                  25                  30

Val Ser Leu Arg Asp Arg Leu Arg His Phe Thr Trp Ala Trp Tyr Thr
        35                  40                  45

Leu Thr Met Ser Thr Gly Gly Leu Ala Leu Leu Ala Ser Gln Pro
    50                  55                  60

Tyr Ser Phe Ser Gly Leu Gln Gln Ile Gly Leu Ala Val Tyr Ile Ile
65                  70                  75                  80

Asn Leu Ala Phe Phe Ala Leu Leu Cys Ser Leu Met Ala Ala Arg Phe
                85                  90                  95

Ile Leu His Gly Asn Phe Leu Asp Ser Leu Arg His Asp Arg Glu Gly
            100                 105                 110

Leu Phe Phe Pro Thr Phe Trp Leu Ser Ile Ala Thr Ile Ile Thr Gly
        115                 120                 125

Leu Tyr Arg Tyr Phe Gly Asp Thr Thr Gln Pro Ala Phe Ile Tyr Ala
    130                 135                 140

Leu Glu Val Leu Phe Trp Leu Tyr Cys Ala Phe Thr Leu Met Thr Ala
145                 150                 155                 160

Ile Ile Gln Tyr Ser Phe Val Phe Thr Ala His His Tyr Pro Leu Gln
                165                 170                 175

Thr Met Pro Ser Trp Ile Leu Pro Ala Phe Pro Ile Met Leu Ser
            180                 185                 190

Gly Thr Ile Ala Ser Val Ile Ala Glu Gln Gln Pro Ala Arg Ser Ala
        195                 200                 205

Ile Pro Met Ile Val Ala Gly Thr Thr Phe Gln Gly Leu Gly Phe Ser
    210                 215                 220

Ile Ser Phe Leu Met Tyr Ala His Tyr Ile Gly Arg Leu Met Glu Thr
225                 230                 235                 240

Gly Leu Pro Ser Arg Glu His Arg Pro Gly Met Phe Ile Cys Val Gly
                245                 250                 255

Pro Pro Ala Phe Thr Ala Leu Ala Leu Ile Gly Met Thr Asn Gly Leu
            260                 265                 270

Pro Glu Asp Phe Gln Val Leu Gln Asp Pro His Pro Phe Gln Asp Ala
        275                 280                 285

His Ile Leu Arg Leu Leu Ala Ile Ala Thr Gly Ala Phe Leu Trp Ala
    290                 295                 300

Leu Ser Leu Trp Phe Phe Ser Ile Ala Ile Ala Thr Ile Arg Leu
305                 310                 315                 320

Pro Pro Thr Ala Phe His Leu Asn Trp Trp Ala Met Val Phe Pro Asn
                325                 330                 335

Thr Gly Phe Thr Leu Ala Thr Ile Thr Leu Gly Lys Ala Phe Asp Ser
            340                 345                 350
```

-continued

```
Pro Gly Val Lys Gly Val Gly Ser Ala Met Ser Ile Cys Ile Val Gly
        355                 360                 365

Met Trp Leu Phe Val Phe Ala Ser Asn Ile Arg Ala Val Val Lys Arg
    370                 375                 380

Asp Ile Val Phe Pro Gly Lys Asp Glu Asp Val Ser Glu
385                 390                 395

<210> SEQ ID NO 35
<211> LENGTH: 1194
<212> TYPE: DNA
<213> ORGANISM: Aspergillus aculeatus

<400> SEQUENCE: 35
atgctcgggc aacactcgcc tcccggcacc tcctgctcgg accttacaac ataccaacat      60
gagcttaaag cctccaaata ctctagttcc accaatgtgt ctctacggga ccgtctgcgt     120
cattttacct gggcctggta tactctgact atgagcaccg gcggcctagc gcttctgctg     180
gccagccagc cctacacctt ctccggactg caacagatcg ggcttgcagt ctatatcatc     240
aacctggtct tctttgcttt gctgtgcagc ctcatggcca cgcgcttcat tctccacggc     300
aacttcctcg actccctccg acacgaccgc gagggtcttt tctttcccac tttctggctt     360
tccattgcaa ctatcatcac cggactctac cgctacttcg gcgacaccac acagcctgca     420
ttcatttacg cccttgaggt gcttttctgg ctctactgtg ccttcacact gatgaccgct     480
atcatccaat actcttttgt ctttactgcc caccactacc ctctacaaac gatgatgccc     540
tcgtggatcc tccccgcatt ccccatcatg ctaagcggca cgatcgcctc tgtcattgcc     600
gaacagcagc ccgcgcgctc tgctattccc atgatcgtcg ccggcaccac cttccaaggc     660
cttggcttct ccatcagttt cctcatgtac gcgcactata tcggacgcct catggagacg     720
ggccttccgt cccgggaaca ccgacccggg atgttcatct gcgttggccc ccctgctttc     780
acggcccttg cctaatcgg catgaccaac ggccttcctg aggattttca agtccttcaa     840
gacccgcacc cctttcaaga cgcgcatatc ctccgactcc ttgccatcgc acgggcgcc     900 ttcctctggg ccctcagtct ctggttcttc agcattgcca ttatcgccac catccgcctc     960
ccacctacgg ccttccacct caactggtgg gccatggttt ttccaaacac gggtttttact    1020 ctcgcgacca tcacgctggg caaagccttc gatagccctg gagtcaaggg cgtcggatct    1080
gccatgtcca tttgcatcgt ggggatgtgg ctgttcgtgt ttgcgagcaa tatccgcgcc    1140
gttgtcaaac gggatattgt gtttcctggc aaggacgagg atgtatcgga gtaa           1194

<210> SEQ ID NO 36
<211> LENGTH: 397
<212> TYPE: PRT
<213> ORGANISM: Aspergillus aculeatus

<400> SEQUENCE: 36

Met Leu Gly Gln His Ser Pro Pro Gly Thr Ser Cys Ser Asp Leu Thr
1               5                   10                  15

Thr Tyr Gln His Glu Leu Lys Ala Ser Lys Tyr Ser Ser Thr Asn
            20                  25                  30

Val Ser Leu Arg Asp Arg Leu Arg His Phe Thr Trp Ala Trp Tyr Thr
        35                  40                  45

Leu Thr Met Ser Thr Gly Gly Leu Ala Leu Leu Ala Ser Gln Pro
    50                  55                  60

Tyr Thr Phe Ser Gly Leu Gln Gln Ile Gly Leu Ala Val Tyr Ile Ile
65                  70                  75                  80
```

```
Asn Leu Val Phe Phe Ala Leu Leu Cys Ser Leu Met Ala Thr Arg Phe
                 85                  90                  95

Ile Leu His Gly Asn Phe Leu Asp Ser Leu Arg His Asp Arg Glu Gly
            100                 105                 110

Leu Phe Phe Pro Thr Phe Trp Leu Ser Ile Ala Thr Ile Ile Thr Gly
        115                 120                 125

Leu Tyr Arg Tyr Phe Gly Asp Thr Thr Gln Pro Ala Phe Ile Tyr Ala
    130                 135                 140

Leu Glu Val Leu Phe Trp Leu Tyr Cys Ala Phe Thr Leu Met Thr Ala
145                 150                 155                 160

Ile Ile Gln Tyr Ser Phe Val Phe Thr Ala His His Tyr Pro Leu Gln
                165                 170                 175

Thr Met Met Pro Ser Trp Ile Leu Pro Ala Phe Pro Ile Met Leu Ser
            180                 185                 190

Gly Thr Ile Ala Ser Val Ile Ala Glu Gln Gln Pro Ala Arg Ser Ala
        195                 200                 205

Ile Pro Met Ile Val Ala Gly Thr Thr Phe Gln Gly Leu Gly Phe Ser
    210                 215                 220

Ile Ser Phe Leu Met Tyr Ala His Tyr Ile Gly Arg Leu Met Glu Thr
225                 230                 235                 240

Gly Leu Pro Ser Arg Glu His Arg Pro Gly Met Phe Ile Cys Val Gly
                245                 250                 255

Pro Pro Ala Phe Thr Ala Leu Ala Leu Ile Gly Met Thr Asn Gly Leu
            260                 265                 270

Pro Glu Asp Phe Gln Val Leu Gln Asp Pro His Pro Phe Gln Asp Ala
        275                 280                 285

His Ile Leu Arg Leu Leu Ala Ile Ala Thr Gly Ala Phe Leu Trp Ala
    290                 295                 300

Leu Ser Leu Trp Phe Phe Ser Ile Ala Ile Ala Thr Ile Arg Leu
305                 310                 315                 320

Pro Pro Thr Ala Phe His Leu Asn Trp Trp Ala Met Val Phe Pro Asn
                325                 330                 335

Thr Gly Phe Thr Leu Ala Thr Ile Thr Leu Gly Lys Ala Phe Asp Ser
            340                 345                 350

Pro Gly Val Lys Gly Val Gly Ser Ala Met Ser Ile Cys Ile Val Gly
        355                 360                 365

Met Trp Leu Phe Val Phe Ala Ser Asn Ile Arg Ala Val Val Lys Arg
    370                 375                 380

Asp Ile Val Phe Pro Gly Lys Asp Glu Asp Val Ser Glu
385                 390                 395

<210> SEQ ID NO 37
<211> LENGTH: 1353
<212> TYPE: DNA
<213> ORGANISM: Schizosaccharomyces japonicus

<400> SEQUENCE: 37
atgtcgtcgg agacaccgac atactcctcc tgggcatccc agaggtacaa cgaattgatt      60
gcatggaacg tcaagggtcc gaggttgccc atcgcacaga ggctcaagca cttcacgtgg     120
tcgtggttca cgtgtactat gcaacaggc ggtgtcggaa tgatcctcgc gtcgctcccc      180
tataggttca cgggcttgaa caccatcgga aaggtcgtct tcattttcca ggtggtcttg     240
ttggccatct tctgttcggc catggccttc aggttcattc gctacccgga gactttcaag     300
aagtcgatct atcaccactt ggagaaattg ttcatcggta cattcttgct ctcgatgtcg     360
```

```
accttcatcg atatgctcgc agcctacggc tatccttcca ccggtgaatg gatggtgtac    420
ttgatccgaa tcttctactg gatgtacttc gccgtctcct tcgtctacgc gatcttcgca    480
ttcgcaacta ctttccatat gcatccttat accctgaaaa cggcatcgcc tgcctggatc    540
ctcccgattt tccctgcgat gatctccgga gcagtggcag gaaccgtggc attcactcag    600
cctccccatc agctcaaaaa cctcgtggtg tgtggcatta tgttccaggg tttgggcttc    660
tgggtctaca tcatgttgtt cgcggtcaac atgctcaaat tgttcacaaa gggcatgatg    720
ggagcctcgg aacgaccggg tttgttcatg ttcgtcggac ctccggcata cacaggcctc    780
gccctcatcg gtatgggcaa gaccgccatg gattccaaaa tctccatgtt ctccgccact    840
cccgtctcct ccgaacacct cgcattcatg tgtaccttca tggcactctt catgtggggt    900
ctcgcagcgt ggtgttattg tgtggcgatg gtctgtttcg cagcaggttt catgtccagg    960
gcacctatcc agttcaagtt gggatggttc gcgttcatct tccctgtcgt gggcttcgtg   1020
aacgtcacca tgaagatcgg cgagatgatt gactcggcag ccttcaaaat cttcggccac   1080
gtcatcggag ccatgttggc catccagtgg atgttcgtga tgttcttcat ggtgcgagcg   1140
gtcttgttgc aggaaatcat gtatcctgga cgggacgagg acgtcaaaac accgcctgga   1200
gccacacctc ctccgaccct cgtgacctcc cctctctcct tcgcatccct ccaggatgtc   1260
aaggatggac accccatcca ggtgacggtc tcccgcacta gggatcggtc gaaacagcac   1320
atgtcccagg gctcggacga ggaaaagatt taa                                1353
```

<210> SEQ ID NO 38
<211> LENGTH: 1353
<212> TYPE: DNA
<213> ORGANISM: Schizosaccharomyces japonicus

<400> SEQUENCE: 38

```
atgtcttcgg aaacgccgac ttacagctct tgggcgagcc aacggtacaa cgaattgatc    60
gcttggaacg tcaagggtcc tcgcttaccc attgcccagc gtctaaaaca cttcacttgg   120
tcctggttta cctgtaccat ggccaccggt ggtgtcggta tgattctggc atcgctgccc   180
taccgattca caggcttaaa cacgattggt aaagtcgtgt catttttcca ggtcgttttg   240
ctggcgattt tctgttcggc gatggccttt cggttcattc gttaccccga accttcaaaa   300
aagtctattt accatcattt ggagaagctc ttcattggta ccttcctgct ttccatgtcg   360
acgttcatcg atatgctcgc cgcctacgga taccccagca ctggcgagtg gatggtgtac   420
ctaattcgca tttttttactg gatgtacttt gccgtctcgt tcgtatacgc catcttcgca   480
tttgctacca cctttcacat gcatccctac accctggaga cggcttcccc agcatggatt   540
ctgcctattt tcccagctat gattagcggc gctgtcgccg gtactgtggc cttcacacaa   600
ccgccgcacc aattgaagaa tttggtcgtg tgcggtatca tgttccaggg cttgggtttc   660
tgggtgtaca tcatgctgtt cgccgtgaac atgctcaagc tgtttacgaa gggtatgatg   720
ggtgcctctg aacgccctgg tctttttatg ttcgttggtc ctccggccta taccggcttg   780
gctttaatcg gtatgggtaa aactgctatg gactccaaga tctccatgtt ttctgcaacc   840
cccgtttctt ctgaacacct tgcctttatg tgtacctttta tggccttgtt tatgtggggt   900
cttgctgctt ggtgctattg tgtggccatg gtctgctttg ctgctggttt catgtctcgt   960
gctcctattc aattcaaact cggctggttc gcatttattt tcccagtcgt tggttttgtc  1020
aacgttacta tgaagattgg tgagatgatt gattcggccg cgttcaagat ctttggtcat  1080
gtcattggtg caatgcttgc cattcagtgg atgtttgtga tgttcttcat ggtccgcgcc  1140
```

```
gtcttactgc aagagatcat gtacccgggc cgcgacgaag atgtcaagac acctcccggt    1200
gccactcctc ctcccacttt ggtgacgagt cccttgtcct ttgcttcgct gcaagacgta    1260
aaagatggcc atcccattca ggtcaccgtg tcccgcactc gagacagaag caaacagcac    1320
atgtcgcagg gctctgatga agaaaaaatc tag                                 1353
```

<210> SEQ ID NO 39
<211> LENGTH: 450
<212> TYPE: PRT
<213> ORGANISM: Schizosaccharomyces japonicus

<400> SEQUENCE: 39

```
Met Ser Ser Glu Thr Pro Thr Tyr Ser Ser Trp Ala Ser Gln Arg Tyr
1               5                   10                  15

Asn Glu Leu Ile Ala Trp Asn Val Lys Gly Pro Arg Leu Pro Ile Ala
            20                  25                  30

Gln Arg Leu Lys His Phe Thr Trp Ser Trp Phe Thr Cys Thr Met Ala
        35                  40                  45

Thr Gly Gly Val Gly Met Ile Leu Ala Ser Leu Pro Tyr Arg Phe Thr
    50                  55                  60

Gly Leu Asn Thr Ile Gly Lys Val Val Phe Ile Phe Gln Val Val Leu
65                  70                  75                  80

Leu Ala Ile Phe Cys Ser Ala Met Ala Phe Arg Phe Ile Arg Tyr Pro
                85                  90                  95

Glu Thr Phe Lys Lys Ser Ile Tyr His His Leu Glu Lys Leu Phe Ile
            100                 105                 110

Gly Thr Phe Leu Leu Ser Met Ser Thr Phe Ile Asp Met Leu Ala Ala
        115                 120                 125

Tyr Gly Tyr Pro Ser Thr Gly Glu Trp Met Val Tyr Leu Ile Arg Ile
    130                 135                 140

Phe Tyr Trp Met Tyr Phe Ala Val Ser Phe Val Tyr Ala Ile Phe Ala
145                 150                 155                 160

Phe Ala Thr Thr Phe His Met His Pro Tyr Thr Leu Glu Thr Ala Ser
                165                 170                 175

Pro Ala Trp Ile Leu Pro Ile Phe Pro Ala Met Ile Ser Gly Ala Val
            180                 185                 190

Ala Gly Thr Val Ala Phe Thr Gln Pro Pro His Gln Leu Lys Asn Leu
        195                 200                 205

Val Val Cys Gly Ile Met Phe Gln Gly Leu Gly Phe Trp Val Tyr Ile
    210                 215                 220

Met Leu Phe Ala Val Asn Met Leu Lys Leu Phe Thr Lys Gly Met Met
225                 230                 235                 240

Gly Ala Ser Glu Arg Pro Gly Leu Phe Met Phe Val Gly Pro Pro Ala
                245                 250                 255

Tyr Thr Gly Leu Ala Leu Ile Gly Met Gly Lys Thr Ala Met Asp Ser
            260                 265                 270

Lys Ile Ser Met Phe Ser Ala Thr Pro Val Ser Ser Glu His Leu Ala
        275                 280                 285

Phe Met Cys Thr Phe Met Ala Leu Phe Met Trp Gly Leu Ala Ala Trp
    290                 295                 300

Cys Tyr Cys Val Ala Met Val Cys Phe Ala Ala Gly Phe Met Ser Arg
305                 310                 315                 320

Ala Pro Ile Gln Phe Lys Leu Gly Trp Phe Ala Phe Ile Phe Pro Val
                325                 330                 335
```

-continued

```
Val Gly Phe Val Asn Val Thr Met Lys Ile Gly Glu Met Ile Asp Ser
            340                 345                 350

Ala Ala Phe Lys Ile Phe Gly His Val Ile Gly Ala Met Leu Ala Ile
            355                 360                 365

Gln Trp Met Phe Val Met Phe Phe Met Val Arg Ala Val Leu Leu Gln
370                 375                 380

Glu Ile Met Tyr Pro Gly Arg Asp Glu Asp Val Lys Thr Pro Pro Gly
385                 390                 395                 400

Ala Thr Pro Pro Pro Thr Leu Val Thr Ser Pro Leu Ser Phe Ala Ser
                405                 410                 415

Leu Gln Asp Val Lys Asp Gly His Pro Ile Gln Val Thr Val Ser Arg
            420                 425                 430

Thr Arg Asp Arg Ser Lys Gln His Met Ser Gln Gly Ser Asp Glu Glu
            435                 440                 445

Lys Ile
    450
```

```
<210> SEQ ID NO 40
<211> LENGTH: 1179
<212> TYPE: DNA
<213> ORGANISM: Aspergillus clavatus

<400> SEQUENCE: 40
```

| | |
|---|---|
| atgttcgaaa atcgtatacc gccgacctcg tctcagtcag actctggctt cctcgagaac | 60 |
| cagctggaaa acaacatcg actcagcctc cgtgagaggt taaggcactt tacctgggcc | 120 |
| tggtacacat tgaccatgag cacaggtggg ttggctctcc tgatagcgag ccagccatac | 180 |
| accttcaagg ggttgaagac cattggactg gtggtctaca tcgtgaactt gatcttgttt | 240 |
| ggtcttgtct gttcccttat ggccactagg ttcatcctcc acggtggctt cctcgactcc | 300 |
| cttcgccatg agcgcgaggg tcttttcttt cctaccttct ggctatccgt agcaaccatc | 360 |
| atcaccggct gcatcgcta cttcggctcc gatgctcgag aatcgtacct gattgcactc | 420 |
| gaagtactct tctgggtcta ctgtgcctgt acactggcca cagcagtgat ccagtactcc | 480 |
| ttcatcttct ctgcgcacag atacggcctc cagaccatga tgccctcctg gattctccca | 540 |
| gccttcccca tcatgctcag tggcacgatt gcctccgtca tcggcgaagc tcaacccgca | 600 |
| cggtcatcga tccccgtcat catggccgga gtcaccttcc agggcctggg gttctcgatc | 660 |
| agcttcatga tgtacgccca ctatatcggc cggctgatgg aatcagggct cccctgccgc | 720 |
| gagcacagac ccggcatgtt catctgcgtt ggtccccggg ctttcacagc cctcgctcta | 780 |
| gtcgggatgg ccaagggcct gcccgccgag ttcaagctca tcaacgacgc acacgccctc | 840 |
| gaagacgcgc ggatcctcga gctgctcgca atcaccgcgg gcatcttcct ctgggccctg | 900 |
| agtctgtggt tcttcttcat cgccgtcatc gccgtcctcc ggtccccgcc tacttccttc | 960 |
| catctcaact ggtgggcctt ggtcttcccg aacacgggct tcactttggc caccatcacg | 1020 |
| cttggaaagg cattgggcag tcccgggatc ttgggcgttg ttctgccat gtcccttggc | 1080 |
| atcgttggca tgtggctgtt tgtttttgtc agccatatcc gtgccatcat caaccaggat | 1140 |
| atcatgtatc cgggcaaaga tgaggatgct gcagactag | 1179 |

```
<210> SEQ ID NO 41
<211> LENGTH: 392
<212> TYPE: PRT
<213> ORGANISM: Aspergillus clavatus

<400> SEQUENCE: 41
```

```
Met Phe Glu Asn Arg Ile Pro Pro Thr Ser Ser Gln Ser Asp Ser Gly
1               5                   10                  15

Phe Leu Glu Asn Gln Leu Glu Lys Gln His Arg Leu Ser Leu Arg Glu
            20                  25                  30

Arg Leu Arg His Phe Thr Trp Ala Trp Tyr Thr Leu Thr Met Ser Thr
        35                  40                  45

Gly Gly Leu Ala Leu Leu Ile Ala Ser Gln Pro Tyr Thr Phe Lys Gly
50                  55                  60

Leu Lys Thr Ile Gly Leu Val Val Tyr Ile Val Asn Leu Ile Leu Phe
65                  70                  75                  80

Gly Leu Val Cys Ser Leu Met Ala Thr Arg Phe Ile Leu His Gly Gly
                85                  90                  95

Phe Leu Asp Ser Leu Arg His Glu Arg Glu Gly Leu Phe Phe Pro Thr
            100                 105                 110

Phe Trp Leu Ser Val Ala Thr Ile Ile Thr Gly Leu His Arg Tyr Phe
        115                 120                 125

Gly Ser Asp Ala Arg Glu Ser Tyr Leu Ile Ala Leu Glu Val Leu Phe
130                 135                 140

Trp Val Tyr Cys Ala Cys Thr Leu Ala Thr Ala Val Ile Gln Tyr Ser
145                 150                 155                 160

Phe Ile Phe Ser Ala His Arg Tyr Gly Leu Gln Thr Met Met Pro Ser
                165                 170                 175

Trp Ile Leu Pro Ala Phe Pro Ile Met Leu Ser Gly Thr Ile Ala Ser
            180                 185                 190

Val Ile Gly Glu Ala Gln Pro Ala Arg Ser Ser Ile Pro Val Ile Met
        195                 200                 205

Ala Gly Val Thr Phe Gln Gly Leu Gly Phe Ser Ile Ser Phe Met Met
210                 215                 220

Tyr Ala His Tyr Ile Gly Arg Leu Met Glu Ser Gly Leu Pro Cys Arg
225                 230                 235                 240

Glu His Arg Pro Gly Met Phe Ile Cys Val Gly Pro Ala Phe Thr
                245                 250                 255

Ala Leu Ala Leu Val Gly Met Ala Lys Gly Leu Pro Ala Glu Phe Lys
            260                 265                 270

Leu Ile Asn Asp Ala His Ala Leu Glu Asp Ala Arg Ile Leu Glu Leu
        275                 280                 285

Leu Ala Ile Thr Ala Gly Ile Phe Leu Trp Ala Leu Ser Leu Trp Phe
290                 295                 300

Phe Phe Ile Ala Val Ile Ala Val Leu Arg Ser Pro Thr Ser Phe
305                 310                 315                 320

His Leu Asn Trp Trp Ala Leu Val Phe Pro Asn Thr Gly Phe Thr Leu
                325                 330                 335

Ala Thr Ile Thr Leu Gly Lys Ala Leu Gly Ser Pro Gly Ile Leu Gly
            340                 345                 350

Val Gly Ser Ala Met Ser Leu Gly Ile Val Gly Met Trp Leu Phe Val
        355                 360                 365

Phe Val Ser His Ile Arg Ala Ile Ile Asn Gln Asp Ile Met Tyr Pro
370                 375                 380

Gly Lys Asp Glu Asp Ala Ala Asp
385                 390

<210> SEQ ID NO 42
<211> LENGTH: 1182
<212> TYPE: DNA
<213> ORGANISM: Aspergillus fumigatus
```

<400> SEQUENCE: 42

```
atgttcaacg atcatgatca tgttccacca acatcatcac agtcggattc tggcttttt       60
gaacaagaaa tgaagaaatc tcctcgacta agccttcgtg agcgcctacg gcacttcacc     120
tgggcgtggt ataccttgac gatgagtacc ggtggactgg ctcttctgat tgctagtcag     180
ccgtatacct tcaatggcat gaagggcatc gggatggtcg tttatatcct caatcttctg    240
ttattcgctc ttgtctgttc tttgatggtg ctgagattcg ttttgcatgg cggtttcctt     300
gacagcttgc gccaccctcg cgagggtctc ttcttcccta ccttctggct atccattgca    360
acgatcatca ctggcttgca tcgttacttc ggctccgacg acctagagtc gtacctcatc    420
gcactcgaag tcctcttctg ggtctactgt agttgcaccc tcgccacagc tgtgatccag    480
tactcattcc tctttgccgc ccactcctac ggcctgcaga caatgatgcc atcatggatc    540
ctaccagcct tccccatcat gctcagcgga accatcgcct cggtcatcag cgaatcccag    600
cccgcgcgat ccgcgatccc catcatcact gccggcgtta ccttccaggg cctcggcttc    660
tcaatcagct tcataatgta cgcccactac atcggccgac tcatgcagtc agggcttccc    720
tgccgcgaac acagaccagc catgttcatt tgcgtggggc ctccgtcttt caccgcgttg    780
gcgctagtag ggatggccaa gggcctgccc gacgaattca agataatcaa agacgcacac    840
gtcgaggacg cccggatcct cgagctgatg gctattatcg tcggcgtgtt cctgtgggcc    900
ctgagtctct ggttcttctt cattgccttt gttgctgtcg tccggtgccg gcccactgcg    960
ttccacctta gctggtgggc catggtcttc cccaacactg ggttcacgct ggccactatt   1020
accctgggga gggcattggg gagccctggc gtcttgggcg tcggctcggc catgtcggtc   1080
ggtgttgtct gcatgtgggt cttcgttttc gtctaccaca ttcgtgctgt catcaggcaa   1140
gacatcatgt acccgggcaa agacgaggat gtgctagatt aa                      1182
```

<210> SEQ ID NO 43
<211> LENGTH: 393
<212> TYPE: PRT
<213> ORGANISM: Aspergillus fumigatus

<400> SEQUENCE: 43

```
Met Phe Asn Asp His Asp His Val Pro Pro Thr Ser Ser Gln Ser Asp
1               5                   10                  15
Ser Gly Phe Phe Glu Gln Glu Met Lys Lys Ser Pro Arg Leu Ser Leu
            20                  25                  30
Arg Glu Arg Leu Arg His Phe Thr Trp Ala Trp Tyr Thr Leu Thr Met
        35                  40                  45
Ser Thr Gly Gly Leu Ala Leu Leu Ile Ala Ser Gln Pro Tyr Thr Phe
    50                  55                  60
Asn Gly Met Lys Gly Ile Gly Met Val Val Tyr Ile Leu Asn Leu Leu
65                  70                  75                  80
Leu Phe Ala Leu Val Cys Ser Leu Met Val Leu Arg Phe Val Leu His
                85                  90                  95
Gly Gly Phe Leu Asp Ser Leu Arg His Pro Arg Glu Gly Leu Phe Phe
            100                 105                 110
Pro Thr Phe Trp Leu Ser Ile Ala Thr Ile Ile Thr Gly Leu His Arg
        115                 120                 125
Tyr Phe Gly Ser Asp Asp Leu Glu Ser Tyr Leu Ile Ala Leu Glu Val
    130                 135                 140
Leu Phe Trp Val Tyr Cys Ser Cys Thr Leu Ala Thr Ala Val Ile Gln
145                 150                 155                 160
```

```
Tyr Ser Phe Leu Phe Ala Ala His Ser Tyr Gly Leu Gln Thr Met Met
            165                 170                 175

Pro Ser Trp Ile Leu Pro Ala Phe Pro Ile Met Leu Ser Gly Thr Ile
        180                 185                 190

Ala Ser Val Ile Ser Glu Ser Gln Pro Ala Arg Ser Ala Ile Pro Ile
    195                 200                 205

Ile Thr Ala Gly Val Thr Phe Gln Gly Leu Gly Phe Ser Ile Ser Phe
210                 215                 220

Ile Met Tyr Ala His Tyr Ile Gly Arg Leu Met Gln Ser Gly Leu Pro
225                 230                 235                 240

Cys Arg Glu His Arg Pro Ala Met Phe Ile Cys Val Gly Pro Pro Ser
                245                 250                 255

Phe Thr Ala Leu Ala Leu Val Gly Met Ala Lys Gly Leu Pro Asp Glu
            260                 265                 270

Phe Lys Ile Ile Lys Asp Ala His Val Glu Asp Ala Arg Ile Leu Glu
        275                 280                 285

Leu Met Ala Ile Ile Val Gly Val Phe Leu Trp Ala Leu Ser Leu Trp
    290                 295                 300

Phe Phe Phe Ile Ala Phe Val Ala Val Val Arg Cys Arg Pro Thr Ala
305                 310                 315                 320

Phe His Leu Ser Trp Trp Ala Met Val Phe Pro Asn Thr Gly Phe Thr
                325                 330                 335

Leu Ala Thr Ile Thr Leu Gly Arg Ala Leu Gly Ser Pro Gly Val Leu
            340                 345                 350

Gly Val Gly Ser Ala Met Ser Val Gly Val Val Cys Met Trp Val Phe
        355                 360                 365

Val Phe Val Tyr His Ile Arg Ala Val Ile Arg Gln Asp Ile Met Tyr
    370                 375                 380

Pro Gly Lys Asp Glu Asp Val Leu Asp
385                 390

<210> SEQ ID NO 44
<211> LENGTH: 1294
<212> TYPE: DNA
<213> ORGANISM: Aspergillus oryzae

<400> SEQUENCE: 44
atgttcgctg ctcgccagtc tttcaacctc ctccagaagc gcgccttctc cgcctctgcc      60
agccaggtgt gtgattgaat ggatccattg gacctcggag ctagctctgc aacatcaaca     120
aaactaacat actaacttat cttcttcata ggcttccaag gttgccgttc ttggtgccgc     180
tggtggcatt ggccagcctc tctcccttct cctcaagctc aaccccgtgt tttctgagct     240
tgccctctac gatatccgcg gtggccctgg tatgttttg cacagcttgc aacatctccg      300
acttcggtga ttcaagacag gctaacata aggatacaat aggtgttgcc gctgacctga      360
gccacatcaa caccaacagc accgtctctg ctacgaggc taccccctct ggcctccgtg       420
atgctctcaa gggctccgag atcgtcctca tccctgccgg tgttcctcgc aagcccggca     480
tgacccgtga cggtatgaac cgttaacttg tcaatggcac tgggaattga atactaatta     540
taatatcgcc agacctgttc aacaccaacg cctccattgt ccgcgacctt gctaaggccg     600
ccgccgaggc ttcccccgag ccaacatcc tcgtcatctc caaccctgta tgacgctttc      660
cacccactgc taccagttat ctcgcgctaa ttgcaatcag gtcaactcca ccgtcccat      720 cgtctctgag gtcttcaagt ccaagggtgt ctacaaccc aagcgtctct tcggtgtcac     780
```

```
tacccttgac gttgtccgtg cctctcgctt catctcccag gtccagaaga ccgacccctc    840
caacgaggcc gtcactgtcg tcggtggtca ctccggtgtg accattgtcc ctcttctctc    900
ccagtccagc cacccccagca ttgagggtaa gacccgcgat gagctcgtca accgcatcca    960
```
<br>

```
gttcggtggt gatgaggttg tcaaggccaa ggatggtgct ggctctgcca ccctctccat   1020
ggccatggct ggtgctcgca tggctgagtc cctcctgaag gccgcccagg gtgagaaggg   1080
tgtcgttgag cccactttcg tcgacagccc tctctacaag gaccagggtg ttgacttctt   1140
cgcctccaag gtcgagctcg gccccaacgg tgttgagaag atcctccccg ttggccaggt   1200
caacgcctac gaggagaagc tcctcgaggc ctgccttggt gacctcaaga gaacatcca   1260 gaagggtatt gacttcgtca aggccaaccc ttaa                              1294
```

<210> SEQ ID NO 45
<211> LENGTH: 340
<212> TYPE: PRT
<213> ORGANISM: Aspergillus oryzae

<400> SEQUENCE: 45

```
Met Phe Ala Ala Arg Gln Ser Phe Asn Leu Leu Gln Lys Arg Ala Phe
1               5                   10                  15

Ser Ala Ser Ala Ser Gln Ala Ser Lys Val Ala Val Leu Gly Ala Ala
                20                  25                  30

Gly Gly Ile Gly Gln Pro Leu Ser Leu Leu Leu Lys Leu Asn Pro Arg
            35                  40                  45

Val Ser Glu Leu Ala Leu Tyr Asp Ile Arg Gly Gly Pro Gly Val Ala
        50                  55                  60

Ala Asp Leu Ser His Ile Asn Thr Asn Ser Thr Val Ser Gly Tyr Glu
65                  70                  75                  80

Ala Thr Pro Ser Gly Leu Arg Asp Ala Leu Lys Gly Ser Glu Ile Val
                85                  90                  95

Leu Ile Pro Ala Gly Val Pro Arg Lys Pro Gly Met Thr Arg Asp Asp
            100                 105                 110

Leu Phe Asn Thr Asn Ala Ser Ile Val Arg Asp Leu Ala Lys Ala Ala
        115                 120                 125

Ala Glu Ala Ser Pro Glu Ala Asn Ile Leu Val Ile Ser Asn Pro Val
    130                 135                 140

Asn Ser Thr Val Pro Ile Val Ser Glu Val Phe Lys Ser Lys Gly Val
145                 150                 155                 160

Tyr Asn Pro Lys Arg Leu Phe Gly Val Thr Thr Leu Asp Val Val Arg
                165                 170                 175

Ala Ser Arg Phe Ile Ser Gln Val Gln Lys Thr Asp Pro Ser Asn Glu
            180                 185                 190

Ala Val Thr Val Val Gly Gly His Ser Gly Val Thr Ile Val Pro Leu
        195                 200                 205

Leu Ser Gln Ser Ser His Pro Ser Ile Glu Gly Lys Thr Arg Asp Glu
    210                 215                 220

Leu Val Asn Arg Ile Gln Phe Gly Gly Asp Glu Val Val Lys Ala Lys
225                 230                 235                 240

Asp Gly Ala Gly Ser Ala Thr Leu Ser Met Ala Met Ala Gly Ala Arg
                245                 250                 255

Met Ala Glu Ser Leu Leu Lys Ala Ala Gln Gly Glu Lys Gly Val Val
            260                 265                 270

Glu Pro Thr Phe Val Asp Ser Pro Leu Tyr Lys Asp Gln Gly Val Asp
        275                 280                 285
```

```
Phe Phe Ala Ser Lys Val Glu Leu Gly Pro Asn Gly Val Glu Lys Ile
        290                 295                 300

Leu Pro Val Gly Gln Val Asn Ala Tyr Glu Glu Lys Leu Leu Glu Ala
305                 310                 315                 320

Cys Leu Gly Asp Leu Lys Lys Asn Ile Gln Lys Gly Ile Asp Phe Val
                325                 330                 335

Lys Ala Asn Pro
            340

<210> SEQ ID NO 46
<211> LENGTH: 20
<212> TYPE: DNA
<213> ORGANISM: Aspergillus oryzae

<400> SEQUENCE: 46
tgaccttcca cgctgaccac                                              20

<210> SEQ ID NO 47
<211> LENGTH: 20
<212> TYPE: DNA
<213> ORGANISM: Aspergillus oryzae

<400> SEQUENCE: 47
ggctgagaaa atatgttgca                                              20

<210> SEQ ID NO 48
<211> LENGTH: 30
<212> TYPE: DNA
<213> ORGANISM: Aspergillus oryzae

<400> SEQUENCE: 48
gatagaccac taatcatggt ggcgatggag                                   30

<210> SEQ ID NO 49
<211> LENGTH: 30
<212> TYPE: DNA
<213> ORGANISM: Aspergillus oryzae

<400> SEQUENCE: 49
tgcggtcctg agtcaggccc agttgctcga                                   30

<210> SEQ ID NO 50
<211> LENGTH: 20
<212> TYPE: DNA
<213> ORGANISM: Aspergillus oryzae

<400> SEQUENCE: 50
gggatttgaa cagcagaagg                                              20

<210> SEQ ID NO 51
<211> LENGTH: 20
<212> TYPE: DNA
<213> ORGANISM: Aspergillus oryzae

<400> SEQUENCE: 51
tcacaaaaga gtagaggcca                                              20

<210> SEQ ID NO 52
<211> LENGTH: 36
<212> TYPE: DNA
<213> ORGANISM: Aspergillus clavatus

<400> SEQUENCE: 52
```
ccaacagaca catctaaaca atgtccgaca aggctc         36

<210> SEQ ID NO 53
<211> LENGTH: 40
<212> TYPE: DNA
<213> ORGANISM: Aspergillus clavatus

<400> SEQUENCE: 53
gtgtcagtca cctctagtta tcagctcttg gtgatattgt     40

<210> SEQ ID NO 54
<211> LENGTH: 750
<212> TYPE: DNA
<213> ORGANISM: Aspergillus clavatus

<400> SEQUENCE: 54
atgtccgaca aggctcgcga ggcggtctcg caatatctga agcagtctca cgagcgcatc    60
ttcgagaaca accgcgcctg gtcgcggcc aagaaggaag aggacccgc gtttttcgag    120
aaactgggcg ccggacagac gccgcaatat ctgtaaagac cagcatcagc gatttgtcat    180
tggagttgtc ggatgacttt gccatactga ccgtggctgt gcaggtacat cggatgcagt    240
gacagtcgcg tgcccgccaa tgacattatg ggtctcacgg ccggcgaggt ctttgtgcac    300
cgcaacatcg ccaatctggt gcccaacacc gacctcaatg tcatgtcggt catcaactac    360
gccgtccggc atctgaaggt caagcacatc gttgtctgcg ccactacaa ctgtggcggt    420
gtcaaggctg cgctgacgcc ctccgacctg gggctgctga accctggct gcgcaatgtc    480
cgggatgtgt atcggttgca cgagcgcgag ctggacgcca tcgaagacga agaggcgaag    540
tataatcgcc tggtggagct gaatgttgtt gagtcctgcc gcaacgtcat caagacggcg    600
gcggtgcagc agagctacca cgacaaccag ttccccgtgg tccacggatg gatctttgat    660
gtgcggacgg gtctgcttcg ggatctcaac attgatttcg aggagacgct gcgggatatc    720
aagaagatct acaatatcac caagagctga                                     750

<210> SEQ ID NO 55
<211> LENGTH: 225
<212> TYPE: PRT
<213> ORGANISM: Aspergillus clavatus

<400> SEQUENCE: 55

Met Ser Asp Lys Ala Arg Glu Ala Val Ser Gln Tyr Leu Lys Gln Ser
1               5                   10                  15

His Glu Arg Ile Phe Glu Asn Asn Arg Ala Trp Val Ala Ala Lys Lys
            20                  25                  30

Glu Glu Asp Pro Ala Phe Phe Glu Lys Leu Gly Ala Gly Gln Thr Pro
        35                  40                  45

Gln Tyr Leu Tyr Ile Gly Cys Ser Asp Ser Arg Val Pro Ala Asn Asp
    50                  55                  60

Ile Met Gly Leu Thr Ala Gly Glu Val Phe Val His Arg Asn Ile Ala
65                  70                  75                  80

Asn Leu Val Pro Asn Thr Asp Leu Asn Val Met Ser Val Ile Asn Tyr
                85                  90                  95

Ala Val Arg His Leu Lys Val Lys His Ile Val Val Cys Gly His Tyr
            100                 105                 110

Asn Cys Gly Gly Val Lys Ala Ala Leu Thr Pro Ser Asp Leu Gly Leu
        115                 120                 125

Leu Asn Pro Trp Leu Arg Asn Val Arg Asp Val Tyr Arg Leu His Glu
    130                 135                 140

Arg Glu Leu Asp Ala Ile Glu Asp Glu Ala Lys Tyr Asn Arg Leu
145                 150                 155                 160

Val Glu Leu Asn Val Val Glu Ser Cys Arg Asn Val Ile Lys Thr Ala
                165                 170                 175

Ala Val Gln Gln Ser Tyr His Asp Asn Gln Phe Pro Val His Gly
            180                 185                 190

Trp Ile Phe Asp Val Arg Thr Gly Leu Leu Arg Asp Leu Asn Ile Asp
        195                 200                 205

Phe Glu Glu Thr Leu Arg Asp Ile Lys Lys Ile Tyr Asn Ile Thr Lys
    210                 215                 220

Ser
225

<210> SEQ ID NO 56
<211> LENGTH: 37
<212> TYPE: DNA
<213> ORGANISM: Aspergillus oryzae

<400> SEQUENCE: 56
attaactaaa gaccacgaga ggggaactag ggaaatc                               37

<210> SEQ ID NO 57
<211> LENGTH: 28
<212> TYPE: DNA
<213> ORGANISM: Aspergillus oryzae

<400> SEQUENCE: 57
ttaattaact ttccccccg taatctaa                                          28

<210> SEQ ID NO 58
<211> LENGTH: 45
<212> TYPE: DNA
<213> ORGANISM: Aspergillus oryzae

<400> SEQUENCE: 58
ggaaacagct atgaccatga ttatggattg tttaaacgtc gacgc                      45

<210> SEQ ID NO 59
<211> LENGTH: 45
<212> TYPE: DNA
<213> ORGANISM: Aspergillus oryzae

<400> SEQUENCE: 59
gcgtcgacgt ttaaacaatc cataatcatg gtcatagctg tttcc                      45

<210> SEQ ID NO 60
<211> LENGTH: 38
<212> TYPE: DNA
<213> ORGANISM: Aspergillus oryzae

<400> SEQUENCE: 60
ggaaacagct atgaccatga ttccagattg taaattac                              38

<210> SEQ ID NO 61
<211> LENGTH: 40
<212> TYPE: DNA
<213> ORGANISM: Aspergillus oryzae

<400> SEQUENCE: 61
agcactagta cgcgtagatc tgtttagatg tgtctgttgg                            40

<210> SEQ ID NO 62
<211> LENGTH: 3228
<212> TYPE: DNA
<213> ORGANISM: Escherichia coli

<400> SEQUENCE: 62

| | | | | | |
|---|---|---|---|---|---|
| attaactaaa | gaccacgaga | ggggaactag | ggaaatccgt | gatagaatga | agtatacagt | 60 |
| tgattttgtc | agcaagggat | tcaaacctaa | taccagaggt | gactttatcc | aagattcctt | 120 |
| cacgacactg | gaagaactgc | ttgaagagct | gcctgagtca | atcagcttca | atatcgagat | 180 |
| aagtaggtta | tatgctgcca | ctggtggttc | tccacttgcg | ggagacaaag | ctaacaacgt | 240 |
| cccaatgaag | agtaccccag | gcttcatgaa | gctatagaag | caggtgtagc | accagtggct | 300 |
| attgaaatca | acaccttcat | cgacaaagcg | cttgagagac | tcttttctta | cggcaacaaa | 360 |
| aaacggacca | ttatcctatc | ctcatttact | cccgagatct | gcattttatt | ggccatcaaa | 420 |
| caacagacgt | accctgtgat | gttcatcact | aatgccggca | agcctccagt | tacggatcga | 480 |
| gagatgaggg | ctgccagcat | acagtccgct | gttcgatttg | ccaagaggtg | gaatttatct | 540 |
| ggccttgtct | ttgcatctga | ggcgctggta | atgtgcccca | ggcttgtcag | atatgttcaa | 600 |
| cgatcaggat | tgatctgtgg | atcctatgga | tctcagaaca | atataccaga | aaatgcgaag | 660 |
| gtaagtgctt | ctatattgat | ccttagtgct | ttcaaactgt | gatgtagaag | ttgctcggta | 720 |
| gctgattaaa | tattctagac | ccaagccgct | gctggaattg | acattattat | ggccgatagg | 780 |
| gttgggctta | ttgctatgtc | cctgaaagga | tatcaaaagc | aggcaaaaag | ccaggcataa | 840 |
| tccccgcgtg | gacggtaccc | taaggatagg | ccctaatctt | atctacatgt | gactgcatcg | 900 |
| atgtgtttgg | tcaaaatgag | gcatgtggct | cacccacag | gcggagaaac | gtgtggctag | 960 |
| tgcatgacag | tcccctccat | agattcaatt | taattttcg | cggcaattgt | cgtgcagttt | 1020 |
| gtatctacat | ttcattccat | atatcaagag | ttagtagttg | gacatcctga | ttattttgtc | 1080 |
| taattactga | aaactcgaag | tactaaccta | ctaataagcc | agtttcaacc | actaagtgct | 1140 |
| catttataca | atatttgcag | aaccccgcgc | taccctcca | tcgccaacat | gtaagtagtg | 1200 |
| gtggatacgt | actccttta | tggcagtatg | tcgcaagtat | gatgcgattt | ataaattcag | 1260 |
| cactcgaaat | gactactact | atgtgtctac | gacagatacc | ctctccgtac | gaataagaca | 1320 |
| cctgcctcga | tatatggaca | aattcaaaat | cagggtcaag | ggtcatgttt | caaagtcaca | 1380 |
| acaatctcca | acatagacga | gaatttgtac | cggagtgtct | gaaggtgcag | ctggagattg | 1440 |
| gtctatttc | ttagagtggg | gtatcactaa | tgtacagtcg | gtcactatcg | tacaaacaat | 1500 |
| cacaattata | tacaagattt | cccaccaccc | cctactctaa | cacggcacaa | ttatccatcg | 1560 |
| agtcagagcc | tagccaccat | ttggtgctct | cgtagagacc | aaagtataat | cctgatccga | 1620 |
| cagcggccat | aaacgtgttg | atagcacacc | ctcggaatag | tcctctcggg | ccatctgttc | 1680 |
| gtacaatctc | ccgtacggta | ttgatcatcc | ttttcttctg | aggtgcagtt | gtatctgcag | 1740 |
| catcgagcat | gattcgtgtc | cggaccatat | ccatgggtgc | tgtcaagaca | ctagctatac | 1800 |
| cgcccgagac | cgcagcactt | attgcggctg | tcgctgcagc | ctctccgatt | gtcgaatggg | 1860 |
| cctctttctt | tccatactct | cttggtcttt | ctagcacctt | ctctcgatct | ccgaatctat | 1920 |
| attcaaaaat | tcgataccga | aaagactcgt | acagaggcat | ctgaatcgcc | gacactggca | 1980 |
| agctatgcgc | cacaagagcc | gggtatccgc | tccaaagctg | tctagggttg | ataaacttct | 2040 |
| tgaaagctag | ccgtgtcgct | ttctgggcta | caccacctac | ccttcccca | gctacaggtg | 2100 |
| ctgatgcgtc | tggatggtgt | gattggatca | tctgcgcgtt | gtgttttaat | gcatcagccg | 2160 |
| gagcaaagac | tccgcaagca | gcaagatccg | caacggaggc | tgcgcaaaaa | tcggaaaaga | 2220 |

```
gccgagctga gctagactca tgcgttccaa gttttttgatg tatgacttgg agtcctgact    2280
gtgcatactc gtatgtgatg aagaatgcgc ccgcttttgac ccgttatttt ttgctcaatg    2340
aatatgagtt gggtaaggat aatgttgggt atcaccaacc tgtgggaaat gaggcagcgg    2400
ttacgctcgc gataccttgg taaaggccgc ggaatatccc tgggtgtctc catatgctgg    2460
ttcctgtgtt ggttctcagg aactgcgaat attcgcgaga ctgaatgcgg gttttgatcg    2520
tatctaaggg atatgtgaat agatctagtg agagggatgc ggttgtgctt gcctagttcc    2580
ctcaggttaa tgtatgctgt ttgtccaagg gggttagaaa atataccagc aatatactaa    2640
gtggctcggc ggccatatta tttgtcgata gaggcgggag gacgaggatg ttcaatcgtg    2700
gattttgtaa ccgtcctggc acacatcacc ttacaaggct ttgagttttc gttctataat    2760
ttgagacagg tcacagtcga ttgccatatt agattacagc aacgtaggta gacattagga    2820
ttgatgccag gcagcgaagt ttttttcact attggatgag tttattccgg gctccgcggg    2880
aaccgattgg ggtctgacat ttctggaaaa tccccaaaca tatttcattt tgtctttgcg    2940
gacagataaa acgctttcga ttccgatagt agaggtatat acacatcgag tgtaaacagt    3000
ataagcatat agtctctcgg tttgttagcg gttttgacgc atactaataa atcatcgata    3060
actagtactg ctatcgataa gctccttgac ggggaaaggt agcaggaccc actgcagtca    3120
ctttagtaag tggatgtcag gatgataagg agatatagag atatgcagct gataagctta    3180
gaacgtgacc tgaaggaaga cattaaaatt agattacggg ggggaaag              3228

<210> SEQ ID NO 63
<211> LENGTH: 41
<212> TYPE: DNA
<213> ORGANISM: Artificial Sequence
<220> FEATURE:
<223> OTHER INFORMATION: ARTIFICIAL DNA PRIMER

<400> SEQUENCE: 63
gtgatagaac atcgtccata atgccgggcg atctcaaaac c                          41

<210> SEQ ID NO 64
<211> LENGTH: 39
<212> TYPE: DNA
<213> ORGANISM: Artificial Sequence
<220> FEATURE:
<223> OTHER INFORMATION: ARTIFICIAL DNA PRIMER

<400> SEQUENCE: 64
gtgtcagtca cctctagtta ctatgcatca aggacattc                              39

<210> SEQ ID NO 65
<211> LENGTH: 20
<212> TYPE: DNA
<213> ORGANISM: Artificial Sequence
<220> FEATURE:
<223> OTHER INFORMATION: ARTIFICIAL DNA PRIMER

<400> SEQUENCE: 65
gattgagatc ggcatttact                                                   20

<210> SEQ ID NO 66
<211> LENGTH: 20
<212> TYPE: DNA
<213> ORGANISM: Artificial Sequence
<220> FEATURE:
<223> OTHER INFORMATION: ARTIFICIAL DNA PRIMER

<400> SEQUENCE: 66
```

```
-continued acgcggaaca gcagaatggc                                           20

<210> SEQ ID NO 67
<211> LENGTH: 25
<212> TYPE: DNA
<213> ORGANISM: Artificial Sequence
<220> FEATURE:
<223> OTHER INFORMATION: ARTIFICIAL DNA PRIMER

<400> SEQUENCE: 67
ctatagcgaa atggattgat tgtct                                     25

<210> SEQ ID NO 68
<211> LENGTH: 20
<212> TYPE: DNA
<213> ORGANISM: Artificial Sequence
<220> FEATURE:
<223> OTHER INFORMATION: ARTIFICIAL DNA PRIMER

<400> SEQUENCE: 68
ttcaccgtga aacgtattga                                           20
```